(12) United States Patent
Markovic et al.

(10) Patent No.: US 10,391,055 B2
(45) Date of Patent: *Aug. 27, 2019

(54) CARRIER-ANTIBODY COMPOSITIONS AND METHODS OF MAKING AND USING THE SAME

(71) Applicant: Mayo Foundation for Medical Education and Research, Rochester, MN (US)

(72) Inventors: Svetomir N. Markovic, Rochester, MN (US); Wendy K. Nevala, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 157 days.

This patent is subject to a terminal disclaimer.

(21) Appl. No.: 15/331,754

(22) Filed: Oct. 21, 2016

(65) Prior Publication Data

US 2017/0100492 A1    Apr. 13, 2017

Related U.S. Application Data

(60) Continuation of application No. 15/060,912, filed on Mar. 4, 2016, now Pat. No. 9,555,128, which is a division of application No. 14/882,327, filed on Oct. 13, 2015, now Pat. No. 9,446,148, which is a continuation of application No. PCT/US2015/054295, filed on Oct. 6, 2015.

(60) Provisional application No. 62/206,772, filed on Aug. 18, 2015, provisional application No. 62/206,770, filed on Aug. 18, 2015, provisional application No. 62/206,771, filed on Aug. 18, 2015, provisional application No. 62/060,484, filed on Oct. 6, 2014.

(51) Int. Cl.

| | |
|---|---|
| *A61K 39/395* | (2006.01) |
| *A61K 9/00* | (2006.01) |
| *A61K 31/337* | (2006.01) |
| *A61K 51/10* | (2006.01) |
| *A61K 9/14* | (2006.01) |
| *A61K 9/19* | (2006.01) |
| *A61K 33/24* | (2019.01) |
| *C07K 16/30* | (2006.01) |
| *C07K 16/40* | (2006.01) |
| *C07K 16/22* | (2006.01) |
| *A61K 9/16* | (2006.01) |
| *C07K 16/28* | (2006.01) |
| *C07K 16/32* | (2006.01) |
| *A61K 9/08* | (2006.01) |
| *A61K 47/64* | (2017.01) |
| *A61K 47/68* | (2017.01) |
| *A61K 47/69* | (2017.01) |
| *A61K 39/00* | (2006.01) |

(52) U.S. Cl.
CPC ............ *A61K 9/0095* (2013.01); *A61K 9/08* (2013.01); *A61K 9/146* (2013.01); *A61K 9/1658* (2013.01); *A61K 9/19* (2013.01); *A61K 31/337* (2013.01); *A61K 33/24* (2013.01); *A61K 39/3955* (2013.01); *A61K 47/643* (2017.08); *A61K 47/6803* (2017.08); *A61K 47/6845* (2017.08); *A61K 47/6849* (2017.08); *A61K 47/6851* (2017.08); *A61K 47/6871* (2017.08); *A61K 47/6929* (2017.08); *A61K 47/6931* (2017.08); *A61K 51/1021* (2013.01); *C07K 16/22* (2013.01); *C07K 16/2863* (2013.01); *C07K 16/2887* (2013.01); *C07K 16/30* (2013.01); *C07K 16/32* (2013.01); *C07K 16/40* (2013.01); *A61K 2039/505* (2013.01); *C07K 2317/24* (2013.01); *C07K 2317/52* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,350,687 | A | 9/1982 | Lipton et al. |
| 5,026,772 | A | 6/1991 | Kobayashi et al. |
| 5,116,944 | A | 5/1992 | Sivam et al. |
| 5,216,130 | A | 6/1993 | Line et al. |
| 5,252,713 | A | 10/1993 | Morgan, Jr. et al. |
| 5,260,308 | A | 11/1993 | Poduslo et al. |
| 5,728,541 | A | 3/1998 | Kornblith |
| 5,736,137 | A | 4/1998 | Anderson et al. |
| 6,054,297 | A | 4/2000 | Carter et al. |
| 6,147,060 | A | 11/2000 | Zasloff et al. |
| 6,416,967 | B2 | 7/2002 | Kornblith |
| 6,537,579 | B1 | 3/2003 | Desai et al. |
| 6,933,129 | B1 | 8/2005 | Kornblith |
| 7,041,301 | B1 | 5/2006 | Markovic |
| 7,112,409 | B2 | 9/2006 | Blumenthal et al. |
| 7,678,552 | B2 | 3/2010 | Kornblith |
| 7,731,950 | B2 | 6/2010 | Noessner et al. |
| 7,758,891 | B2 | 7/2010 | Desai et al. |
| 7,820,788 | B2 | 10/2010 | Desai et al. |

(Continued)

FOREIGN PATENT DOCUMENTS

| | | |
|---|---|---|
| EP | 1 913 947 A1 | 4/2008 |
| JP | S60146833 | 8/1985 |

(Continued)

OTHER PUBLICATIONS

U.S. Appl. No. 14/116,619, filed Feb. 7, 2014.

(Continued)

*Primary Examiner* — Yunsoo Kim
(74) *Attorney, Agent, or Firm* — Myers Bigel, P.A.

(57) ABSTRACT

Described herein are compositions of antibodies and carrier proteins and methods of making and using the same, in particular, as a cancer therapeutic. Also described are lyophilized compositions of antibodies and carrier proteins and methods of making and using the same, in particular, as a cancer therapeutic.

24 Claims, 44 Drawing Sheets

(56) References Cited

U.S. PATENT DOCUMENTS

| | | |
|---|---|---|
| 7,906,121 B2 | 3/2011 | Chang et al. |
| 7,923,536 B2 | 4/2011 | Desai et al. |
| 8,034,375 B2 | 10/2011 | Desai et al. |
| 8,119,129 B2 | 2/2012 | Jure-Kunkel et al. |
| 8,138,229 B2 | 3/2012 | Desai et al. |
| 8,268,348 B2 | 9/2012 | Desai et al. |
| 8,314,156 B2 | 11/2012 | Desai et al. |
| 8,344,177 B2 | 1/2013 | Neri et al. |
| 8,735,394 B2 | 5/2014 | Desai et al. |
| 8,853,260 B2 | 10/2014 | Desai et al. |
| 9,101,543 B2 | 8/2015 | Desai et al. |
| 9,387,244 B2 | 7/2016 | Markovic |
| 9,427,477 B2 | 8/2016 | Markovic et al. |
| 9,446,148 B2 | 9/2016 | Markovic et al. |
| 9,466,148 B2 | 10/2016 | Gay et al. |
| 9,533,058 B2 | 1/2017 | Markovic et al. |
| 9,555,128 B2 * | 1/2017 | Markovic ............ A61K 31/337 |
| 9,566,350 B2 | 2/2017 | Markovic et al. |
| 9,757,453 B2 | 9/2017 | Markovic et al. |
| 2002/0111362 A1 | 8/2002 | Rubinfeld |
| 2004/0005318 A1 | 1/2004 | Davis et al. |
| 2004/0077601 A1 | 4/2004 | Adams et al. |
| 2005/0032699 A1 | 2/2005 | Holash et al. |
| 2006/0165652 A1 | 7/2006 | Dudley et al. |
| 2007/0020232 A1 | 1/2007 | Rossignol et al. |
| 2007/0166388 A1 | 7/2007 | Desai et al. |
| 2009/0004118 A1 | 1/2009 | Nie et al. |
| 2010/0047234 A1 | 2/2010 | Markovic |
| 2010/0092489 A1 | 4/2010 | Van De Winkel et al. |
| 2010/0112077 A1 | 5/2010 | Desai et al. |
| 2010/0172835 A1 | 7/2010 | Ruoslahti et al. |
| 2010/0260679 A1 | 10/2010 | Shachar et al. |
| 2010/0311679 A1 | 12/2010 | Olson et al. |
| 2011/0076273 A1 | 3/2011 | Adler et al. |
| 2011/0097340 A1 | 4/2011 | Ramachandra et al. |
| 2011/0104143 A1 | 5/2011 | Buchsbaum et al. |
| 2011/0150902 A1 | 6/2011 | Markovic |
| 2011/0262525 A1 | 10/2011 | Wang et al. |
| 2012/0263739 A1 | 10/2012 | Langer et al. |
| 2012/0315273 A1 | 12/2012 | Markovic |
| 2013/0028895 A1 | 1/2013 | Wulf |
| 2013/0071403 A1 | 3/2013 | Rolland et al. |
| 2013/0149238 A1 | 6/2013 | Kavlie et al. |
| 2013/0164816 A1 | 6/2013 | Chang et al. |
| 2014/0056909 A1 | 2/2014 | Markovic |
| 2014/0155344 A1 | 6/2014 | Neil et al. |
| 2014/0161819 A1 | 6/2014 | Hann et al. |
| 2014/0178486 A1 | 6/2014 | Markovic et al. |
| 2014/0302017 A1 | 10/2014 | Markovic |
| 2014/0314774 A1 | 10/2014 | Zhou et al. |
| 2015/0050356 A1 | 2/2015 | Desai et al. |
| 2015/0246122 A1 | 9/2015 | Markovic et al. |
| 2016/0095942 A1 | 4/2016 | Markovic et al. |
| 2016/0184229 A1 | 6/2016 | Markovic et al. |
| 2016/0184452 A1 | 6/2016 | Markovic et al. |
| 2016/0184453 A1 | 6/2016 | Markovic et al. |
| 2016/0235860 A1 | 8/2016 | Markovic et al. |
| 2016/0250351 A1 | 9/2016 | Markovic et al. |
| 2016/0256431 A1 | 9/2016 | Markovic et al. |
| 2016/0263241 A1 | 9/2016 | Markovic et al. |
| 2016/0310610 A1 | 10/2016 | Markovic et al. |
| 2016/0324964 A1 | 11/2016 | Markovic et al. |
| 2016/0338961 A1 | 11/2016 | Markovic et al. |
| 2016/0339118 A1 | 11/2016 | Markovic et al. |
| 2017/0021023 A1 | 1/2017 | Dikstein |
| 2017/0021032 A1 | 1/2017 | Markovic et al. |
| 2017/0021034 A1 | 1/2017 | Markovic et al. |
| 2017/0071897 A1 | 3/2017 | Markovic et al. |
| 2017/0095574 A1 | 4/2017 | Swiss et al. |
| 2017/0100492 A1 | 4/2017 | Markovic et al. |
| 2017/0106087 A1 | 4/2017 | Markovic et al. |
| 2017/0128408 A1 | 5/2017 | Markovic et al. |
| 2017/0128583 A1 | 5/2017 | Markovic et al. |
| 2017/0128584 A1 | 5/2017 | Markovic et al. |
| 2017/0128585 A1 | 5/2017 | Markovic et al. |
| 2017/0128586 A1 | 5/2017 | Markovic et al. |
| 2017/0128587 A1 | 5/2017 | Markovic et al. |
| 2017/0128588 A1 | 5/2017 | Markovic et al. |
| 2017/0182174 A1 | 6/2017 | Markovic et al. |
| 2017/0182175 A1 | 6/2017 | Markovic et al. |
| 2017/0182180 A1 | 6/2017 | Markovic et al. |
| 2017/0182183 A1 | 6/2017 | Markovic et al. |
| 2017/0182184 A1 | 6/2017 | Markovic et al. |
| 2017/0182185 A1 | 6/2017 | Markovic et al. |
| 2017/0182186 A1 | 6/2017 | Markovic et al. |
| 2017/0182187 A1 | 6/2017 | Markovic et al. |
| 2017/0196831 A1 | 7/2017 | Markovic et al. |
| 2017/0196832 A1 | 7/2017 | Markovic et al. |
| 2017/0196833 A1 | 7/2017 | Markovic et al. |
| 2017/0216453 A1 | 8/2017 | Markovic et al. |
| 2017/0232102 A1 | 8/2017 | Markovic et al. |
| 2017/0291952 A1 | 10/2017 | Markovic et al. |

FOREIGN PATENT DOCUMENTS

| | | |
|---|---|---|
| JP | S6178731 | 4/1986 |
| JP | H04504253 | 7/1992 |
| JP | 2001-072589 | 3/2001 |
| KR | 1020090078330 | 7/2009 |
| RU | 2011133819 | 2/2013 |
| WO | WO-89/10398 A1 | 11/1989 |
| WO | WO-97/49390 A1 | 12/1997 |
| WO | WO-99/00113 A1 | 1/1999 |
| WO | WO-99/51248 A1 | 10/1999 |
| WO | 2004/022097 | 3/2004 |
| WO | WO-2004/096224 A2 | 11/2004 |
| WO | 2006/089290 | 8/2006 |
| WO | 2007/027819 | 3/2007 |
| WO | 2007/027941 | 3/2007 |
| WO | 2008/047272 | 4/2008 |
| WO | 2008/057561 | 5/2008 |
| WO | WO-2008/057562 A1 | 5/2008 |
| WO | WO-2008/112987 A1 | 9/2008 |
| WO | WO-2009/043159 A1 | 4/2009 |
| WO | WO-2009/055343 A2 | 4/2009 |
| WO | WO-2010/003057 A2 | 1/2010 |
| WO | WO-2010/017216 A2 | 2/2010 |
| WO | 2010/118365 | 10/2010 |
| WO | 2010/124009 | 10/2010 |
| WO | WO-2012/048223 A1 | 4/2012 |
| WO | WO-2012/088388 A2 | 6/2012 |
| WO | WO-2012/154861 A2 | 11/2012 |
| WO | WO-2014/009774 | 1/2014 |
| WO | WO-2014/055415 A1 | 4/2014 |
| WO | WO-2014/123612 | 8/2014 |
| WO | 2015/048520 | 4/2015 |
| WO | WO-2015/191969 A1 | 12/2015 |
| WO | WO-2015/195476 A1 | 12/2015 |
| WO | 2016/059220 | 4/2016 |
| WO | WO-2016/057554 A1 | 4/2016 |
| WO | 2016/089873 | 6/2016 |
| WO | 2017/031368 | 2/2017 |
| WO | 2017/062063 | 4/2017 |
| WO | 2017/120501 | 7/2017 |
| WO | 2017/139698 | 8/2017 |
| WO | 2017/165439 | 9/2017 |
| WO | 2017/165440 | 9/2017 |
| WO | 2017/176265 | 10/2017 |
| WO | 2018/027205 | 2/2018 |
| WO | 2018/045238 | 3/2018 |
| WO | 2018/045239 | 3/2018 |
| WO | 2018/048815 | 3/2018 |
| WO | 2018/048816 | 3/2018 |
| WO | 2018/048958 | 3/2018 |

OTHER PUBLICATIONS

U.S. Appl. No. 15/052,623, filed Feb. 24, 2016.
U.S. Appl. No. 14/432,979, filed Apr. 1, 2015.
U.S. Appl. No. 15/052,336, filed Feb. 24, 2016.
U.S. Appl. No. 15/187,672, filed Jun. 20, 2016.
U.S. Appl. No. 15/202,115, filed Jul. 5, 2016.
U.S. Appl. No. 15/413,257, filed Jan. 23, 2017.

(56) References Cited

OTHER PUBLICATIONS

U.S. Appl. No. 15/412,581, filed Jan. 23, 2017.
U.S. Appl. No. 15/412,564, filed Jan. 23, 2017.
U.S. Appl. No. 15/412,596, filed Jan. 23, 2017.
U.S. Appl. No. 15/412,610, filed Jan. 23, 2017.
U.S. Appl. No. 15/412,536, filed Jan. 23, 2017.
U.S. Appl. No. 15/412,554, filed Jan. 23, 2017.
U.S. Appl. No. 15/414,533, filed Jan. 24, 2017.
U.S. Appl. No. 15/414,536, filed Jan. 24, 2017.
U.S. Appl. No. 15/414,526, filed Jan. 24, 2017.
U.S. Appl. No. 15/225,504, filed Aug. 1, 2016.
U.S. Appl. No. 15/225,542, filed Aug. 1, 2016.
U.S. Appl. No. 15/286,024, filed Oct. 5, 2016.
U.S. Appl. No. 15/286,006, filed Oct. 5, 2016.
U.S. Appl. No. 15/359,569, filed Nov. 22, 2016.
U.S. Appl. No. 15/456,377, filed Mar. 10, 2017.
U.S. Appl. No. 15/456,382, filed Mar. 10, 2017.
U.S. Appl. No. 15/456,391, filed Mar. 10, 2017.
U.S. Appl. No. 15/456,395, filed Mar. 10, 2017.
U.S. Appl. No. 15/456,399, filed Mar. 10, 2017.
U.S. Appl. No. 15/460,552, filed Mar. 16, 2017.
U.S. Appl. No. 15/460,699, filed Mar. 16, 2017.
U.S. Appl. No. 15/461,288, filed Mar. 16, 2017.
U.S. Appl. No. 15/225,428, filed Aug. 1, 2016.
U.S. Appl. No. 15/092,433, filed Apr. 6, 2016.
U.S. Appl. No. 15/092,403, filed Apr. 6, 2016.
U.S. Appl. No. 15/030,567, filed Apr. 19, 2016.
U.S. Appl. No. 15/452,669, filed Mar. 7, 2017.
U.S. Appl. No. 15/030,568, filed Apr. 19, 2016.
U.S. Appl. No. 15/430,411, filed Feb. 10, 2017.
Abraxis Bioscience, Inc., "Abraxane: For the adjuvant treatment of node-positive breast cancer administered sequentially to standard doxorubicin-containing combination chemotherapy," Oncologic Drugs Advisory Committee Meeting (available to public Aug. 4, 2006).
Bairagi et al., Albumin: A Versatile Drug Carrier, Austin Therapeutics, (Nov. 17, 2015) vol. 2, No. 2, p. 1021 (pp. 1-6), especially abstract, p. 2, Table 2, p. 2 col. 2 para. 2.
International Search Report and Written Opinion for Application No. PCT/US17/17553 dated May 3, 2017, 13 pages.
International Search Report and Written Opinion, PCT/US2017/023442, Mayo Foundation for Medical Education and Research, 8 pages (dated Jun. 16, 2017).
International Search Report and Written Opinion, PCT/US2017/023443, Mayo Foundation for Medical Education and Research, 10 pages (dated Jul. 11, 2017).
Lundin et al., Phase 2 Study of Alemtuzumab (anti-CD52 Monoclonal Antibody) in Patients with Advanced Mycosis Fungoides/Sezary Syndrome, Blood. (Jun. 1, 2003) vol. 101, No. 11, pp. 4267-4272, especially p. 4267 col. 1, para. 1, p. 4267 col. 2, para 2-p. 4268 col. 1, para. 1, p. 4271 col. 1, para. 3.
Vishnu, P. et al., Safety and efficacy of nab-paclitaxel in the treatment of patients with breast cancer, Breast Cancer: Basic and Clinical Research, vol. 5, pp. 53-65 (2011).
"A Study of Bevacizumab With Carboplatin and Paclitaxel Chemotherapy for the First-Line Treatment of Patients With Metastatic Melanoma (BEAM)," ClinicalTrials.gov [online]. Retrieved from the Internet: <URL: https://clinicaltrials.gov/archive/NCT00434252/200703 12>, dated Mar. 12, 2007, 3 pages.
"Concurrent Infusions", J Oncol Pract., 4(4): 171, Jul. 2008.
AACR Presentation, "Targeted nano-immune conjugates to melanoma: Pre-clinical testing of bevacizumab targeted nab-paclitaxel," Mayo Clinic, 2014.
Abraxane® for Injectable Suspension (paclitaxel protein-bound particles for injectable suspension) (albumin-bound), [drug label], 22 pages, Sep. 2009.
Agarwal et al., "Flow Cytometric analysis of Th1 and Th2 cytokines in PBMCs as a parameter of immunological dysfunction in patients of Superficial Transitional cell carcinoma of bladder", Cancer Immunol. Immunother., 2006, 55(6):734-743.
Agarwala et al., "Randomized phase III study of paclitaxel plus carboplatin with or without sorafenib as second-line treatment in patients with advanced melanoma", J. Clin. Oncol., 2007, 25(185):8510 (Abstract).
Allen, TM, "Ligand-targeted therapeutics in anticancer therapy, Cancer", Oct. 2002, 2(10), pp. 750-763.
Alley et al., "Contribution of Linker Stability to the Activities of Anticancer Immunoconjugates", Bioconjugate Chem., 2008, 19(3), pp. 759-765.
Anonymous, "A Phase II, multicenter, randomized, double-blind placebo-controlled trial evaluating the efficacy and safety of bevacizumab in combination with carboplatin and paclitaxel chemotherapy for the first-line treatment of patients with metastatic melanoma", U.S. National Institutes of Health, 2007, 3 pages.
Anonymous, "Phase II trial of carboplatin, weekly paclitaxel and biweekly bevacizumab in patients with unresectable stage IV melanoma", U.S. National Institutes of Health, 2007, 4 pages.
Arakawa et al., "Protein-Solvent Interactions in Pharmaceutical Formulations", Pharm. Res., Mar. 1991, vol. 8, Issue 3, pp. 285-291.
Asadullah et al., "Interleukin-10 therapy—review of a new approach", Pharmarcol Rev., 2003, 55(2):241-269.
Atkins et al., "High-dose recombinant interleukin-2 therapy in patients with metastatic melanoma: long-term survival update", Cancer J Sci Am., 2000, Suppl 6:S11-14.
Atkins, Michael, "Interleukin-2: clinical applications", Semin Oncol., 2002, 29(3 Suppl 7):12-27.
Avastin® Bevacizumab, Roche, [drug label], 24 pages, Sep. 2008.
Balch et al., "The new melanoma staging system", Semin Cutan Med Surg., 2003, 22(1):42-54.
Balch et al., "Update on the melanoma staging system: The importance of sentinel node staging and primary tumor mitotic rate", Journal of Surgical Oncology, Aug. 19, 2011, vol. 104, Issue 4, pp. 379-385.
Bauer, K., et al., "Rituximab, ofatumumab, and other monoclonal anti-CD20 antibodies for chronic lymphocytic leukaemia (Review)," Cochrane Database of Systematic Reviews, Issue 11, 125 pages (copyright 2012).
Baumgartner et al., "Melanoma induces immunosuppression by up-regulating FOXP3(+) regulatory T cells", J Surg Res., 2007, 141(1): 72-77.
Belani et al., "Multicenter, randomized trial for stage IIIB or IV non-small-cell lung cancer using weekly paclitaxel and carboplatin followed by maintenance weekly paclitaxel or observation", J. Clin. Oncol., 2003, 21:2933-2939.
Bird et al., "Single-chain antigen-binding proteins", Science, Oct. 1988, 242(4877), pp. 423-426.
Boasberg et al., "Phase II trial of nab-paclitaxel and bevacizumab as first-line therapy in patients with unresectable melanoma", Journal of Clinical Oncology, May 20, 2011, vol. 29, No. 15 Supp, 8543.
Boasberg et al., Nab-paclitaxel and bevacizumab as first-line therapy in patients with unresectable stage III and IV melanoma, J Clin Oncol., 27:15s, 2009 (suppl; abstr 9061), 2009 ASCO Annual Meeting, Retrieved from the Internet: <URL: http://meetinglibrary.asco.org/print/584876>, 2 pages, 2009.
Bolstad et al., "A comparison of normalization methods for high density oligonucleotide array data based on variance and bias", Bioinformatics, 2003, 19:185-193.
Cao et al., "Response of resistant melanoma to a combination of weekly paclitaxel and bevacizumab", Clin Transl Oncol, 2007, 9:119-120.
Carson et al., "A phase 2 trial of a recombinant humanized monoclonal anti-vascular endothelial growth factor (VEGF) antibody in patients with malignant melanoma", Proc. Am. Soc. Clin. Oncol. 22: Abstract 2873 (2003).
Carson et al., "A phase 2 trial of a recombinant humanized monoclonal anti-vascular endothelial growth factor (VEGF) antibody in patients with malignant melanoma", Proceedings of the ASCO vol. 22, No. 2873, General Poster Session, Thirty-Ninth Annual Meeting of the American Society of Clinical Oncology, May 31-Jun. 3, 2003, Chicago, IL, 2 pages.

(56) References Cited

OTHER PUBLICATIONS

Celis, "Overlapping human leukocyte antigen class I/II binding peptide vaccine for the treatment of patients with stage IV melanoma: evidence of systemic immune dysfunction", Cancer, 2007, 110(1):203-214.
Chapman et al., "Improved Survival with Vemurafenib in Melanoma with BRAF V600E Mutation", The New England Journal of Medicine, Jun. 30, 2011, vol. 364, Issue 26, pp. 2507-2516.
Chisholm et al., "Response to influenza immunization during treatment for cancer", Arch Dis Child, 2001, 84(6):496-500.
Chong et al., "Combining cancer vaccines with chemotherapy", Expert Opin Pharmacother., 2006, 6(16):2813-2820.
Cleland et al., "The Development of Stable Protein Formulations: A close look at protein aggregation, deamidation, and oxidation", Therapeutic Drug Carrier Systems, 1993, 10(4), pp. 307-377.
Davis, "Affinity separation of antibody-toxin conjugate from albumin-stabilized formulation", Am Biotechnol Lab., 12(4):60-64, Mar. 1994.
Degrasse, J.A., "A Single-Stranded DNA Aptamer That Selectively Binds to *Staphylococcus aureus* Enterotoxin B", PLoS One, 2012, 7(3) e33410, pp. 1-7.
Deguchi et al., "Effect of Methotrexate-Monoclonal Anti-Prostatic Acid Phosphatase Antibody Conjugate on Human Prostate Tumor", Cancer Research, Aug. 1986, 46, pp. 3751-3755.
Demirkesen et al., "The correlation of angiogenesis with metastasis in primary cutaneous melanoma: a comparative analysis of microvessel density, expression of vascular endothelial growth factor and basic fibroblastic growth factor", Pathology, 2006, 38:132-137.
Denardo et al., "Inflammation and breast cancer. Balancing immune response: crosstalk between adaptive and innate immune cells during breast cancer progression", Breast Cancer Res., 2007, 9(4):212.
Desai et. al., "Increased antitumor activity, intratumor paclitaxel concentrations, and endothelial cell transport of cremophor-free, albumin-bound paclitaxel, ABI-007, compared with cremophor-based paclitaxel", Clin Cancer Res., 2006, 12(4): 1317-24.
Deweers et al., "Daratumumab, a novel therapeutic human CD38 monoclonal antibody, induces killing of multiple myeloma and other hematological tumors", J. Immunol., 186(3): 1840-1848, Feb. 1, 2011.
Dudek et al., "Autologous large multivalent immunogen vaccine in patients with metastatic melanoma and renal cell carcinoma", Am. J. Clin. Oncol., Apr. 1, 2008, 31(2):173-181.
Elbayoumi et al., "Tumor-Targeted Nanomedicines: Enhanced Antitumor Efficacy In vivo of Doxorubicin-Loaded, Long-Circulating Liposomes Modified with Cancer-Specific Monoclonal Antibody", Clin Cancer Res., 2009, 15(6):1973-1980.
Ellyard et al., "Th2-mediated anti-tumour immunity: friend or foe?", Tissue Antigens, 2007, 70(1):1-11.
Elsadek et al., "Impact of albumin on drug delivery—New applications on the horizon", J of Controlled Release, 2011, 1-25.
Ferrara et al., "The biology of VEGF and its receptors", Nat. Med., 2003, 9:669-676.
Flaherty et al., "Final Results of E2603: a double-blind, randomized phase III trial comparing carboplatin (C)/paclitaxel(P) with or without sorafenib(S) in metastatic melanoma", J. Clin Oncol., 2010, 28:15s (suppl: abstr 8511).
Folkman, J., "Angiogenesis in cancer, vascular, rheumatoid and other disease", Nat. Med., 1995, 1, 27-31.
Fricke et al., "Vascular endothelial growth factor-trap overcomes defects in dendritic cell differentiation but does not improve antigen-specific immune responses", Clin. Cancer Res., 2007, 13:4840-4848.
Gabrilovich et al., "Production of vascular endothelial growth factor by human tumors inhibits the functional maturation of dendritic cells", Nat. Med., 1996, 2: 1096-1103.
Gao et al., "In vivo cancer targeting and imaging with semiconductor quantum dots", Nat Biotech, 2004, 22(8):969-976.
Gogas et al., "Chemotherapy for metastatic melanoma: time for a change?", Cancer, 2007, 109(3): 455-464.
Graells et al., "Overproduction of VEGF16s concomitantly expressed with its receptors promotes growth and survival of melanoma cells through MAPK and PI3K signaling", J. Invest. Dermatol., 2004, 123:1151-1161.
Gupta, I., et al., "Ofatumumab, the first human anti-CD20 monoclonal antibody for the treatment of B cell hematologic malignancies," Ann. N.Y. Acad. Sci., 1263, pp. 43-56 (Jul. 25, 2012).
Haley et al., "Nanoparticles for drug delivery in cancer treatment", Urol. Oncol.: Seminars and Original Invest., 2008, 26:57-64.
Hauschild et al., "Individualized therapy of disseminated cancer using malignant melanoma as a model", Cancer and Metastasis Reviews, 2006, 25(2): 253-256.
Hauschild et al., "Results of a Phase III, Randomized, Placebo-Controlled Study of Sorafenib in Combination with Carboplatin and Paclitaxel as Second-Line Treatment in Patients with Unresectable Stage III or Stage IV Melanoma", Journal of Clinical Oncology, Jun. 10, 2009, vol. 27, No. 17, pp. 2823-2830.
Hersh et al., "A Phase 2 Clinical Trial of nab-Paclitaxel in Previously Treated and Chemotherapy-Naïve Patients With Metastatic Melanoma", Cancer, Jan. 1, 2010, 116:155, pp. 155-163.
Hersh et al., "A randomized, controlled phase III trial of nab-Paclitaxel versus dacarbazine in chemotherapy-naïve patients with metastatic melanoma", Ann Oncol, 2015, epub Sep. 26, 2015.
Hersh et al., "Open-label, multicenter, phase II trial of ABI-007 in previously treated and previously untreated patients with metastatic malignant melanoma", J. Clin. Oncol., 2005, 23(165):7558 (Abstract).
Hobbs et al., "Regulation of Transport pathways in tumor vessels: role of tumor type and microenvironment", Proc Natl Acad Sci USA, Apr. 1998, 95, pp. 4607-4612.
Hodi et al., "Improved survival with ipilimumab in patients with metastatic melanoma", The New England Journal of Medicine, Aug. 19, 2010, vol. 363, No. 8, pp. 711-723.
Hodi et al., "Phase II study of paclitaxel and carboplatin for malignant melanoma", Am. J. Clin. Oncol., 2002, 25:283-286.
Huncharek et al., "Single-agent DTIC versus combination chemotherapy with or without immunotherapy in metastatic melanoma: a meta-analysis of 3273 patients from 20 randomized trials", Melanoma Research, 11:75-81 (2001).
Hunkapiller et al., "Immunology: The growing immunoglobulin gene superfamily", Nature, Sep. 1986, 323, pp. 15-16.
Huston et al., "Protein engineering of antibody binding sites: Recovery of specific activity in an antidigoxin single-chain Fv analogue produced in *Escherichia coli*", Proc. Natl. Acad. Sci. USA, Aug. 1988, vol. 85, pp. 5879-5883.
Ibrahim et al., "Phase I and Pharmacokinetic Study of ABI-007, a Cremophor-free, Protein-stabilized, Nanoparticle Formulation of Paclitaxel", Clinical Cancer Research, May 2002, vol. 8, pp. 1038-1044.
Inagaki et al., "Clinical significance of serum Th1-, Th2- and regulatory T cells-associated cytokines in adult T-cell leukemia/lymphoma: High interleukin-5 and -10 levels are significant unfavorable prognostic factors", Int. J. Cancer, 2006, 118(12):3054-3061.
International Preliminary Report on Patentability for Application No. PCT/US2012/037137 dated Nov. 12, 2013, 5 pages.
International Preliminary Report on Patentability for Application No. PCT/US2008/057025, dated Sep. 15, 2009, 6 pages.
International Preliminary Report on Patentability for Application No. PCT/US2009/049511, dated Jan. 5, 2011, 6 pages.
International Preliminary Report on Patentability for Application No. PCT/US2013/062638, dated Apr. 16, 2015, 11 pages.
International Preliminary Report on Patentability, PCT/US2015/035505, Mayo Foundation for Medical Education and Research, 10 pages (dated Dec. 22, 2016).
International Preliminary Report on Patentability, PCT/US2015/035515, Mayo Foundation for Medical Education and Research, 18 pages (dated Dec. 29, 2016).
International Search Report and Written Opinion for Application No. PCT/US15/35505 dated Nov. 24, 2015. 17 pages.
International Search Report and Written Opinion for Application No. PCT/US15/35515 dated Sep. 21, 2015. 23 pages.
International Search Report and Written Opinion for Application No. PCT/US16/47641 dated Oct. 31, 2016, 11 pages.

(56) References Cited

OTHER PUBLICATIONS

International Search Report and Written Opinion for Application No. PCT/US2008/057025, dated Jul. 1, 2008, 11 pages.
International Search Report and Written Opinion for Application No. PCT/US2009/049511, dated Feb. 2, 2010, 8 pages.
International Search Report and Written Opinion for Application No. PCT/US2012/037137 dated Sep. 28, 2012, 5 pages.
International Search Report and Written Opinion for Application No. PCT/US2013/062638, dated Jan. 23, 2014, 19 pages.
International Search Report and Written Opinion for Application No. PCT/US2015/054295 dated Jan. 25, 2016, 15 pages.
Jain et al., "Delivering nanomedicine to solid tumors", Nature Reviews Clinical Oncology, Nov. 2010, 7, pp. 653-664.
Jazirehi et al., "Rituximab (anti-CD20) selectively modifies Bcl-xl and apoptosis protease activating factor-1 (APAF-1) expression and sensitizes human non-Hodgkin's lymphoma B cell lines to paclitaxel-induced apoptosis," Mol. Cancer Ther., (2003), 2:1183-1193.
Jiang et al., "Regulation of Immune Responses by T Cells", N Engl J Med., 2006, 354(11): 1166-1176.
Julien et al, "Utilization of monoclonal antibody-targeted nanomaterials in the treatment of cancer", 2011, MAbs, 3:467-478.
Kamat et al., "Metronomic chemotherapy enhances the efficacy of antivascular therapy in ovarian cancer", Cancer Res., 2007, 67(1):281-288.
Kawai et al., "VEGF121 promotes lymphangiogenesis in the sentinel lymph nodes of non-small cell lung carcinoma patients", Lung Cancer, 2008, 59(1):41-47.
Kikuchi et al., "Vascular endothelial growth factor and dendritic cells in human squamous cell carcinoma of the oral cavity", Anticancer Res., 2006, 26(3A):1833-1848.
Kim et al., "A Dual Target-directed Agent against Interleukin-6 Receptor and Tumor Necrosis Factor a ameliorates experimental arthritis", Scientific Reports, 2016, pp. 1-12.
Kim et al., "BEAM: A Randomized Phase II Study Evaluating the Activity of Bevacizumab in Combination with Carboplatin Plus Paclitaxel in Patients With Previously Untreated Advanced Melanoma", Journal of Clinical Oncology: official journal of the American Society of Clinical Oncology, Jan. 1, 2012, vol. 30, No. 1, pp. 34-41.
Kirkwood et al., "A pooled analysis of eastern cooperative oncology group and intergroup trials of adjuvant high-dose interferon for melanoma", Clin Cancer Res., 2004, 10(5):1670-1677.
Kondejewski et al., "Synthesis and characterization of carbohydrate-linked murine monoclonal antibody K20-human serum albumin conjugates", Bioconjug Chem., 5(6):602-611, Nov.-Dec. 1994.
Korman et al., "Tumor immunotherapy: preclinical and clinical activity of anti-CTLA4 antibodies", Curt Opin Invest Drugs, 2005, 6(6):582-591.
Kottschade et al., "A Phase II Trial of Nab-Paclitaxel (ABI-007) and Carboplatin in Patients with Unresectable Stage IV Melanoma", Cancer, Apr. 15, 2011, 117(8), pp. 1704-1710.
Kottschade et al., "A Randomized Phase 2 Study of Temozolomide and Bevacizumab or nab-Paclitaxel, Carboplatin, and Bevacizumab in Patients with Unresectable Stage IV Melanoma", Cancer, 2013, vol. 119, Issue 3, pp. 586-592.
Kratz et al., "Serum proteins as drug carriers of anticancer agents: a review", Drug Deliv., 5(4):281-299, 1998.
Kratz, "Albumin as a drug carrier: design of prodrugs, drug conjugates and nanoparticles", J Control Release, 132(3):171-183, Epub May 17, 2008.
Krishnan et al., "Programmed death-1 receptor and interleukin-10 in liver transplant recipients at high risk for late cytomegalovirus disease", Transpl Infect Dis., 12(4):363-70, print Aug. 2010, ePub Jan. 2010.
Kukowska-Latallo et al., Nanoparticle Targeting of Anticancer Drug Improves Therapeutic Response in Animal Model of Human Epithelial Cancer, Cancer Res, 2005, 65(12):5317-5324.
Kumar et al., Th1/Th2 cytokine imbalance in meningioma, anaplastic astrocytoma and glioblastoma multiforme patients, Oncol. Rep., 2006, 15(6):1513-1516.

Lanzavecchia et al., "The use of hybrid hybridomas to target human cytotoxic T lymphocytes", Eur. J. Immunol., 1987, 17, pp. 105-111.
Lau et al., Is inhibition of cancer angiogenesis and growth by paclitaxel schedule dependent?, Anti-Cancer Drugs, 2004, 15:871-875.
Lei et al., Comparing cellular uptake and cytotoxicity of targeted drug carriers in cancer cell lines with different drug resistance mechanisms, Nanomed: Nanotech, Biol, and Med., 2011, 7:324-332.
Lev et al., Dacarbazine causes transcriptional up-regulation of interleukin 8 and vascular endothelial growth factor in melanoma cells: a possible escape mechanism from chemotherapy, Mol. Cancer Ther., 2003, 2:753-763.
Lev et al., Exposure of melanoma cells to dacarbazine results in enhanced tumor growth and metastasis in vivo, J. Clin. Oncol., 2004, 22:2092-2100.
Lin, S.Y, "Salmon calcitonin: conformational changes and stabilizer effects", AIMS Biophysics, 2015, 2(4): 695-723.
Marcoval et al., Angiogenesis and malignant melanoma. Angiogenesis is related to the development of vertical (tumorigenic) growth phase, J. Cutan. Pathol., 1997, 24:212-218.
Markovic et al., A phase II study of ABT-510 (thrombospondin-1 analog) for the treatment of metastatic melanoma, Am. J. Clin. Oncol., 2007, 30(3):303-309.
Markovic et al., A reproducible method for the enumeration of functional ( cytokine producing) versus non-functional peptide-specific cytotoxic T lymphocytes in human peripheral blood, Clin. Exo. Immunol., 2006, 145:438-447.
Markovic et al., Peptide vaccination of patients with metastatic melanoma: improved clinical outcome in patients demonstrating effective immunization, Am J Clin Oncol., 2006, 29(4):352-360.
Matejtschuk, P., "Lyophilization of Proteins", Methods in Molecular Biology, Cryopreservation and Freeze-Drying Protocols, Second Edition, Edited by: J. G. Day and G. N. Stacey © Humana Press Inc., Totowa, NJ, 2007, vol. 368, pp. 59-72.
Matsuda et al., Preoperative oral immune-enhancing nutritional supplementation corrects TH1/TH2 imbalance in patients undergoing elective surgery for colorectal cancer, Dis. Colon Rectum, 2006, 49(4):507-516.
Mayo Clinic: Paclitaxel Albumin-Stabilized Nanoparticle Formulation and Bevacizumab in Treating Patients With Stage IV Melanoma That Cannot Be Removed by Surgery—Full Text View ClinicalTrials.gov, Dec. 19, 2013, pp. 1-4, Retrieved from the Internet URL:https//clinicaltrials.gov/ct2/show/NCT02020707?term=targeted+nanoparticle+therapy+for+advanced+melanoma&rank=1 [retrieved on Jan. 6, 2016].
McElroy et al., Imaging of Primary and Metastatic Pancreatic Cancer Using a Fluorophore-Conjugated Anti-CA19-9 Antibody for Surgical Navigation, World J Surg., 2008, 32: 1057-1066.
Melcher, Recommendations for influenza and pneumococcal vaccinations in people receiving chemotherapy, Clin Oncol (R Coll Radiol), 2005, 17(1): 12-15.
Merchan et al., Increased endothelial uptake of paclitaxel as a potential mechanism for its antiangiogenic effects: potentiation by Cox-2 inhibition, Int. J. Cancer, 2005, 113, pp. 490-498.
Mezzaroba et al., "New potential therapeutic approach for the treatment of B-Cell malignancies using chlorambucil/Hydroxychloroquine-Loaded Anti-CD20 Nanoparticles", September 2103, PLoS ONE vol. No. 8, Issue 9 pp. 1-10, e74216.
Middleton et al., Randomized phase III study of temozolomide versus dacarbazine in the treatment of patients with advanced metastatic malignant melanoma, J. Clin. Oncol., 2000, 18, pp. 158-166.
Miller et al. "Paclitaxel plus Bevacizumab versus Paclitaxel Alone for Metastatic Breast Cancer," N Engl. J Med., (2007) vol. 357:2666-2676.
Mimura et al., Vascular endothelial growth factor inhibits the function of human mature dendritic cells mediated by VEGF receptor-2, Cancer Immunol Immunother., 2007, 56(6). pp. 761-770.
Mirtsching et al., "A Phase II Study of Weekly Nanoparticle Albumin-Bound Paclitaxel With or Without Trastuzumab in Metastatic Breast Cancer", Clinical Breast Cancer, 2011, 11(2):121-128.

(56) References Cited

OTHER PUBLICATIONS

Mocellin et al., Cytokines and immune response in the tumor microenvironment, J Immunother., 2001, 24(5), pp. 392-407.
Motl, S., Bevacizumab in combination chemotherapy for colorectal and other cancers, Am. J. Health-Syst. Pharm 2005, 62:1021-1032.
Ng et al., Influence of formulation vehicle on metronomic taxane chemotherapy: albumin-bound versus cremophor EL-based paclitaxel, Clin. Cancer Res., 2006, 12, pp. 4331-4338.
Ng et al., Taxane-mediated antiangiogenesis in vitro: influence of formulation vehicles and binding proteins, Cancer Res., 2004, 64, pp. 821-824.
Nilvebrant et al., "The Albumin-Binding Domain as a Scaffold for Protein Engineering", Computational and Structural Biotechnology Journal, Mar. 2013, vol. 6, Issue 7, e201303099, http://dx.doi.org/10.5936/csbj.201303099.
Oku et al., Tumor growth modulation by sense and antisense vascular endothelial growth factor gene expression: effects on angiogenesis, vascular permeability, blood volume, blood flow, fluorodeoxyglucose uptake, and proliferation of human melanoma intracerebral xenografts, Cancer Res., 1998, 58, pp. 4185-4192.
Parikh et al., The vascular endothelial growth factor family and its receptors, Hematol. Oncol. Clin. N. Am., 2004, 18, pp. 951-971.
Park et al., Anti-HER2 Immunoliposomes: Enhanced Efficacy Attributable to Targeted Delivery, Clin. Cancer Res., 2002, 8, pp. 1172-1181.
Perez et al., "Phase 2 trial of carboplatin, weekly paclitaxel, and biweekly bevacizumab in patients with unresectable stage IV melanoma," A north central cancer treatment group study, Cancer, 2009, 115(1), pp. 119-127.
Phase II: A Study of Bevacizumab With Carboplatin and Paclitaxel Chemotherapy for the First-Line Treatment of Patients With Metastatic Melanoma (BEAM) Mar. 12, 2007, [retrieved Mar. 15, 2010]. Retrieved from the Internet: <URL:http://clinicaltrials.gov/archive/NCT00434252/2007 03 12>, 3 pages.
Pikal, M., Freeze-drying of proteins, Part II: Formulation selection, Biopharm, 1990, 9, pp. 26-30.
Polak et al., Mechanisms of local immunosuppression in cutaneous melanoma, Br J Cancer, 2007, 96(12), pp. 1879-1887.
Porrata et al., Early lymphocyte recovery predicts superior survival after autologous hematopoietic stem cell transplantation in multiple myeloma or non-Hodgkin lymphoma, Blood, 2001, 98(3), pp. 579-585.
Porrata et al., Timely reconstitution of immune competence affects clinical outcome following autologous stem cell transplantation, Clin Exp Med., 2004, 4(2):78-85.
Powell et al., Adoptive transfer of vaccine-induced peripheral blood mononuclear cells to patients with metastatic melanoma following lymphodepletion, J Immunol., 2006, 177(9), pp. 6527-6539.
Pries et al., Cytokines in head and neck cancer, Cytokine Growth Factor Rev., 2006, 17(3), pp. 141-146.
Ranieri et al., "Vascular endothelial growth factor (VEGF) as a target of bevacizumab in cancer: from the biology to the clinic", Curr. Med. Chem., 2006, 13, 1845-1857.
Rao et al., "Combination of paclitaxel and carboplatin as second-line therapy for patients with metastatic melanoma", Cancer, 2006, 106(2), 375-382.
Ribas et al., "Antitumor activity in melanoma and anti-self responses in a phase I trial with the anti-cytotoxic T lymphocyte-associated antigen 4 monoclonal antibody CP-675,206", J Clin Oncol., Dec. 10, 2005, 23(35), pp. 8968-8977.
Rosenberg et al., "Tumor progression can occur despite the induction of very high levels of self/tumor antigen-specific CD8+ T cells in patients with melanoma", J. Immunol., 2005, 175(9), pp. 6169-6176.
Roy et al., "Tumor associated release of interleukin-10 alters the prolactin receptor and down regulates prolactin responsiveness of immature cortical thymocytes", J Neuroimmunol., 2007, 186(1-2), pp. 112-120.

Rudnicka et al., "Rituximab causes a polarization of B cells that augments its therapeutic function in NK-cell-mediated antibody-dependent cellular cytotoxicity", Blood, 2013, 121(23):4694-4702.
Sadat et al., "Nano-pharmaceutical Formulations for Targeted Drug Delivery against HER2 in Breast Cancer", Current Cancer Drug Targets, 2015, 15(1):71-86.
Salven et al., "Enhanced expression of vascular endothelial growth factor in metastatic melanoma", Br. J. Cancer, 1997, 76(7), pp. 930-934.
Sandler et al., "Paclitaxel-carboplatin alone or with bevacizumab for non-small-cell lung cancer", N. Engl. J. Med., 2006, 355:2542-2550.
Sato et al., "Intraepithelial CD8+ tumor-infiltrating lymphocytes and a high CD8+/regulatory T cell ratio are associated with favorable prognosis in ovarian cancer", Proc Natl Acad Sci USA, 2005, 102(51):18538-18543.
Schrama et al., "Antibody targeted drugs as cancer therapeutics, Nature Reviews Drug Discovery", Feb. 2006, 5, pp. 147-159.
Sester et al., "Differences in CMV-specific T-cell levels and long-term susceptibility to CMV infection after kidney, heart and lung transplantation", Am J Transplant., 5(6):1483-1489, Jun. 2005.
Srivastava et al., "Angiogenesis in cutaneous melanoma: pathogenesis and clinical implications", Microsc. Res. Tech., 2003, 60:208-224.
Streit et al., "Angiogenesis, lymphangiogenesis, and melanoma metastasis", Oncogene, 2003, 22, pp. 3172-3179.
Taieb et al., "Chemoimmunotherapy of tumors: Cyclophosphamide synergtizes with exosome based vaccines", J. Immunol., Mar. 1, 2006, 176(5):2722-2729.
Tao et al., "Inhibiting the growth of malignant melanoma by blocking the expression of vascular endothelial growth factor using an RNA interference approach", Br. J. Dermatol., 2005, 153:715-724.
Tas et al., "Circulating serum levels of angiogenic factors and vascular endothelial growth factor receptors 1 and 2 in melanoma patients", Melanoma Res., 2006, 16:405-411.
Terheyden et al., "Anti-vascular endothelial growth factor antibody bevacizumab in conjunction with chemotherapy in metastasizing melanoma", J Cancer Res Clin Oncol, 2007, 133(11), pp. 897-901.
Ugurel et al., "Increased serum concentration of angiogenic factors in malignant melanoma patients correlates with tumor progression and survival", J. Clin. Oncol., 2001, 19:577-583.
Vacca et al., "Docetaxel versus paclitaxel for antiangiogenesis", J. Hematother. Stem Cell Res., 2002, 11:103-118.
Varker et al., "A randomized phase 2 trial of bevacizumab with or without daily low-dose interferon alfa-2b in metastatic malignant melanoma", Ann Surg Oncol., 14(8):2367-2376, print Aug. 2007, Epub May 2007.
Vence et al., "Circulating tumor antigen-specific regulatory T cells in patients with metastatic melanoma", Proc Natl Acad Sci USA, 2007, 104(52), pp. 20884-20889.
Wagner et al., "Enhanced drug targeting by attachment of an anti alphav integrin antibody to doxorubicin loaded human serum albumin nanoparticles", Biomaterials., 31(8):2388-2398, Epub Dec. 23, 2009.
Walker et al., "Monitoring immune responses in cancer patients receiving tumor vaccines", Int Rev Immunol., 2003, 22(3-4):283-319.
Wang et al., "Biofunctionalized targeted nanoparticles for therapeutic applications", Expert Opin. Biol. Ther., 2008, 8(8): 1063-1070.
Wang et al., "Paclitaxel at ultra low concentrations inhibits angiogenesis without affecting cellular microtubule assembly", Anti-Cancer Drugs, 2003, vol. 14, Issue 1, pp. 13-19.
Weber, "Review: anti-CTLA-4 antibody ipilimumab: case studies of clinical response and immune-related adverse events", Oncologist, Jul. 2007, 12(7), pp. 864-872.
Wiernik et al., "Phase I trial of taxol given as a 24-hour infusion every 21 days: responses observed in metastatic melanoma", Journal of Clinical Oncology, Aug. 1987, vol. 5, No. 8, pp. 1232-1239.
Wong et al., "Programmed death-1 blockade enhances expansion and functional capacity of human melanoma antigen-specific CTLs", Int. Immunol., 2007, vol. 19, No. 10, pp. 1223-1234.

(56) References Cited

OTHER PUBLICATIONS

Wu et al., "Aptamers: Active Targeting Ligands for Cancer Diagnosis and Therapy", Theranostics, 2015, 5(4):322-344.
Yardley et al., "A pilot study of adjuvant nanoparticle albumin-bound (nab) paclitaxel and cyclophosphamide, with trastuzumab in HER2-positive patients, in the treatment of early-stage breast cancer", Breast Cancer Res Treat, 2010, 123:471-475.
Yee et al., "Adoptive T cell therapy using antigen-specific CD8+ T cell clones for the treatment of patients with metastatic melanoma: in vivo persistence, migration, and antitumor effect of transferred T cells", Proc Natl Acad Sci USA, 2002, 99(25):16168-16173.
Yuan et al., "Vascular Permeability in a Human Tumor Xenograft: Molecular Size Dependence and Cutoff Size", Cancer Research, Sep. 1, 1995, 55, pp. 3752-3756.
Zimpfer-Rechner et al., "Randomized phase II study of weekly paclitaxel versus paclitaxel and carboplatin as second-line therapy in disseminated melanoma: a multicentre trial of the Dermatologic Co-operative Oncology Group (DeCOG)", Melanoma Res., 2003, 13:531-536.
Adams et al., "(P2-11-01) Safety and clinical activity of atezolizumab (anti-PDL1) in combination with nab-paclitaxel in patients with metastatic triple-negative breast cancer", 2015, XP002775314, 2015 San Antonio Breast Cancer Symposlum, URL: http://sabcs.org/portals/sabcs2016/documents/sabcs-2015-abstracts.pdf?v=5.
Adams et al., "Phase Ib trial of atezolizumab in combinaton with nab-paclitaxel in patients with metastatic triple-negative breast cancer (mTNBC)" Journal of Clinical Oncology col. 34, No. 15, May 1, 2016, 4 pages.
Anonymous, "A Phase III, Multicenter, Placebo-Controlled Study of Atezolizumab (Anti-PD-L1 Antibody) in Combination with Nab Paclitaxel Compared with Placebo with Nab Paclitaxel for Patients with Previously Untreated Metastatic Triple Negative Breast Cancer", ClinicalTrials.gov, Apr. 21, 2015, 1 page.
Anonymous, "Atezolizumab Plus Abraane Promising New Treatment for Triple-Negative Breast Cancer", Comprehensive Cancer Center, Jan. 7, 2015, pp. 1-2.
U.S. Appl. No. 14/116,619, office action dated Feb. 4, 2015.
U.S. Appl. No. 14/116,619, office action dated Apr. 28, 2016.
U.S. Appl. No. 14/116,619, office action dated Sep. 10, 2015.
U.S. Appl. No. 14/432,979, office action dated May 16, 2018.
U.S. Appl. No. 14/432,979, office action dated Jun. 30, 2016.
U.S. Appl. No. 14/432,979, office action dated Oct. 4, 2017.
U.S. Appl. No. 14/432,979, office action dated Dec. 15, 2016.
U.S. Appl. No. 14/882,327, office action dated May 2, 2016.
U.S. Appl. No. 15/030,567, office action dated Sep. 7, 2016.
U.S. Appl. No. 15/030,568, office action dated May 25, 2017.
U.S. Appl. No. 15/030,568, office action dated Jun. 18, 2018.
U.S. Appl. No. 15/030,568, office action dated Dec. 1, 2017.
U.S. Appl. No. 15/052,336, office action dated Feb. 9, 2018.
U.S. Appl. No. 15/052,336, office action dated Sep. 4, 2018.
U.S. Appl. No. 15/052,623, office action dated Feb. 9, 2018.
U.S. Appl. No. 15/052,623, office action dated May 19, 2017.
U.S. Appl. No. 15/052,623, office action dated Jul. 9, 2018.
U.S. Appl. No. 15/052,623, office action dated Nov. 25, 2016.
U.S. Appl. No. 15/060,967, office action dated Aug. 2, 2016.
U.S. Appl. No. 15/064,396, office action dated Aug. 9, 2016.
U.S. Appl. No. 15/092,403, office action dated Apr. 2, 2018.
U.S. Appl. No. 15/092,403, office action dated Oct. 4, 2018.
U.S. Appl. No. 15/092,433, office action dated Mar. 21, 2018.
U.S. Appl. No. 15/092,433, office action dated Aug. 10, 2018.
U.S. Appl. No. 15/092,433, office action dated Oct. 11, 2017.
U.S. Appl. No. 15/187,672, office action dated May 31, 2018.
U.S. Appl. No. 15/202,115, office action dated Jan. 20, 2017.
U.S. Appl. No. 15/202,115, office action dated Sep. 26, 2016.
U.S. Appl. No. 15/225,428, office action dated Aug. 14, 2018.
U.S. Appl. No. 15/225,428, office action dated Dec. 20, 2017.
U.S. Appl. No. 15/225,504, office action dated Apr. 4, 2017.
U.S. Appl. No. 15/225,504, office action dated Aug. 1, 2018.
U.S. Appl. No. 15/225,504, office action dated Nov. 9, 2016.
U.S. Appl. No. 15/225,542, office action dated Apr. 4, 2017.
U.S. Appl. No. 15/225,542, office action dated Nov. 22, 2016.
U.S. Appl. No. 15/286,006, office action dated Jan. 9, 2017.
U.S. Appl. No. 15/286,006, office action dated Jan. 18, 2018.
U.S. Appl. No. 15/286,006, office action dated May 16, 2017.
U.S. Appl. No. 15/286,024, office action dated Jan. 6, 2017.
U.S. Appl. No. 15/286,024, office action dated May 19, 2017.
U.S. Appl. No. 15/359,569, office action dated Feb. 22, 2017.
U.S. Appl. No. 15/359,569, office action dated Jun. 23, 2017.
U.S. Appl. No. 15/359,569, office action dated Jul. 12, 2018.
U.S. Appl. No. 15/412,554, office action dated Sep. 27, 2018.
U.S. Appl. No. 15/412,564, office action dated Jul. 10, 2018.
U.S. Appl. No. 15/412,596, office action dated Sep. 4, 2018.
U.S. Appl. No. 15/412,610, office action dated Jul. 9, 2018.
U.S. Appl. No. 15/452,669, office action dated May 5, 2017.
U.S. Appl. No. 15/452,669, office action dated Nov. 16, 2017.
Armitage et al., "New apparoach to classifying non-Hodgkin's lymphomas: clinical features of the major histologic subtypes. Non-Hodgkin's Lymphoma Classification Project" J Clin Oncol 16, 2780-2795 (1998).
Baba, Oleo Science 10(1):15-18 (Jan. 2010).
Colman, "Effects of amino acid sequence changes on antibody-antigen interactions," Research in Immunology (145(1)33-36, (1994).
Desai et al., "Enhanced antitumor activity and safety of albumin-bound nab-docetaxel versus polysorbate 80-based docetaxel", Eur. J. Cancer, Suppl.; 18th Symposium on molecular targets and cancer therapeutics, Prague, Czech Republic; Nov. 7-10, 2006, vol. 4, No. 12, Nov. 2006 (Nov. 2006), p. 49.
Edison, "MorphoSys," 16 pages (Aug. 8, 2013).
Emens et al.: "(OT1-01-06) A phase III randomized trial of atezolizumab in combination with nab-paclitaxel, as firs tline therapy for patienst with metastatic triple-negative breast cancer (mTNBC)", 2015, XP002775318, 2015 San Antonio Breast Cancer Symposium, URL: http://sabcs.org/portals/sabcs2016/documents/sabcs-2015-abstracts.pdf?v=5.
European Application No. 08743903.0, Extended European Search Report dated Jan. 24, 2011.
European Application No. 09774506.1, Extended European Search Report dated Mar. 22, 2012.
European Application No. 12781802.9, Extended European Search Report dated Dec. 18, 2014.
European Application No. 13843209.1, Extended European Search Report Application No. 13843209.1, dated Sep. 5, 2016.
European Applicabon No. 15806443.6, Extended European Search Report dated Dec. 11, 2017.
European Application No. 15809075.3, Extended European Search Report dated Dec. 21, 2017.
Fabi et al, "Prospective study on nanoparticle albumin-bound paclitaae in advanced breast cancer: clinical results and biological observations in taxane-pretreated patients", Drug Design, Development and Therapy vol. 9, Nov. 1, 2015, 7 pages.
Flores et al, "Novel oral taxane therapies: recent Phase I results", Clin. Invest. vol. 3, No. 4, Apr. 1, 2013 (Apr. 1, 2013), pp. 333-341, XP055426571, UK, ISSN: 2041-6792, DOI: 10.4155/cli.13.18.
Golay et al., "Mechanism of action of therapeutic monoclonal antibodies: promises and pitfalls of in vitro and in vivo assay," Arch. Biochem. Biophys. 526(2):146-153 (2012).
Hamilton et al. "Nab-Paclitaxel/Bevacizumab/Carboplatin Chemotherapy in First-Line Triple Negative Metastatic Breast Cancer", Clinical Breast Cancer, vol. 13, No. 6, Dec. 1, 2013, 6 pages.
Hara, "What is anti-HER2 antibody tubulin polymerization inhibitor complex T-DM1?," Pharm. Monthly 56(5):734-739 (May 2014).
Harlow et al., Antibodies: A Laboratory Manual, Cold Spring Harbor Laboratory, New York, 1988 (9 pages).
Hassan et al: "Comparison of Different Crosslinking Methods for Preparation of Docetaxel-loaded Albumin Nanoparticles", Iranian Journal of Pharmaceutical Research, vol. 14, No. 2, Apr. 2015 (Apr. 2015), pp. 385-394.
Hegde et al. "Predictive Impact of Circulating Vascular Endothelial Growth Factor in Four Phase III Trials Evaluating Bevacizumab," Clinical Cancer Research, Feb. 15, 2013 (Feb. 15, 2013) vol. 19, pp. 929-937.
Hood et al., Immunology, 1984, Benjamin, N.Y., 2nd Edition.

(56) References Cited

OTHER PUBLICATIONS

Inman, "Atezolizumab/Nab-Paclitaxel Combo Shows High Response Rates in TNBC", OneLive, Dec. 10, 2015, 4 pages.
International Preliminary Report on Patentability for Application No. PCT/US2015/054295 dated Oct. 13, 2016.
International Preliminary Report on Patentability for Application PCT/US2016/026267, dated Apr. 10, 2018.
International Preliminary Report on Patentability for Application PCT/US2017/017553, dated Aug. 23, 2018.
International Search Report and Written Opinion for Application No. PCT/US2016/026267, dated Jul. 12, 2016.
International Search Report and Written Opinion for Application No. PCT/US2016/026270, dated Oct. 12, 2017.
International Search Report and Written Opinion for Application No. PCT/US2017/012580, dated Mar. 17, 2017.
International Search Report and Written Opinion for Application No. PCT/US2017/045643, dated Oct. 25, 2017.
International Search Report and Written Opinion for Application No. PCT/US2017/049745, dated Dec. 15, 2017.
International Search Report and Written Opinion for Application No. PCT/US2017/049746, dated Nov. 27, 2017.
International Search Report and Written Opinion for Application No. PCT/US2017/050134, dated Nov. 16, 2017.
International Search Report and Written Opinion for Application No. PCT/US2017/050137, dated Nov. 27, 2017.
International Search Report and Written Opinion for Application No. PCT/US2017/050355 dated Jan. 30, 2018.
Jaime et al., "Paclitaxel antibody conjugates and trehalose for preserving the immunological activity after freeze-drying," Curr Med Chem, 2004, 11(4):439-46 Abstract Only.
Jain et al., "Normalizing tremor vasculature with anti-angiogenic therapy, a new paradigm for combination therapy," Nat. Med. 7(9):987-989 (2001).
Jain, "Normalization of tumor vasculature: an emerging concept in antiangiogenic therapy," Science 317(5706):58-62 (2005).
Jin et al., "Paclitaxel-loaded nonparticles decorated with anti-CD133 antbibody: a targeted therapy for liver cancer stem cells," J. Nanopart. Res. 2014, 16:2157 (2014).
Jin et al: "Docetaxel-loaded PEG-albumin nanoparticles with improved antitumor efficiency against non-small cell lung cancer", Oncology Reports vol. 36, No. 2, Aug. 8, 2016 (Aug. 8, 2016), pp. 871-876, XP055425487, ISSN: 1021-335X, DOI: 10.3892/or.2016.4863.
Kelly et al. "Shape-Specific, Monodisperse Nano-Molding of Protein particles," J. Am. Chem. Soc. 130:5438-5439 (2008).
Lee et al., "The co-delivery of paclitaxel and Herceptin using cationic micellar nanoparticies", Biomaterials vol. 30, No. 5, Feb. 1, 2009, pp. 919-927.
Liang et al., "IFN-alpha regulates NK cell cytotoxicity through STAT1 pathway," Cytokine, Aug. 13, 2003 (Aug. 13, 2013), vol. 23, pp. 190-199.
Makridis, et al., "MHC class I and II antigen expression and interferon ? treatment of human midgut carcinoid tumors," World Journal of Surgery, Aug. 1, 1993 (Aug. 1, 1993), vol. 16, Iss. 4, pp. 481-486.
Meadows et al. "Anti-VEGF Therapies in the Clinic," Cold Spring Harbor Perspectives in Medicine, Oct. 1, 2012 (Oct. 1, 2012), vol. 2, pp. 1-27.
Mustacchi et al, "The role of taxanes in triple-negative breast cancer: literature review", Drug Design, Development and Therapy, vol. 9, Aug. 5, 2015, 16 pages.
Nahleh et al, "Swog S0800 (NCI CDR0000636131): addition of bevacizumab to neoadjuvant nab-paclitaxel with dose-dense doxorubicin and cyclophosphamide improves pathologic complete response (pCR) rates in inflammatory or locally advanced breast cancer", Breast Cancer Research and Treatment, vol. 158, No. 3 Jul. 8, 2016, 12 pages.
Nevala et at "Abstract B77: Targeted nano-immune conjugates to melanoma: Preclinical testing of bevacizumab targeted nab-paclitaxel", Cancer Immunology Research, vol. 3, Oct. 1, 2015, 3 pages.
Nevala et al, "Antibody-targeted paclitaxel loaded nanoparticles for the treatment of CD20 B-cell lymphoma", Scientific Reports, vol. 7, Apr. 5, 2017, 9 pages.
Nevala et al, "Antibody-Targeted Chemotherapy for the Treatment of Melanoma", Cancer Research, vol. 76, No. 13, Jul. 1, 2016, pp. 3954-3964.
Nevala et al, "Targeted nano-immune conjugates to melanoma: Preclinical testing of bevacizumab targeted nab-paclitaxel Proceedings of the AACR Special Conference: Tumor Immunology and Immunotherapy: A New Chapter", Dec. 1, 2014, 2 pages.
Nishida et al, English Translation of "Clinical Trials of New Drugs Cytotoxic Effect against Multiple Myeloma with High Expression of a CD38 Antigen and a Human CD38 Monoclonal Antibody Daratumumab CD38 Antigen", history of Medicine, Sep. 29, 2012, vol. 242, No. 13, 1176-1181.
Ortaldo et al., "Effects of several species of human leukocyte interferon on cytotoxic activity o fNK cells and monocytes," International Journal of Cancer, Mar. 15, 1983 (Mar. 15, 1983) vol. 31, No. 3, pp. 285-289.
Ouichi, "Antibody delivery—from basics to clinical test—Clinical development of antibody-drug conjugate," Drug Deliv. Sys. 28(5):424-429 (2013).
Parker et al., "Targeting CLL Cells Using Rituximab-Conjugated Surface Enhanced Raman Scattering (SERS) Gold Nanoparticles," Blood vol. 116, No. 21, Nov. 1, 2010, pp. 1109.
Petrelli et al., "Targeted Delivery for Breast Cancer Therapy: the History of Nanoparticle-Albumin-Bound Paclitaxel," Expert Opinion on Pharmacotherapy, Jun. 1, 2010 (Jun. 1, 2010), vol. 11, pp. 1413-1432.
Qu Na et al: "Cabazitaxel-loaded human serum albumin nanoparticles as a therapeutic agent against prostate cancer", International Journal of Nanomedicine, vol. 11, Jul. 26, 2016 (Jul. 26, 2016), pp. 3451-3459.
Rudikoff et al.; "Single amino acid substitution altering antigen-binding specificity," Proc Natl Acad Sci USA 1982 vol. 79 pp. 1979-1983.
Samaranayake et al., "Modified taxols. 5.1 Reaction of taxol with electrophilc reagents and preparation of a rearranged taxol derivative with tubtulin assembly activity", J. Org. Chem., vol. 56, 1991, pp. 5114-5119.
Soda et al., "Latest topics of new Medicine *Albumin-bound paclitaxel," Mol. Respiratory Dis. 17(1):100-103 (Mar. 1, 2013).
Stancovski et al., "Mechanistic aspects of the opposing effects of monoclonal antivodies to the ERBB2 receptor on tumor growth," Proc Natl Acad Sci USA, 88: 8691-8695, (1991).
Terui, English Translation of Molecular-Targeted Therapy for Cancer: Progresses and Challenges, "Daratumumab, Antibody Drug against Myeloma", Pharma Med., Nov. 10, 2013, vol. 31, No. 11, p. 27-30.
Volk et al., "Nab-paclitaxel efficacy in the orthotopic model of human breast cancer is significantly enhanced by concurrent anti-vascular endothelial growth factor A therapy," Neoplasia 10(6):613-623 (2008).
Volk-Draper et al, "Novel Model for Basaloid Triple-negative Breast Cancer: Behavior In Vivo and Response to Therapy", vol. 14, No. 10, Oct. 1, 2012, 18 pages.
Washington University School of Medicine "Phase I/II Study of Abraxane Recurrent and Refractory Lymphoma", ClinicalTrials.gov, Dec. 6, 2016, 7 pages.
Yu et al., "Interaction between bevacizumab and murine VEGF-A: a reassessment," Invest. Ophthalmol. Visual Sci. 49 (2): 522-527, Feb. 2008.
Yuan et al., "Time-dependent vascular regression and permeability changes in established human tumor xenografts induced by an anti-vascular endothelial growth factor/vascular permeability factor antibody," Proc. Natl. Acad. Sci. USA 93(25):14765-14770 (1996).
U.S. Appl. No. 15/052,623, office action dated Jan. 7, 2019.
U.S. Appl. No. 14/432,979, office action dated Jan. 7, 2019.
U.S. Appl. No. 15/092,433; office action dated Dec. 12, 2018.
U.S. Appl. No. 15/187,672, office action dated Nov. 28, 2018.
U.S. Appl. No. 15/412,536, office action dated Oct. 1, 2018.
U.S. Appl. No. 15/412,581; office action dated Nov. 13, 2018.
U.S. Appl. No. 15/413,257; office action dated Sep. 25, 2018.

(56) References Cited

OTHER PUBLICATIONS

U.S. Appl. No. 15/414,526; office action dated Nov. 16, 2018.
U.S. Appl. No. 15/414,533; office action dated Nov. 19, 2018.
U.S. Appl. No. 15/414,536; office action dated Oct. 11, 2018.
Elst et al. "Epidermal Growth Factor Receptor Expression and Activity In Acute Myeloid Leukemia", Blood 116:3144 (2010), abstract.
International Preliminary Report on Patentability for Application No. PCT/US2016/026270, dated Oct. 18, 2018.
International Preliminary Report on Patentability for Application No. PCT/US2017/012580; dated Jul. 19, 2018.
International Preliminary Report an Patentability for Application No. PCT/US2017/023442, dated Oct. 4, 2018.
International Preliminary Report on Patentability for Application No. PCT/US2017/023443, dated Oct. 4, 2018.
Lloyd et al. "Modelling the human immune response: performance of a 1011 human antibody repertoire against a broad panel of therapeutically relevant antigens", Protein Eng. , Design & Selection 22(3):159-168 (2009).
U.S. Appl. No. 15/452,669, office action dated Nov. 26, 2018
U.S. Appl. No. 15/412,596, office action dated Dec. 27, 2018.
Edwards et al. The Remarkable Flexibility of the Human Antibody Repertoire: Isolation of Over One Thousand Different Antbodies to a Single Protein, BLyS, J. Mol. Biol 334:103-118.
Package Insert, Campath® (ALEMTUZUMAB), Millennium and ILEX Partners, LP, 13 pages, available May 2001.
U.S. Appl. No. 15/092,433, office action dated May 30, 2019.
U.S. Appl. No. 15/092,403, office action dated May 23, 2019.
U.S. Appl. No. 15/430,411, office action dated May 1, 2019.
Anonymous, "Phase I/II Study of Abraxane in Recurrent and Refractory Lymphoma", NCT01555853, ClinicalTrials.gov, Jun. 6, 2014 (8 pages).
U.S. Appl. No. 15/052,336, office action dated Jan. 22, 2019.
U.S. Appl. No. 15/412,581, office action dated Mar. 8, 2019.
U.S. Appl. No. 15/412,610, office action dated Mar. 14, 2019.
U.S. Appl. No. 15/414,526; office action dated Mar. 12, 2019.
U.S. Appl. No. 15/414,533; office action dated Mar. 8, 2019.
U.S. Appl. No. 15/456,377; office action dated Mar. 19, 2019.
U.S. Appl. No. 15/456,382; office action dated Mar. 18, 2019.
U.S. Appl. No. 15/456,391; office action dated Mar. 15, 2019.
U.S. Appl. No. 15/456,395; office action dated Mar. 28, 2019.
U.S. Appl. No. 15/456,399; office action dated Mar. 28, 2019.
U.S. Appl. No. 15/460,552; office action dated Apr. 1, 2019.
U.S. Appl. No. 15/460,699; office action dated Mar. 28, 2019.
U.S. Appl. No. 15/461,288; office action dated Apr. 1, 2019.
Bedu-Addo "Understanding Lyophilization Formulation Development", Pharmaceutical Technology Lyophilization, pp. 10-18 (2004).
Cheng et el. Molecularly targeted drugs for metastatic colorectal cancer. Drug Des Devel Ther. Nov. 1, 2013 ;7: 1315-22 (Year: 2013).
Coiffier "The Role of Rituximab in Lymphomas", Rev. Bras. Hematol. Hemoter., 2002, vol. 24, No. 3, ISSN: 1516-8484 (6 pages).
International Preliminary Report on Patentability for Application No. PCT/US2017/045643, dated Feb. 14, 2019.
International Preliminary Report on Patentability for Application No. PCT/US2017/049745, dated Mar. 14, 2019.
International Preliminary Report on Patentability for Application No. PCT/US2017/049746, dated Mar. 14, 2019.
International Preliminary Report on Patentability for Application No. PCT/US2017/050137 dated Mar. 21, 2019.
Iqbal et al. Anti-Cancer Actions of Denosumab, Curr Osteoporos Rep. Dec. 2011;9(4): 173-6. (Year: 2011).
Matthay et al. Promising therapeutic targets in neuroblastoma. Clin Cancer Res. May 15, 2012;18(10):2740-53. (Year: 2012).
Reck et al. "Ipilimumab in combination with paclitaxel and carboplatin as first line therapy in extensive-disease-small-cell lung cancer results from a randomized, double-blind, multicenter phase 2 trial", Ann Oncol. 24(1):75-83 (2013).
Robak, T. Emerging monoclonal antibodies and related agents for the treatment of chronic lymphocytic leukemia. Future Oneal, Jan. 2013;9(1):69-91. Abstract Only, (Year: 2013).
Verma et al. "Effect of surface properties on nanoparticle-cell interactions", Small, 6(1 ): 12-21, (2010).
European Application No. 16837869.3, Extended European Search Report dated Apr. 4, 2019.
U.S. Appl. No. 15/452,669; office action dated Jun. 24, 2019.
Beers et al. "CD20 as a Target for Therapeutic Type I and II Monoclonal Antibodies", Seminars in Hematology 47(2):107-114 (2010).
U.S. Appl. No. 15/456,377; office action dated Jul. 5, 2019.
U.S. Appl. No. 15/456,382; office action dated Jul. 8, 2019.

\* cited by examiner

| AB160Kd | | Temperature | | |
|---|---|---|---|---|
| | | RT | 37C | 58C |
| pH | 3 | 8.2 x 10(-10) | 1.51 x 10(-11) | No Binding |
| | 5 | 1.45 x 10(-10) | 6.17 x 10(-9) | 1.75 x 10(-11) |
| | 7 | 2.2 x 10(-8) | 1.51 x 10(-8) | 8.21 x 10(-10) |
| | 9 | 1.3 x 10(-9) | 1.39 x 10(-5) | 2.0 x 10(-9) |

FIG. 2B

|  | NoTumor | | Tumor | |
|---|---|---|---|---|
|  | AB160 ± SD | ABX ± SD | AB160 ± SD | ABX ± SD |
| $C_{max}$ (µg/mL) | 63.3 ± 39.4 | 65.5 ± 14.4 | 55.7 ± 21.2 | 63.3 ± 17.3 |
| Half-life (hrs) | 4.7 | 3.8 | 8.0 | 4.5 |
| $AUC_{0-24h}$ (µg/ml x h) | 129 | 133 | 112 | 128 |
| $AUC_{0-\infty}$ (µg/ml x h) | 129 | 133 | 112 | 128 |

FIG. 4C

|  | $C_{max}$ µg/mL ± SD | $AUC_{0-8h}$ µg/mL x h |
|---|---|---|
| AB160, No Tumor | 66.1 ± 19.8 (30%) | 40.1 |
| ABX, No Tumor | 80.4 ± 2.7 (3%) | 47.2 |
| AB160, Small Tumor | 44.4 ± 12.1 (27%) | 26.9 |
| ABX, Small Tumor | 48.4 ± 12.3 (25%) | 28.9 |
| AB160, Large Tumor | 22.8 ± 6.9 (30%) | 15.3 |
| ABX, Large Tumor | 30.7 ± 5.2 (17%) | 19.7 |

FIG. 4G

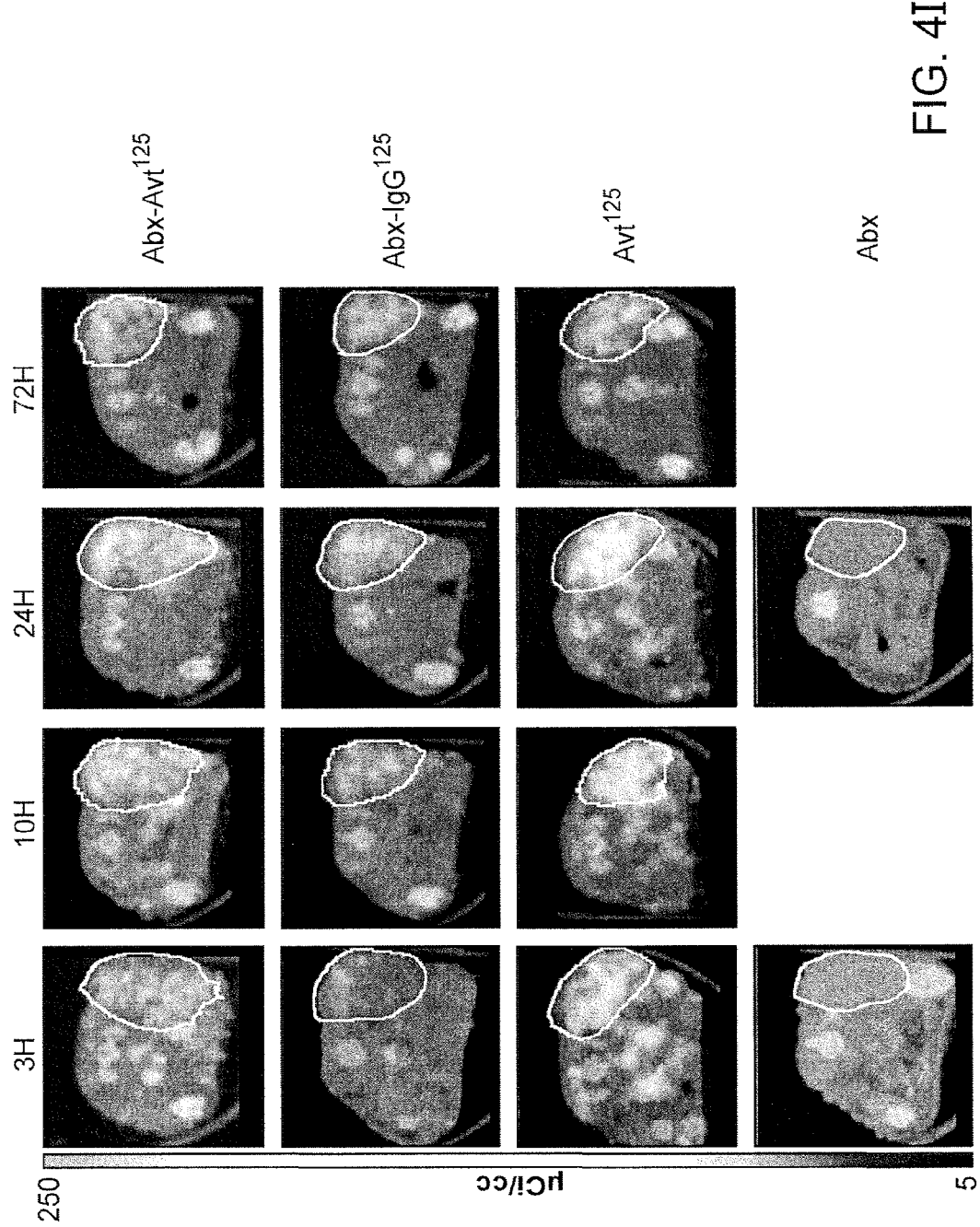

| Rituximab | pH3 | pH5 | pH7 | pH9 |
|---|---|---|---|---|
| Kd | $4.49 \times 10^{-10}$ | $2.93 \times 10^{-9}$ | $3.78 \times 10^{-9}$ | $2.50 \times 10^{-8}$ |

| Trastuzumab | pH3 | pH5 | pH7 | pH9 |
|---|---|---|---|---|
| Kd | $2.61 \times 10^{-9}$ | $1.23 \times 10^{-9}$ | $2.59 \times 10^{-9}$ | $1.91 \times 10^{-9}$ |

FIG. 5C

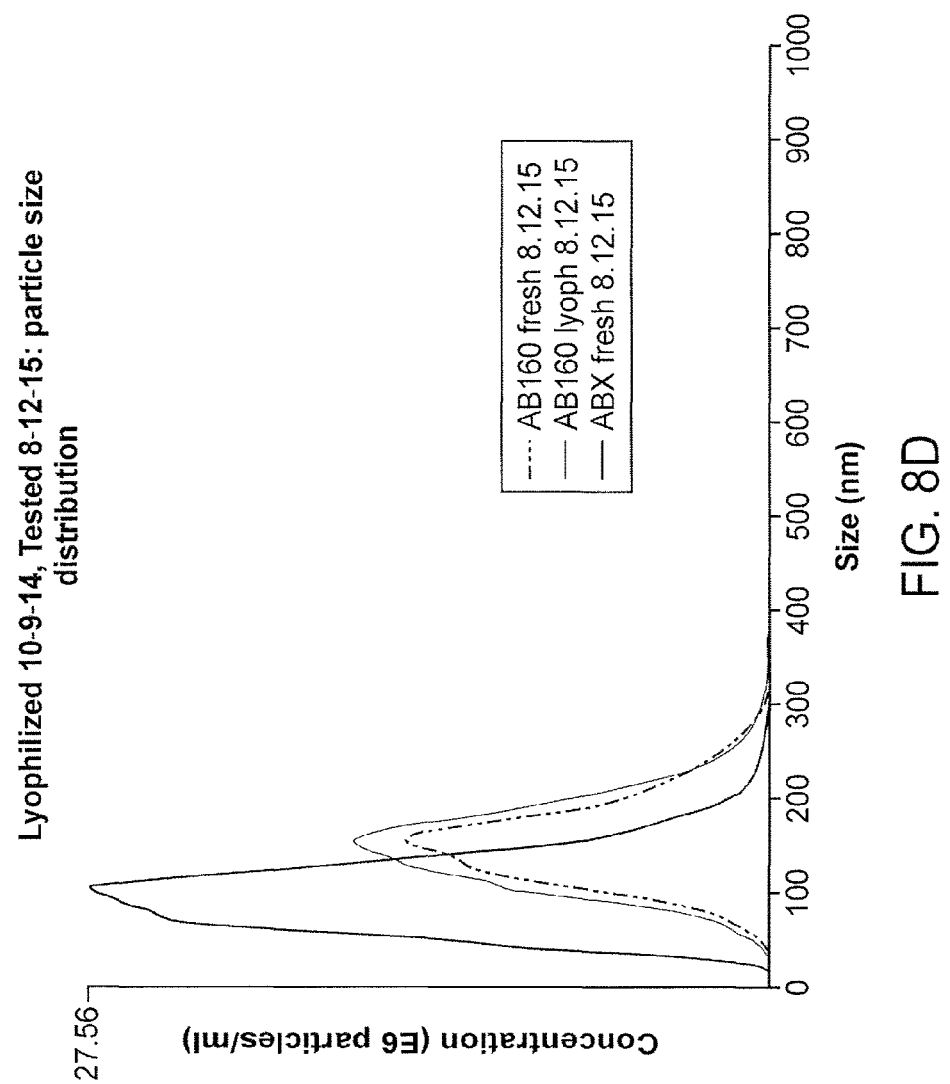

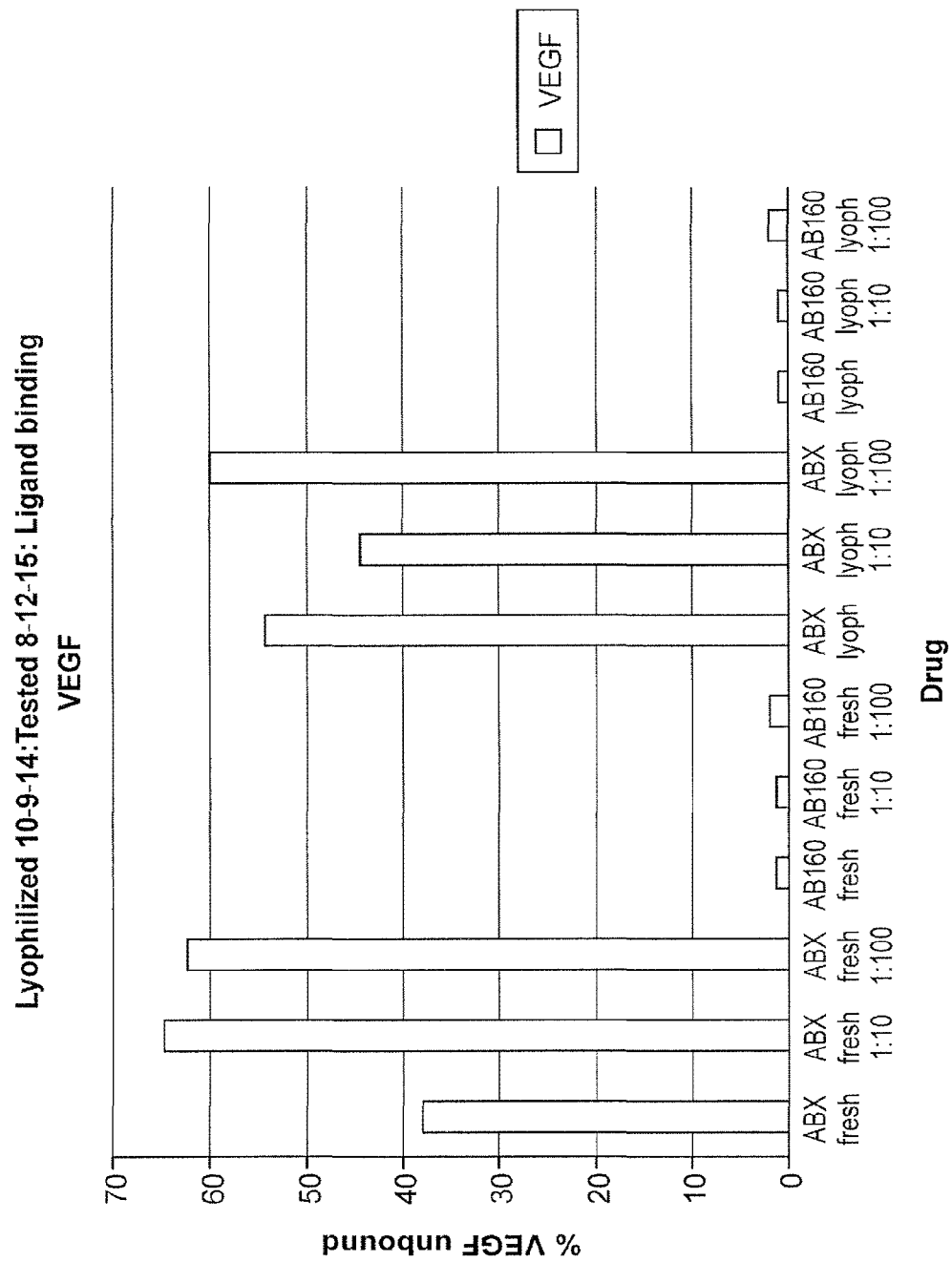

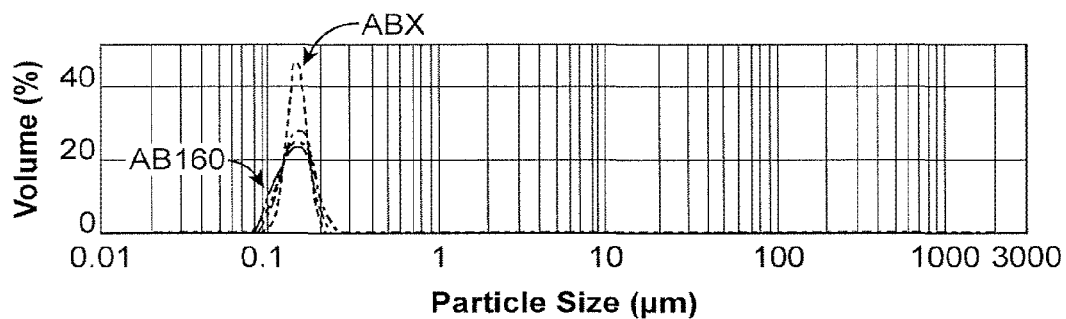
FIG. 9A
| | d (0.1) | d (0.5) | d (0.9) |
|---|---|---|---|
| ABX | 0.125 | 0.146 | 0.174 |
| 1 hour | 0.108 | 0.144 | 0.193 |
| 2 hours | 0.107 | 0.145 | 0.195 |
| 4 hours | 0.113 | 0.146 | 0.187 |
| 6 hours | 0.108 | 0.147 | 0.199 |
| 8 hours | 0.114 | 0.147 | 0.189 |
| 24 hours | 0.111 | 0.148 | 0.197 |
FIG. 9B
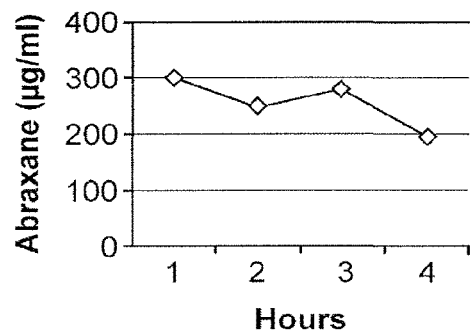
FIG. 9C

CARRIER-ANTIBODY COMPOSITIONS AND METHODS OF MAKING AND USING THE SAME

CROSS REFERENCE TO RELATED APPLICATIONS

This application is a continuation of U.S. application Ser. No. 15/060,912, filed Mar. 4, 2016; which is a divisional of U.S. application Ser. No. 14/882,327, filed Oct. 13, 2015, now U.S. Pat. No. 9,446,148; which is a continuation of PCT Application No. PCT/US 15/54295, filed Oct. 6, 2015, which claims the benefit of the filing date of U.S. Provisional Patent Application No. 62/060,484, filed Oct. 6, 2014; and U.S. Provisional Patent Application Nos. 62/206,770; 62/206,771; and 62/206,772, filed Aug. 18, 2015. The foregoing are incorporated by reference in their entireties.

FIELD OF THE INVENTION

This disclosure relates to novel compositions of antibodies and carrier proteins and methods of making and using the same, in particular, as a cancer therapeutic.

STATE OF THE ART

Chemotherapy remains a mainstay for systemic therapy for many types of cancer, including melanoma. Most chemotherapeutics are only slightly selective to tumor cells, and toxicity to healthy proliferating cells can be high (Allen T M. (2002) *Cancer* 2:750-763), often requiring dose reduction and even discontinuation of treatment. In theory, one way to overcome chemotherapy toxicity issues as well as improve drug efficacy is to target the chemotherapy drug to the tumor using antibodies that are specific for proteins selectively expressed (or overexpressed) by tumors cells to attract targeted drugs to the tumor, thereby altering the biodistribution of the chemotherapy and resulting in more drug going to the tumor and less affecting healthy tissue. Despite 30 years of research, however, specific targeting rarely succeeds in the therapeutic context.

Conventional antibody dependent chemotherapy (ADC) is designed with a toxic agent linked to a targeting antibody via a synthetic protease-cleavable linker. The efficacy of such ADC therapy is dependent on the ability of the target cell to bind to the antibody, the linker to be cleaved, and the uptake of the toxic agent into the target cell. Schrama, D. et al. (2006) *Nature reviews. Drug discovery* 5:147-159.

Antibody-targeted chemotherapy promised advantages over conventional therapy because it provides combinations of targeting ability, multiple cytotoxic agents, and improved therapeutic capacity with potentially less toxicity. Despite extensive research, clinically effective antibody-targeted chemotherapy remains elusive: major hurdles include the instability of the linkers between the antibody and chemotherapy drug, reduced tumor toxicity of the chemotherapeutic agent when bound to the antibody, and the inability of the conjugate to bind and enter tumor cells. In addition, these therapies did not allow for control over the size of the antibody-drug conjugates.

There remains a need in the art for antibody-based cancer therapeutics that retain cytoxic effect for targeted drug delivery to provide reliable and improved anti-tumor efficacy over prior therapeutics.

In addition, as to any therapeutic application, there also remains a need for the composition to be stable in its physical, chemical and biological properties.

Lyophilization, or freeze drying, removes water from a composition. In the process, the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. Biopharm. 3(9)26-30 (1990) and Arakawa et al., Pharm. Res. 8(3):285-291 (1991).

While proteins may be lyophilized, the process of lyophilization and reconstitution may affect the properties of the protein. Because proteins are larger and more complex than traditional organic and inorganic drugs (i.e. possessing multiple functional groups in addition to complex three-dimensional structures), the formulation of such proteins poses special problems. For a protein to remain biologically active, a formulation must preserve intact the conformational integrity of at least a core sequence of the protein's amino acids while at the same time protecting the protein's multiple functional groups from degradation. Degradation pathways for proteins can involve chemical instability (i.e. any process which involves modification of the protein by bond formation or cleavage resulting in a new chemical entity) or physical instability (i.e. changes in the higher order structure of the protein). Chemical instability can result from deamidation, racemization, hydrolysis, oxidation, beta elimination or disulfide exchange. Physical instability can result from denaturation. aggregation, precipitation or adsorption, for example. The three most common protein degradation pathways are protein aggregation, deamidation and oxidation. Cleland, et al., Critical Reviews in Therapeutic Drug Carrier Systems 10(4): 307-377 (1993).

In the present invention, the composition comprises nanoparticles which contain (a) carrier protein (b) antibody and (c) optionally a therapeutic agent. The antibody is believed to be bound to the carrier protein through hydrophobic interactions which, by their nature, are weak. The lyophilization and reconstitution of such a composition must, therefore, not only preserve the activity of the individual components, but also their relative relationship in nanoparticle.

Further challenges are imposed because the nanoparticles are used in therapy.

For example, rearrangement of the hydrophobic components in the nanoparticle may be mitigated through covalent bonds between the components. However, such covalent bonds pose challenges for the therapeutic use of nanoparticles in cancer treatment. The antibody, carrier protein, and additional therapeutic agent typically act at different locations in a tumor and through different mechanisms. Non-covalent bonds permit the components of the nanoparticle to dissociate at the tumor. Thus, while a covalent bond may be advantageous for lyophilization, it may be disadvantageous for therapeutic use.

The size of the nanoparticles, and the distribution of the size, is also important. The nanoparticles of the invention may behave differently according to their size. At large sizes, the nanoparticles or the agglomeration of these particles may block blood vessels either of which can affect the performance and safety of the composition.

Finally, cryoprotectants and agents that assist in the lyophilization process must be safe and tolerated for therapeutic use.

SUMMARY

In one aspect, provided herein are nanoparticle compositions comprising nanoparticles wherein each of the nanoparticles comprises a carrier protein, between about 100 to about 1000 antibodies, and optionally at least one therapeutic agent, wherein the antibodies are arranged outward from the surface of the nanoparticles and wherein the nanoparticles are capable of binding to a predetermined epitope in vivo.

When administered intravenously, large particles (e.g. greater than 1 μm) are typically disfavored because they can become lodged in the microvasculature of the lungs. At the same time, larger particles can accumulate in the tumor or specific organs. See e.g. 20-60 micron glass particle that is used to inject into the hepatic artery feeding a tumor of the liver, called "therasphere" (in clinical use for liver cancer).

Therefore, for intravenous administration, particles under 1 μm are used. Particles over 1 μm are, more typically, administered directly into a tumor ("direct injection") or into an artery feeding into the site of the tumor.

In another aspect, provided herein are nanoparticle compositions comprising nanoparticles wherein each of the nanoparticles comprises a carrier protein that is not albumin, between about 100 to about 100 antibodies, preferably about 400 to about 800 antibodies, and optionally at least one therapeutic agent, wherein the antibodies are arranged on an outside surface of the nanoparticles and wherein the nanoparticles are capable of binding to a predetermined epitope in vivo. When nanoparticles multimerize, the number of antibodies is increased proportionally. For example, if a 160 nm nanoparticle contains 400 antibodies, a 320 nm dimer contains about 800 antibodies.

In another aspect, provided herein are nanoparticle compositions comprising nanoparticles, wherein each of the nanoparticles comprises carrier protein, between about 400 to about 800 antibodies, and optionally at least one therapeutic agent that is not paclitaxel, wherein the antibodies are arranged on a surface of the nanoparticles such that the binding portion of the antibody is directed outward from that surface and wherein the nanoparticles are capable of binding to a predetermined epitope in vivo.

In other embodiments, the nanoparticles multimerize, e.g. dimerize. Multimerization may be observed as multiples of the weight or size of the unit molecule, e.g. 160 nm particles multimerize to about 320 nm, 480 nm, 640 nm, etc. In some embodiments, less than 20% of the population are multimers. In some embodiments, more than 80% of the population are multimers.

In one embodiment, the weight ratio of carrier-bound drug to antibody (e.g. albumin-bound paclitaxel to bevacizumab) is between about 5:1 to about 1:1. In one embodiment, the weight ratio of carrier-bound drug to antibody is about 10:4. In one embodiment, the antibody is a substantially single layer of antibodies on all or part of the surface of the nanoparticle. In one embodiment, less than 0.01% of nanoparticles in the composition have a size selected from the group consisting of greater than 200 nm, greater than 300 nm, greater than 400 nm, greater than 500 nm, greater than 600 nm, greater than 700 nm and greater than 800 nm. Larger sizes are believed to be the result of multimerization of several nanoparticles, each comprising a core and antibody coating on all or part of the surface of each nanoparticle.

The invention further includes lyophilized compositions, and lyophilized compositions that do not materially differ from, or are the same as, the properties of freshly-prepared nanoparticles. In particular, the lypholized composition, upon resuspending in aqueous solution, is similar or identical to the fresh composition in terms of particle size, particle size distribution, toxicity for cancer cells, antibody affinity, and antibody specificity. The invention is directed to the surprising finding that lyophilized nanoparticles retain the properties of freshly-made nanoparticles notwithstanding the presence of two different protein components in these particles.

In one aspect, this invention relates to a lyophilized nanoparticle composition comprising nanoparticles, wherein each of the nanoparticles comprises a carrier-bound drug core and an amount of antibody arranged on a surface of the core such that the binding portion of the antibody is directed outward from that surface, wherein the antibodies retain their association with the outside surface of the nanoparticle upon reconstitution with an aqueous solution. In one embodiment, the lyophilized composition is stable at room temperature for at least 3 months. In one embodiment, the reconstituted nanoparticles retain the activity of the therapeutic agent and are capable of binding to the target in vivo.

In one embodiment, the average reconstituted nanoparticle size is from about 130 nm to about 1 μm. In a preferred embodiment, the average reconstituted nanoparticle size is from about 130 nm to about 200 nm, and more preferably about 160 nm. In one embodiment, in the average reconstituted nanoparticle size is from greater than 800 nm to about 3.5 μm, comprising multimers of smaller nanoparticles, e.g. multimers of 100-200 nm nanoparticles. In one embodiment, the weight ratio of core to antibody is from greater than 1:1 to about 1:3.

In one aspect, this disclosure relates to a lyophilized nanoparticle composition comprising nanoparticles, wherein each of the nanoparticles comprises: (a) an albumin-bound paclitaxel core and (b) between about 400 to about 800 molecules of bevacizumab arranged on a surface of the albumin-bound paclitaxel core such that the binding portion of the antibody is directed outward from that surface, wherein the antibodies retain their association with the surface of the nanoparticle upon reconstitution with an aqueous solution, provided that said lyophilized composition is stable at about 20° C. to about 25° C. for at least 3 months and the reconstituted nanoparticles are capable of binding to VEGF in vivo.

In other aspects, this disclosure relates to a lyophilized nanoparticle composition comprising nanoparticles, wherein each of the nanoparticles comprises: (a) an albumin-bound paclitaxel core and (b) an amount of bevacizumab arranged on a surface of the albumin-bound paclitaxel core such that the binding portion of the antibody is directed outward from that surface, wherein the antibodies retain their association with the surface of the nanoparticle upon reconstitution with an aqueous solution, provided that said lyophilized composition is stable at about 20° C. to about 25° C. for at least 3 months and the reconstituted nanoparticles are capable of binding to VEGF in vivo, and further wherein the average reconstituted nanoparticle size is not substantially different from the particle size of the freshly prepared nanoparticles. In some embodiments, the particle sizes are between 200 and 800 nm, including 200, 300, 400, 500, 600, 700 or 800 nm. In other embodiments, the particles are larger, e.g. from greater than 800 nm to about 3.5 μm. In some embodiments, the particles are multimers of nanoparticles.

In some embodiments, the weight ratio of albumin-bound paclitaxel to bevacizumab is between about 5:1 to about 1:1. In other embodiments, the weight ratio of albumin-bound paclitaxel to bevacizumab is about 10:4. In further embodiments, the weight ratio of albumin-bound paclitaxel to bevacizumab is from greater than 1:1 to about 1:3.

In some embodiments, the core is albumin-bound paclitaxel, and the antibodies are selected from antibodies that selectively recognize VEGF (e.g. bevacizumab/Avastin), antibodies that selectively recognize CD20 (e.g. rituximab/Rituxin) and antibodies that selectively recognize Her2 (Trastuzumab/Herceptin).

In some embodiments, the at least one therapeutic agent is located inside the nanoparticle. In other embodiments, the at least one therapeutic agent is located on the outside surface of the nanoparticle. In yet other embodiments, the at least one therapeutic agent is located inside the nanoparticle and on the outside surface of the nanoparticle.

In some embodiments, the nanoparticle contains more than one type of therapeutic agent. For example, a taxane and a platinum drug, e.g. paclitaxel and cisplatin.

In some embodiments, the antibodies are selected from the group consisting of ado-trastuzumab emtansine, alemtuzumab, bevacizumab, cctuximab, denosumab, dinutuximab, ipilimumab, nivolumab, obinutuzumab, ofatumumab, panitumumab, pembrolizumab, pertuzumab, rituximab, and trastuzumab. In some embodiments, the antibodies are a substantially single layer of antibodies on all or part of the surface of the nanoparticle.

In further embodiments, the antibodies are less glycosylated than normally found in natural human antibodies. Such glycosylation can be influenced by e.g. the expression system, or the presence of glycosylation inhibitors during expression. In some embodiments, the glycosylation status of an antibody is altered through enzymatic or chemical action.

In some embodiments, the at least one therapeutic agent is selected from the group consisting of abiraterone, bendamustine, bortezomib, carboplatin, cabazitaxel, cisplatin, chlorambucil, dasatinib, docetaxel, doxonibicin, epirubicin, erlotinib, etoposide, everolimus, gefitinib, idarubicin, imatinib, hydroxyurea, imatinib, lapatinib, leuprorelin, melphalan, methotrexate, mitoxantrone, ncdaplatin, nilotinib, oxaliplatin, paclitaxel, pazopanib, pemetrexed, picoplatin, romidepsin, satraplatin, sorafenib, vemurafenib, sunitinib, teniposide, triplatin, vinblastine, vinorelbine, vincristine, and cyclophosphamide.

In some embodiments, the nanoparticle further comprises at least one additional therapeutic agent that is not paclitaxel or bevacizumab.

In some embodiments, the antibodies, carrier protein and, when present, therapeutic agent, are bound through non-covalent bonds.

In some embodiments, the carrier protein is selected from the group consisting of gelatin, elastin, gliadin, legumin, zein, a soy protein, a milk protein, and a whey protein. In other embodiments, the carrier protein is albumin, for example, human serum albumin.

In some embodiments, the composition is formulated for intravenous delivery. In other embodiments, the composition is formulated for direct injection or perfusion into a tumor.

In some embodiments, the average nanoparticle size in the composition is from greater than 800 nm to about 3.5 µm.

In some embodiments, the nanoparticles have a dissociation constant between about $1\times10^{-11}$ M and about $1\times10^{-9}$ M.

In another aspect, provided herein are methods of making nanoparticle compositions, wherein said methods comprise contacting the carrier protein and the optionally at least one therapeutic agent with the antibodies in a solution having a pH of between 5.0 and 7.5 and a temperature between about 5° C. and about 60° C., between about 23° C. and about 60° C., or between about 55° C. and about 60° C. under conditions and ratios of components that will allow for formation of the desired nanoparticles. In one embodiment, the nanoparticle is made at 55-60° C. and pH 7.0. In another aspect, provided herein are methods of making the nanoparticle compositions, wherein said method comprises (a) contacting the carrier protein and optionally the at least one therapeutic agent to form a core and (b) contacting the core with the antibodies in a solution having a pH of about 5.0 to about 7.5 at a temperature between about 5° C. and about 60° C., between about 23° C. and about 60° C., or between about 55° C. and about 60° C. under conditions and ratios of components that will allow for formation of the desired nanoparticles.

The amount of components (e.g., carrier protein, antibodies, therapeutic agents, combinations thereof) is controlled in order to provide for formation of the desired nanoparticles. A composition wherein the amount of components is too dilute will not form the nanoparticles as described herein. In a preferred embodiment, weight ratio of carrier protein to antibody is 10:4. In some embodiments, the amount of carrier protein is between about 1 mg/mL and about 100 mg/mL. In some embodiments, the amount of antibody is between about 1 mg/mL and about 30 mg/mL. For example, in some embodiments, the ratio of carrier protein:antibody:solution is approximately 9 mg of carrier protein (e.g., albumin) to 4 mg of antibody (e.g., BEV) in 1 mL of solution (e.g., saline). An amount of therapeutic agent (e.g., taxol) can also be added to the carrier protein.

In further embodiments, the nanoparticles are made as above, and then lyophilized.

In another aspect, provided herein are methods for treating a cancer cell, the method comprising contacting the cell with an effective amount of a nanoparticle composition disclosed herein to treat the cancer cell.

In another aspect, provided herein are methods for treating a tumor in a patient in need thereof, the method comprising contacting the cell with an effective amount of a nanoparticle composition disclosed herein to treat the tumor. In some embodiments, the size of the tumor is reduced. In other embodiments, the nanoparticle composition is administered intravenously. In yet other embodiments, the nanoparticle composition is administered by direct injection or perfusion into the tumor.

In some embodiments, the methods provided herein include the steps of: a) administering the nanoparticle composition once a week for three weeks; b) ceasing administration of the nanoparticle composition for one week; and c) repeating steps a) and b) as necessary to treat the tumor.

In related embodiments, the treatment comprises administration of the targeting antibody prior to administration of the nanoparticles. In one embodiment, the targeting antibody is administered between about 6 and 48, or 12 and 48 hours prior to administration of the nanoparticles. In another embodiment, the targeting antibody is administered between 6 and 12 hours prior to administration of the nanoparticles. In yet another embodiment, the targeting antibody is administered between 2 and 8 hours prior to administration of the nanoparticles. In still other embodiments, the targeting antibody is administered a week prior to administration of the nanoparticles. For example, administration of a dose of BEV 24 hours prior to administration of AB160. In another example, prior administration of rituximab prior to administering AR nanoparticles. The antibody administered prior to the nanoparticle may be administered as a dose that is subtherapeutic, such as ½, $\frac{1}{10}^{th}$ or ½₀ the amount normally considered therapeutic. Thus, in man, pretreatment with BEV may comprise administration of 1 mg/kg BEV which is $\frac{1}{10}^{th}$ the usual dose, followed by administration of AB160.

In some embodiments, the therapeutically effective amount comprises about 75 mg/m² to about 175 mg/m² of the carrier protein (i.e., milligrams carrier protein per m² of the patient). In other embodiments, the therapeutically effective amount comprises about 75 mg/m² to about 175 mg/m² of therapeutic agent (e.g., paclitaxel). In other embodiments, the therapeutically effective amount comprises about 30 mg/m² to about 70 mg/m² of the antibody. In yet other embodiments, the therapeutically effective amount comprises about 30 µg/m² to about 70 mg/m² bevacizumab.

In one specific embodiment, the lypholized composition comprises from about 75 mg/m² to about 175 mg/m² of the carrier protein which is preferably albumin; from about 30 mg/m² to about 70 mg/m² of the antibody which is preferably bevacizumab; and from about about 75 mg/m² to about 175 mg/m² of paclitaxel.

BRIEF DESCRIPTION OF THE DRAWINGS

The following figures are representative only of the invention and are not intended as a limitation. For the sake of consistency, the nanoparticles of this invention using Abraxane® and bevacizumab employ the acronym "AB" and the number after AB such as AB160 is meant to confer the average particle size of these nanoparticles (in nanometers). Likewise, when the antibody is rituximab, the acronym is "AR" while the number thereafter remains the same.

FIG. 2B shows affinity of the binding of ABX and BEV (as determined by light absorption (Blitz) technology). The data is displayed as dissociation constant (Kd). The binding affinity of particles made at four pH levels (3, 5, 7, 9) and 3 temperatures (RT, 37° C. and 58° C.) was assessed, and the data are representative of 5 experiments.

FIG. 4C shows the half-life and AUC values calculated from the blood concentration data provide in FIGS. 4A and 4B.

FIG. 4G shows the and the AUC calculated from the data in FIG. 4F.

FIG. 4I shows I-125 radioactivity levels in mice treated with AB160 relative to ABX alone.

FIG. 5C shows the binding affinity of rituximab and trastuzumab as compared to ABX at pH 3, 5, 7 and 9, determined by biolayer interferometry (BLItz) technology. The dissociation constants are displayed for each interaction.

FIG. 8D shows the size distribution of AB160 nanoparticles that were lyophilized, stored at room temperature for ten months, and reconstituted, as compared to fresh AB160 or ABX alone.

FIG. 8E shows the ligand (VEGF) binding ability of AB160 nanoparticles that were lyophilized, stored at room temperature for ten months, and reconstituted, as compared to fresh AB160 or ABX alone.

FIGS. 9A-C show the size distributions of the ABX-BEV complexes at I.V. infusion conditions (ABX final concentration of 5 mg/mL) incubated in saline at room temperature for up to 24 hours (FIGS. A and B). By 4 hours at room temperature, there is some evidence of complex breakdown by ELISA (20%, FIG. C).

DETAILED DESCRIPTION

Figure 1A:
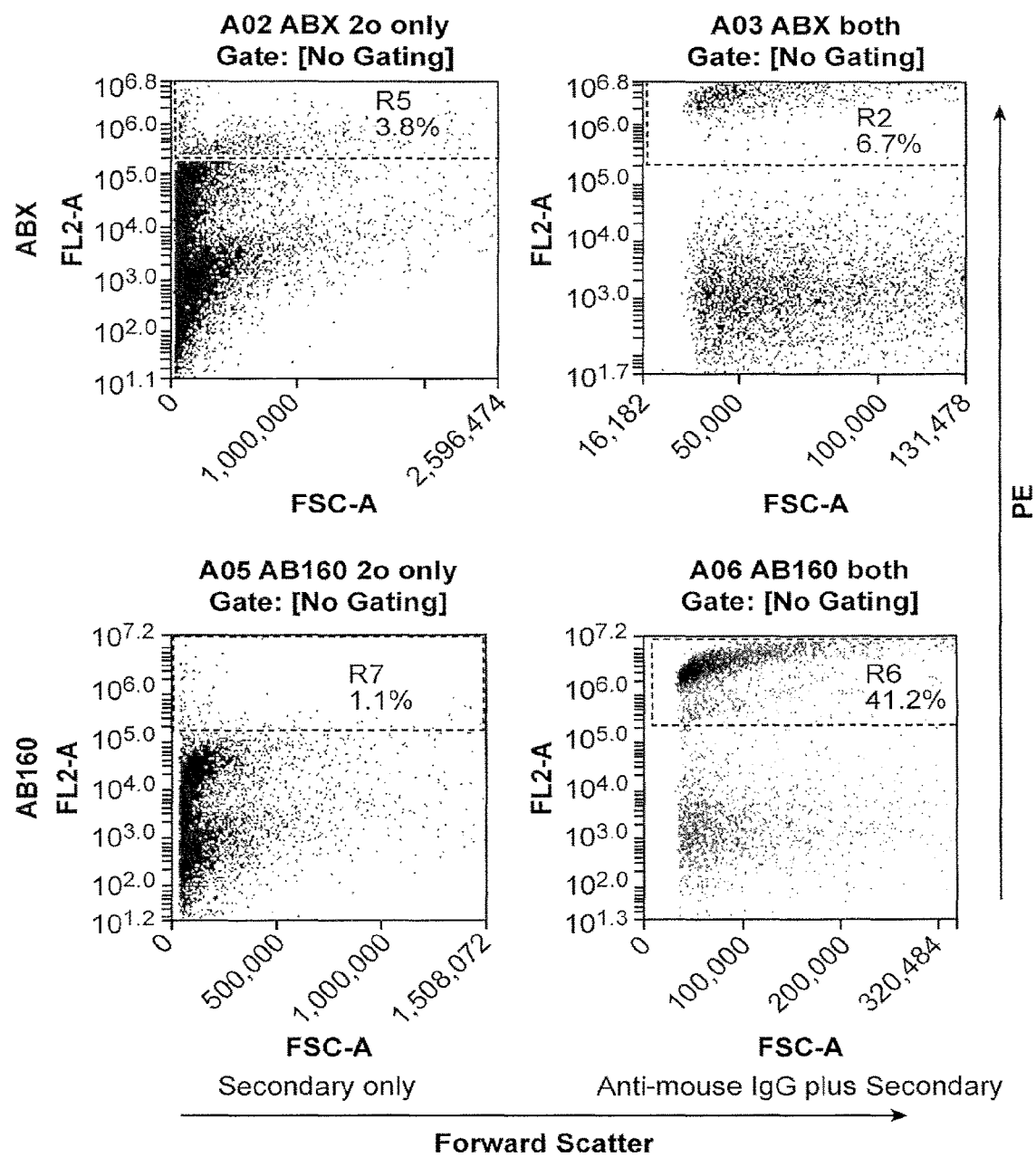
FIG. 1A shows flow cytometry scatterplots including: Abraxane® (ABX—commercially available from Celgene Corporation, Summit, N.J. 07901) stained with secondary antibody only (top left panel), ABX stained with goat anti-mouse IgG1 Fab plus secondary antibody (top right panel), AB160 (which is a nanoparticle of albumin-bound paclitaxel to bevacizumab in a ratio of about 10:4 and have an average particle size of 160 nm) stained with secondary antibody only (bottom left panel), or AB160 stained with goat anti-mouse IgG1 Fab plus secondary antibody (bottom right panel).

After reading this description it will become apparent to one skilled in the art how to implement the invention in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description of the invention is divided into various sections only for the reader's convenience and disclosure found in any section may be combined with that in another section. Titles or subtitles may be used in the specification for the convenience of a reader, which are not intended to influence the scope of the present invention.

Definitions

Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to a dose amount means that the dose may vary by +/−10%. For example, "about 400 to about 800 antibodies" indicates that an outside surface of a nanoparticles contain an amount of antibody between 360 and 880 particles.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

The term "nanoparticle" as used herein refers to particles having at least one dimension which is less than 5 microns. In preferred embodiments, such as for intravenous administration, the nanoparticle is less than 1 micron. For direct administration, the nanoparticle is larger. Even larger particles are expressly contemplated by the invention.

In a population of particles, the size of individual particles are distributed about a mean. Particle sizes for the population can therefore be represented by an average, and also by percentiles. D50 is the particle size below which 50% of the particles fall. 10% of particles are smaller than the D10 value and 90% of particles are smaller than D90. Where unclear, the "average" size is equivalent to D50. So, for example, AB160 refers to nanoparticles having an average size of 160 nanometers.

The term "nanoparticle" may also encompass discrete multimers of smaller unit nanoparticles. For example, a 320 nm particle comprises a dimer of a unit 160 nm nanoparticle. For 160 nm nanoparticles, multimers would therefore be approximately 320 nm, 480 nm, 640 nm, 800 nm, 960 nm, 1120 nm, and so on.

The term "carrier protein" as used herein refers to proteins that function to transport antibodies and/or therapeutic agents. The antibodies of the present disclosure can reversibly bind to the carrier proteins. Exemplary carrier proteins are discussed in more detail below.

The term "core" as used herein refers to central or inner portion of the nanoparticle which may be comprised of a carrier protein, a carrier protein and a therapeutic agent, or other agents or combination of agents. In some embodiments, a hydrophobic portion of the antibody may be incorporated into the core.

The term "therapeutic agent" as used herein means an agent which is therapeutically useful, e.g., an agent for the treatment, remission or attenuation of a disease state, physiological condition, symptoms, or etiological factors, or for the evaluation or diagnosis thereof. A therapeutic agent may be a chemotherapeutic agent, for example, mitotic inhibitors, topoisomerase inhibitors, steroids, anti-tumor antibiotics, antimetabolites, alkylating agents, enzymes, proteasome inhibitors, or any combination thereof.

The term "antibody" or "antibodies" as used herein refers to immunoglobulin molecules and immunologically active portions of immunoglobulin molecules (i.e., molecules that contain an antigen binding site that immuno-specifically bind an antigen). The term also refers to antibodies comprised of two immunoglobulin heavy chains and two immunoglobulin light chains as well as a variety of forms including full length antibodies and portions thereof; including, for example, an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody (dAb), a diabody, a multispecific antibody, a dual specific antibody, an anti-idiotypic antibody, a bispecific antibody, a functionally active epitope-binding fragment thereof, bifunctional hybrid antibodies (e.g., Lanzavecchia et al., Eur. J. Immunol. 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984); Harlow and Lane, Antibodies. A Laboratory Manual, Cold Spring Harbor Laboratory (1988); Hunkapiller and Hood, Nature, 323, 15-16 (1986), which are incorporated herein by reference). The antibody may be of any type (e.g., IgG, IgA, IgM, IgE or IgD). Preferably, the antibody is IgG. An antibody may be non-human (e.g., from mouse, goat, or any other animal), fully human, humanized, or chimeric.

The term "dissociation constant," also referred to as "$K_d$," refers to a quantity expressing the extent to which a particular substance separates into individual components (e.g., the protein carrier, antibody, and optional therapeutic agent).

The terms "lyophilized," "lyophilization" and the like as used herein refer to a process by which the material (e.g., nanoparticles) to be dried is first frozen and then the ice or frozen solvent is removed by sublimation in a vacuum environment. An excipient is optionally included in pre-lyophilized formulations to enhance stability of the lyophilized product upon storage. In some embodiments, the nanoparticles can be formed from lyophilized components (carrier protein, antibody and optional therapeutic agent) prior to use as a therapeutic. In other embodiments, the carrier protein, antibody, and optional therapeutic agent are first combined into nanoparticles and then lyophilized. The lyophilized sample may further contain additional excipients.

The term "bulking agents" comprise agents that provide the structure of the freeze-dried product. Common examples used for bulking agents include mannitol, glycine, lactose and sucrose. In addition to providing a pharmaceutically elegant cake, bulking agents may also impart useful qualities in regard to modifying the collapse temperature, providing freeze-thaw protection, and enhancing the protein stability over long-term storage. These agents can also serve as tonicity modifiers.

The term "buffer" encompasses those agents which maintain the solution pH in an acceptable range prior to lyophilization and may include succinate (sodium or potassium), histidine, phosphate (sodium or potassium), Tris (tris(hydroxymethyl)aminomethane), diethanolamine, citrate (sodium) and the like. The buffer of this invention has a pH in the range from about 5.5 to about 6.5; and preferably has a pH of about 6.0. Examples of buffers that will control the pH in this range include succinate (such as sodium succinate), gluconate, histidine, citrate and other organic acid buffers.

The term "cryoprotectants" generally includes agents which provide stability to the protein against freezing-induced stresses, presumably by being preferentially excluded from the protein surface. They may also offer protection during primary and secondary drying, and long-term product storage. Examples are polymers such as dextran and polyethylene glycol; sugars such as sucrose, glucose, trehalose, and lactose; surfactants such as polysorbates; and amino acids such as glycine, arginine, and serine.

The term "lyoprotectant" includes agents that provide stability to the protein during the drying or 'dehydration' process (primary and secondary drying cycles), presumably by providing an amorphous glassy matrix and by binding with the protein through hydrogen bonding, replacing the water molecules that are removed during the drying process. This helps to maintain the protein conformation, minimize protein degradation during the lyophilization cycle and improve the long-term products. Examples include polyols or sugars such as sucrose and trehalose.

The term "pharmaceutical formulation" refers to preparations which are in such form as to permit the active ingredients to be effective, and which contains no additional components which are toxic to the subjects to which the formulation would be administered.

"Pharmaceutically acceptable" excipients (vehicles, additives) are those which can reasonably be administered to a subject mammal to provide an effective dose of the active ingredient employed.

"Reconstitution time" is the me that is required to rehydrate a lyophilized formulation with a solution to a particle-free clarified solution.

A "stable" formulation is one in which the protein therein essentially retains its physical stability and/or chemical stability and/or biological activity upon storage.

The term "epitope" as used herein refers to the portion of an antigen which is recognized by an antibody. Epitopes include, but are not limited to, a short amino acid sequence or peptide (optionally glycosylated or otherwise modified) enabling a specific interaction with a protein (e.g., an antibody) or ligand. For example, an epitope may be a part of a molecule to which the antigen-binding site of an antibody attaches.

The term "treating" or "treatment" covers the treatment of a disease or disorder (e.g., cancer), in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. In some embodiments "treating" or "treatment" refers to the killing of cancer cells.

The term "kill" with respect to a cancer treatment is directed to include any type of manipulation that will lead to the death of that cancer cell or at least of portion of a population of cancer cells.

Additionally, some terms used in this specification are more specifically defined below.

Overview

The current invention is predicated, in part, on the surprising discovery that optionally lyophilized nanoparticles comprising a carrier protein, an antibody, and a therapeutic agent provide targeted therapy to a tumor while minimizing toxicity to the patient. The nanoparticles as described herein are thus a significant improvement versus conventional ADCs.

For conventional ADCs to be effective, it is critical that the linker be stable enough not to dissociate in the systemic circulation but allow for sufficient drug release at the tumor site. Alley, S. C., et al. (2008) *Bioconjug Chem* 19:759-765. This has proven to be a major hurdle in developing effective drug conjugate (Julien, D. C., et al. (2011) *MAbs* 3:467-478; Alley, S. C., et al. (2008) *Bioconjug Chem* 19:759-765); therefore, an attractive feature of the nano-immune conjugate is that a biochemical linker is not required.

Another shortcoming of current ADCs is that higher drug penetration into the tumor has not been substantively proven in human tumors. Early testing of ADCs in mouse models suggested that tumor targeting with antibodies would result in a higher concentration of the active agent in the tumor (Deguchi, T. et al. (1986) *Cancer Res* 46: 3751-3755); however, this has not correlated in the treatment of human disease, likely because human tumors are much more heterogeneous in permeability than mouse tumors. Jain, R. K. et al. (2010) *Nat Rev Clin Oncol* 7:653-664. Also, the size of the nanoparticle is critical for extravasation from the vasculature into the tumor. In a mouse study using a human colon adenocarcinoma xenotransplant model, the vascular pores were permeable to liposomes up to 400 nm. Yuan, F., et al. (1995) *Cancer Res* 55: 3752-3756. Another study of tumor pore size and permeability demonstrated that both characteristics were dependent on tumor location and growth status, with regressing tumors and cranial tumors permeable to particles less than 200 nm. Hobbs, S. K., et al. (1998) *Proc Natl Acad Sci USA* 95:4607-4612. The nano-immune conjugate described herein overcomes this issue by the fact that the large complex, which is less than 200 nm intact, is partially dissociated in systemic circulation into smaller functional units that are easily able to permeate tumor tissue. Furthermore, once the conjugate arrives to the tumor site, the smaller toxic payload can be released and only the toxic portion needs to be taken up by tumor cells, not the entire conjugate.

The advent of antibody- (i.e. AVASTIN®) coated albumin nanoparticles containing a therapeutic agent (i.e., ABRAX-ANE®) has led to a new paradigm of directional delivery of two or more therapeutic agents to a predetermined site in vivo. See PCT Patent Publication Nos. WO 2012/154861 and WO 2014/055415, each of which is incorporated herein by reference in its entirety.

When compositions of albumin and an antibody are admixed together in an aqueous solution at specific concentrations and ratios, the antibodies spontaneously self-assemble into and onto the albumin to form nanoparticles having multiple copies of the antibody (up to 500 or more). Without being limited to any theory, it is contemplated that the antigen receptor portion of the antibody is positioned outward from the nanoparticle while the hydrophobic tail in integrated into the albumin by hydrophobic-hydrophobic interactions.

While protein compositions comprising a single source protein are commonly stored in lyophilized form where they exhibit significant shelf-life, such lyophilized compositions do not contain a self-assembled nanoparticle of two different proteins integrated together by hydrophobic-hydrophobic interactions. Moreover, the nanoparticle configuration wherein a majority of the antibody binding portions are exposed on the surface of the nanoparticles lends itself to being susceptible to dislodgement or reconfiguration by conditions which otherwise would be considered benign. For example, during lyophilization, ionic charges on the proteins are dehydrated thereby exposing the underlying charges. Exposed charges allow for charge-charge interactions between the two proteins which can alter the binding affinity of each protein to the other. In addition, the concentration of the nanoparticles increases significantly as the solvent (e.g., water) is removed. Such increased concentrations of nanoparticles could lead to irreversible oligomerization. Oligomerization is a known property of proteins that reduces the biological properties of the oligomer as compared to the monomeric form and increases the size of the particle sometimes beyond 1 micron.

On the other hand, a stable form of a nanoparticle composition is required for clinical and/or commercial use where a shelf-life of at least 3 months is required and shelf-lives of greater than 6 months or 9 months are preferred. Such a stable composition must be readily available for intravenous injection, must retain its self-assembled form upon intravenous injection so as to direct the nanoparticle to the predetermined site in vivo, must have a maximum size of less than 1 micron so as to avoid any ischemic event when delivered into the blood stream, and finally must be compatible with the aqueous composition used for injection.

Compounds

As will be apparent to the skilled artisan upon reading this disclosure, the present disclosure relates to compositions of nanoparticles containing a carrier protein, antibodies, and optionally at least one therapeutic agent, wherein said compositions are optionally lyophilized.

In some embodiments, the carrier protein can be albumin, gelatin, elastin (including topoelastin) or elastin-derived polypeptides (e.g., α-elastin and elastin-like polypeptides (ELPs)), gliadin, legumin, zein, soy protein (e.g., soy protein isolate (SPI)), milk protein (e.g., β-lactoglobulin (BLG) and casein), or whey protein (e.g., whey protein concentrates (WPC) and whey protein isolates (WPI)). In preferred embodiments, the carrier protein is albumin. In preferred embodiments, the albumin is egg white (ovalbumin), bovine serum albumin (BSA), or the like. In even more preferred embodiments, the carrier protein is human serum albumin (HSA). In some embodiments, the carrier protein is a generally regarded as safe (GRAS) excipient approved by the United States Food and Drug Administration (FDA).

In some embodiments, the antibodies are selected from the group consisting of ado-trastuzumab emtansine, alemtuzumab, bevacizumab, cetuximab, denosumab, dinutuximab, ipilimumab, nivolumab, obinutuzumab, ofatumumab, panitumumab, pembrolizumab, pertuzumab, rituximab, and trastuzumab. In some embodiments, the antibodies are a substantially single layer of antibodies on all or part of the surface of the nanoparticle.

Table 1 depicts a list of non-limiting list of antibodies.

TABLE 1

| | Antibodies Antibodies | |
|---|---|---|
| | Biologic | Treatment(s)/Target(s) |
| Monoclonal antibodies (MAbs) | Rituximab (Rituxan ®) Alemtuzumab (Campath ®) | Non-Hodgkin lymphoma Chronic lymphocytic leukemia (CLL) |

TABLE 1-continued

| Antibodies | |
|---|---|
| Biologic | Treatment(s)/Target(s) |
| Ipilimumab (Yervoy ®) | Metastatic melanoma |
| Bevacizumab (Avastin ®) | Colon cancer, lung cancer, renal cancer, ovarian cancer, glioblastoma multiforme |
| Cetuximab (Erbitux ®) | Colorectal cancer, non-small cell lung cancer, head and neck cancer, cervical cancer, glioblastoma, ovarian epithelia, fallopian tube or primary peritoneal cancer, renal cell cancer |
| Panitumumab (Vectibix ®) | Colorectal cancer |
| Trastuzumab (Herceptin ®) | Breast cancer, Adenocarcinoma |
| $^{90}$Y-ibritumomab tiuxetan (Zevalin ®) | Non-Hodgkin lymphoma |
| Ado-trastuzumab emtansine (Kadycla ®, also called TDM-1) | Breast cancer |
| Brentuximab vedotin (Adcetris ®) | Hodgkin lymphoma, Anaplastic large cell lymphoma |
| Blinatumomab (Blincyto) | Acute lymphocytic leukemia (ALL) |
| Pembrolizumab (Keytruda ®) | PD-1 (melanoma, non-small cell lung cancer) |
| Nivolumab (Opdivo ®) | PD-1 (melanoma, non-small cell lung cancer) |
| Ofatumumab (Arzerra ®) | Chronic lymphocytic leukemia (CLL) |
| Pertuzumab (Perjeta ®) | Breast cancer |
| Obinutuzumab (Gazyva ®) | Lymphoma |
| Dinutuximab (Unituxin ®) | Neuroblastoma |
| Denosumab (Prolia ®) | Bone metastases, multiple myeloma, giant cell tumor of bone |

In some embodiments, the at least one therapeutic agent is selected from the group consisting of abiraterone, bendamustine, bortezomib, carboplatin, cabazitaxel, cisplatin, chlorambucil, dasatinib, docetaxel, doxorubicin, epirubicin, erlotinib, etoposide, everolimus, gefitinib, idarubicin, imatinib, hydroxyurea, imatinib, lapatinib, leuprorelin, melphalan, methotrexate, mitoxantrone, nedaplatin, nilotinib, oxaliplatin, paclitaxel, pazopanib, pemetrexed, picoplatin, romidepsin, satraplatin, sorafenib, vemurafenib, sunitinib, teniposide, triplatin, vinblastine, vinorelbine, vincristine, and cyclophosphamide.

Table 2 depicts a list of non-limiting list of cancer therapeutic agents.

TABLE 2

| Cancer therapeutic agents | |
|---|---|
| Cancer Drugs | |
| Drug | Target(s) |
| Abitrexate (Methotrexate) | Acute lymphoblastic leukemia; breast cancer; gestational trophoblastic disease, head and neck cancer; lung cancer; mycosis fungoides; non-Hodgkin lymphoma; osteosarcoma |
| Abraxane (Paclitaxel Albumin-stabilized Nanoparticle Formulation) | Breast cancer; non-small cell lung cancer; pancreatic cancer |
| ABVD (Adriamycin, bleomycin, vinblastine sulfate, dacarbazine) | Hodgkin lymphoma |
| ABVE (Adriamycin, bleomycin, vincristine sulfate, etoposide) | Hodgkin lymphoma (in children) |
| ABVE-PC (Adriamycin, bleomycin, vincristine sulfate, etoposide, prednisone, cyclophosphamide) | Hodgkin lymphoma (in children) |
| AC (Adriamycin cyclophosphamide) | Breast cancer |
| AC-T (Adriamycin, cylclophosphamide, Taxol) | Breast cancer |
| Adcetris (Brentuximab Vedotin) | Anaplastic large cell lymphoma; Hodgkin lymphoma |
| ADE (Cytarabine (Ara-C), Daunorubicin Hydrochloride, Etoposide) | Acute myeloid leukemia (in children) |
| Ado-Trastuzumab Emtansine | Breast cancer |

TABLE 2-continued

Cancer therapeutic agents
Cancer Drugs

| Drug | Target(s) |
|---|---|
| Adriamycin (Doxorubicin Hydrochloride) | Acute lymphoblastic leukemia; acute myeloid leukemia; breast cancer, gastric (stomach) cancer; Hodgkin lymphoma; neuroblastoma; non-Hodgkin lymphoma; ovarian cancer; small cell lung cancer; soft tissue and bone sarcomas; thyroid cancer; transitional cell bladder cancer; Wilms tumor |
| Adrucil (Fluorouracil) | Basal cell carcinoma; breast cancer; colorectal cancer; gastric (stomach) adenocarcinoma; pancreatic cancer; squamous cell carcinoma of the head and neck |
| Afatinib Dimaleate | Non-small cell lung cancer |
| Afinitor (Everolimus) | Breast cancer, pancreatic cancer; renal cell carcinoma; subependymal giant cell astrocytoma |
| Alimta (Pemetrexed Disodium) | Malignant pleural mesothelioma; non-small cell lung cancer |
| Ambochlorin (Chlorambucil) | Chronic lymphocytic leukemia; Hodgkin lymphoma; non-Hodgkin lymphoma |
| Anastrozole | Breast cancer |
| Aredia (Pamidronate Disodium) | Breast cancer; multiple myeloma |
| Arimidex (Anastrozole) | Breast cancer |
| Aromasin (Exemestane) | Advanced breast cancer; early-stage breast cancer and estrogen receptor positive |
| Arranon (Nelarabine) | T-cell acute lymphoblastic leukemia; T-cell lymphoblastic lymphoma |
| Azacitidine | Myelodysplastic syndromes |
| BEACOPP | Hodgkin lymphoma |
| Becenum (Carmustine) | Brain tumors; Hodgkin lymphoma; multiple myeloma; non-Hodgkin lymphoma |
| Beleodaq (Belinostat) | Peripheral T-cell lymphoma |
| BEP | Ovarian germ cell tumors; testicular germ cell tumors |
| Bicalutamide | Prostate cancer |
| BiCNU (Carmustine) | Brain tumors; Hodgkin lymphoma; multiple myeloma; non-Hodgkin lymphoma |
| Bleomycin | Hodgkin lymphoma; non-Hodgkin lymphoma; penile cancer; squamous cell carcinoma of the cervix; squamous cell carcinoma of the head and neck; squamous cell carcinoma of the vulva; testicular cancer |
| Bosulif (Bosutinib) | Chronic myelogenous leukemia |
| Brentuximab Vedotin | Anaplastic large cell lymphoma; Hodgkin lymphoma |
| Busulfan | Chronic myelogenous leukemia |
| Busulfex (Busulfan) | Chronic myelogenous leukemia |
| Cabozantinib-S-Malate | Medullary thyroid cancer |
| CAF | Breast cancer |
| Camptosar (Irinotecan Hydrochloride) | Colorectal cancer |
| CAPOX | Colorectal cancer |
| Carfilzomib | Multiple myeloma |
| Casodex (Bicalutamide) | Prostate cancer |
| CeeNU (Lomustine) | Brain tumors; Hodgkin lymphoma |
| Ccritinib | Non-small cell lung cancer |
| Cerubidine (Daunorubicin Hydrochloride) | Acute lymphoblastic leukemia; acute myeloid leukemia |
| Chlorambucil | Chronic lymphocytic leukemia; Hodgkin lymphoma; non-Hodgkin lymphoma |
| CHLORAMBUCIL-PREDNISONE | Chronic lymphocytic leukemia |
| CHOP | Non-Hodgkin lymphoma |
| Cisplatin | Bladder cancer; cervical cancer; malignant mesothelioma; non-small cell lung cancer; ovarian cancer; squamous cell carcinoma of the head and neck; testicular cancer |
| Clafen (Cyclophosphamide) | Acute lymphoblastic leukemia; acute myeloid leukemia; breast cancer; chronic lymphocytic leukemia; chronic myelogenous leukemia; Hodgkin lymphoma; multiple myeloma; mycosis fungoides; neuroblastoma; non-Hodgkin lymphoma; ovarian cancer; retinoblastoma |
| Clofarex (Clofarabine) | Acute lymphoblastic leukemia |
| CMF | Breast cancer |
| Cometriq (Cabozantinib-S-Malate) | Medullary thyroid cancer |
| COPP | Hodgkin lymphoma; non-Hodgkin lymphoma |

TABLE 2-continued

Cancer therapeutic agents
Cancer Drugs

| Drug | Target(s) |
| --- | --- |
| COPP-ABV | Hodgkin lymphoma |
| Cosmegen (Dactinomycin) | Ewing sarcoma; gestational trophoblastic disease; rhabdomyosarcoma; solid tumors; testicular cancer; Wilms tumor |
| CVP | Non-Hodgkin lymphoma; chronic lymphocytic leukemia |
| Cyclophosphamide | Acute lymphoblastic leukemia; acute myeloid leukemia; breast cancer; chronic lymphocytic leukemia; chronic myelogenous leukemia; Hodgkin lymphoma; multiple myeloma; mycosis fungoides; neuroblastoma; non-Hodgkin lymphoma; ovarian cancer; retinoblastoma. |
| Cyfos (Ifosfamide) | Testicular germ cell tumors |
| Cyramza (Ramucirumab) | Adenocarcinoma; colorectal cancer; non-small cell lung cancer |
| Cytarabine | Acute lymphoblastic leukemia; acute myeloid leukemia; chronic myelogenous leukemia; meningeal leukemia |
| Cytosar-U (Cytarabine) | Acute lymphoblastic leukemia; acute myeloid leukemia; chronic myelogenous leukemia; meningeal leukemia |
| Cytoxan (Cyclophosphamide) | Acute lymphoblastic leukemia; acute myeloid leukemia; breast cancer; chronic lymphocytic leukemia; chronic myelogenous leukemia; Hodgkin lymphoma; multiple myeloma; mycosis fungoides; neuroblastoma; non-Hodgkin lymphoma; ovarian cancer; retinoblastoma |
| Dacarbazine | Hodgkin lymphoma; melanoma |
| Dacogen (Decitabine) | Myelodysplastic syndromes |
| Dactinomycin | Ewing sarcoma; gestational trophoblastic disease; rhabdomyosarcoma; solid tumors; testicular cancer; Wilms tumor |
| Daunorubicin Hydrochloride | Acute lymphoblastic leukemia; acute myeloid leukemia |
| Degarelix | Prostate cancer |
| Denileukin Diftitox | Cutaneous T-cell lymphoma |
| Denosumab | Giant cell tumor of the bone; breast cancer, prostate cancer |
| DepoCyt (Liposomal Cytarabine) | Lymphomatous meningitis |
| DepoFoam (Liposomal Cytarabine) | Lymphomatous meningitis |
| Docetaxel | Breast cancer; adenocarcinoma of the stomach or gastroesophageal junction; non-small cell lung cancer; prostate cancer; squamous cell carcinoma of the head and neck |
| Doxil (Doxorubicin Hydrochloride Liposome) | AIDS-related Kaposi sarcoma; multiple myeloma; ovarian cancer |
| Doxorubicin Hydrochloride | Acute lymphoblastic leukemia; acute myeloid leukemia; breast cancer; gastric (stomach) cancer; Hodgkin lymphoma; neuroblastoma; non-Hodgkin lymphoma; ovarian cancer; small cell lung cancer; soft tissue and bone sarcomas; thyroid cancer; transitional cell bladder cancer; Wilms tumor. |
| Dox-SL (Doxorubicin Hydrochloride Liposome) | AIDS-related Kaposi sarcoma; multiple myeloma; ovarian cancer |
| DTIC-Dome (Dacarbazine) | Hodgkin lymphoma; melanoma |
| Efudex (Fluorouracil) | Basal cell carcinoma; breast cancer; colorectal cancer; gastric (stomach) adenocarcinoma; pancreatic cancer; squamous cell carcinoma of the head and neck |
| Ellence (Epirubicin Hydrochloride) | Breast cancer |
| Eloxatin (Oxaliplatin) | Colorectal cancer; stage III colon cancer |
| Emend (Aprepitant) | Nausea and vomiting caused by chemotherapy and nausea and vomiting after surgery |
| Enzalutamide | Prostate cancer |
| Epirubicin Hydrochloride | Breast cancer |
| EPOCH | Non-Hodgkin lymphoma |
| Erbitux (Cetuximab) | Colorectal cancer; squamous cell carcinoma of the head and neck |
| Eribulin Mesylate | Breast cancer |
| Erivedge (Vismodegib) | Basal cell carcinoma |
| Erlotinib Hydrochloride | Non-small cell lung cancer; pancreatic cancer |

TABLE 2-continued

Cancer therapeutic agents
Cancer Drugs

| Drug | Target(s) |
|---|---|
| Erwinaze (Asparaginase *Erwinia chrysanthemi*) | Acute lymphoblastic leukemia |
| Etopophos (Etoposide Phosphate) | Small cell lung cancer; testicular cancer |
| Evacet (Doxorubicin Hydrochloride Liposome) | AIDS-related Kaposi sarcoma; multiple myeloma; ovarian cancer |
| Everolimus | Breast cancer; pancreatic cancer; renal cell carcinoma; subependymal giant cell astrocytoma |
| Evista (Raloxifene Hydrochloride) | Breast cancer |
| Exemestane | Breast cancer |
| Fareston (Toremifene) | Breast cancer |
| Farydak (Panobinostat) | Multiple myeloma |
| Faslodex (Fulvestrant) | Breast cancer |
| FEC | Breast cancer |
| Femara (Letrozole) | Breast cancer |
| Filgrastim | Neutropenia |
| Fludara (Fludarabine Phosphate) | Chronic lymphocytic leukemia |
| Fluoroplex (Fluorouracil) | Basal cell carcinoma; breast cancer; colorectal cancer; gastric (stomach) adenocarcinoma; pancreatic cancer; squamous cell carcinoma of the head and neck |
| Folex (Methotrexate) | Acute lymphoblastic leukemia; breast cancer; gestational trophoblastic disease; head and neck cancer; lung cancer; mycosis fungoides; non-Hodgkin lymphoma; osteosarcoma |
| FOLFIRI | Colorectal cancer |
| FOLFIRI-BEVACIZUMAB | Colorectal cancer |
| FOLFIRI-CETUXIMAB | Colorectal cancer |
| FOLFIRINOX | Pancreatic cancer |
| FOLFOX | Colorectal cancer |
| Folotyn (Pralatrexate) | Peripheral T-cell lymphoma |
| FU-LV | Colorectal cancer; esophageal cancer; gastric cancer |
| Fulvestrant | Breast cancer |
| Gefitinib | Non-small cell lung cancer |
| Gemcitabine Hydrochloride | Breast cancer; non-small cell lung cancer; ovarian cancer; pancreatic cancer |
| GEMCITABINE-CISPLATIN | Biliary tract cancer; bladder cancer; cervical cancer; malignant mesothelioma; non-small cell lung cancer; ovarian cancer; pancreatic cancer |
| GEMCITABINE-OXALIPLATIN | Pancreatic cancer |
| Gemtuzumab Ozogamicin (antibody drug conjugate) | Acute myeloid leukemia |
| Gemzar (Gemcitabine Hydrochloride) | Breast cancer; non-small cell lung cancer; ovarian cancer; pancreatic cancer |
| Gilotrif (Afatinib Dimaleate) | Non-small cell lung cancer |
| Gleevec (Imatinib Mesylate) | Acute lymphoblastic leukemia; chronic eosinophilic leukemia or hypereosinophilic syndrome; chronic myelogenous leukemia; dermatofibrosarcoma protuberans; gastrointestinal stromal tumor; myelodysplastic/myeloproliferative neoplasms; systemic mastocytosis. |
| Gliadel (Carmustine Implant) | Glioblastoma multiforme; malignant glioma |
| Goserelin Acetate | Breast cancer; prostate cancer |
| Halaven (Eribulin Mesylate) | Breast cancer |
| Hycamtin (Topotecan Hydrochloride) | Cervical cancer; ovarian cancer; small cell lung cancer |
| Hyper-CVAD | Acute lymphoblastic leukemia; non-Hodgkin lymphoma |
| Ibrance (Palbociclib) | Breast cancer |
| Ibrutinib | Chronic lymphocytic leukemia; mantel cell lymphoma; |
| ICE | Hodgkin lymphoma; non-Hodgkin lymphoma |
| Iclusig (Ponatinib Hydrochloride) | Acute lymphoblastic leukemia; Chronic myelogenous leukemia |
| Idamycin (Idarubicin Hydrochloride) | Acute myeloid leukemia |
| Imatinib Mesylate | Acute lymphoblastic leukemia; chronic eosinophilic leukemia or hypereosinophilic syndrome; chronic myelogenous leukemia; dermatofibrosarcoma protuberans; gastrointestinal stromal tumor; myelodysplastic/myeloproliferative neoplasms; systemic mastocytosis. |

TABLE 2-continued

Cancer therapeutic agents
Cancer Drugs

| Drug | Target(s) |
| --- | --- |
| Imbruvica (Ibrutinib) | Chronic lymphocytic leukemia; mantle cell lymphoma; Waldenström macroglobulinemia |
| Inlyta (Axitinib) | Renal cell carcinoma |
| Iressa (Gefitinib) | Non-small cell lung cancer |
| Irinotecan Hydrochloride | Colorectal cancer |
| Istodax (Romidepsin) | Cutaneous T-cell lymphoma |
| Ixempra (Ixabepilone) | Breast cancer |
| Jevtana (Cabazitaxel) | Prostate cancer |
| Keoxifene (Raloxifene Hydrochloride) | Breast cancer |
| Kyprolis (Carfilzomib) | Multiple myeloma |
| Lenvima (Lenvatinib Mesylate) | Thyroid cancer |
| Letrozole | Breast cancer |
| Leucovorin Calcium | Colorectal cancer |
| Leukeran (Chlorambucil) | Chronic lymphocytic leukemia; Hodgkin lymphoma; non-Hodgkin lymphoma |
| Leuprolide Acetate | Prostate cancer |
| Linfolizin (Chlorambucil) | Chronic lymphocytic leukemia; Hodgkin lymphoma; non-Hodgkin lymphoma |
| LipoDox (Doxorubicin Hydrochloride Liposome) | AIDS-related Kaposi sarcoma; multiple myeloma; ovarian cancer |
| Lomustine | Brain tumors; Hodgkin lymphoma |
| Lupron (Leuprolide Acetate) | Prostate cancer |
| Lynparza (Olaparib) | Ovarian cancer |
| Marqibo (Vincristine Sulfate Liposome) | Acute lymphoblastic leukemia |
| Matulane (Procarbazine Hydrochloride) | Hodgkin lymphoma |
| Mechlorethamine Hydrochloride | Bronchogenic carcinoma; chronic lymphocytic leukemia; chronic myelogenous leukemia; Hodgkin lymphoma; malignant pleural effusion, malignant pericardial effusion, and malignant peritoneal effusion; mycosis fungoides; non-Hodgkin lymphoma |
| Megace (Megestrol Acetate) | Breast cancer; endometrial cancer |
| Mekinist (Trametinib) | Melanoma |
| Mercaptopurine | Acute lymphoblastic leukemia |
| Mesnex (Mesna) | Hemorrhagic cystitis |
| Methazolastone (Temozolomide) | Anaplastic astrocytoma; glioblastoma multiforme |
| Mexate (Methotrexate) | Acute lymphoblastic leukemia; breast cancer; gestational trophoblastic disease; head and neck cancer; lung cancer; mycosis fungoides; non-Hodgkin lymphoma; osteosarcoma |
| Mexate-AQ (Methotrexate) | Acute lymphoblastic leukemia; breast cancer; gestational trophoblastic disease; head and neck cancer; lung cancer; mycosis fungoides; non-Hodgkin lymphoma; osteosarcoma |
| Mitoxantrone Hydrochloride | Acute myeloid leukemia; prostate cancer |
| Mitozytrex (Mitomycin C) | Gastric (stomach) and pancreatic adenocarcinoma |
| MOPP | Hodgkin lymphoma |
| Mozobil (Plerixafor) | Multiple myeloma; non-Hodgkin lymphoma |
| Mustargen (Mechlorethamine Hydrochloride) | Bronchogenic carcinoma; chronic lymphocytic leukemia; chronic myelogenous leukemia; Hodgkin lymphoma; malignant pleural effusion, malignant pericardial effusion, and malignant peritoneal effusion; mycosis fungoides; non-Hodgkin lymphoma |
| Myleran (Busulfan) | Chronic myelogenous leukemia |
| Mylotarg (Gemtuzumab Ozogamicin) | Acute myeloid leukemia |
| Nanoparticle Paclitaxel (Paclitaxel Albumin-stabilized Nanoparticle Formulation) | Breast cancer; Non-small cell lung cancer; Pancreatic cancer |
| Navelbine (Vinorelbine Tartrate) | Non-small cell lung cancer |
| Nelarabine | T-cell acute lymphoblastic leukemia |
| Neosar (Cyclophosphamide) | Acute lymphoblastic leukemia; Acute myeloid leukemia; Breast cancer; Chronic lymphocytic leukemia; Chronic myelogenous leukemia; Hodgkin lymphoma; Multiple myeloma; Mycosis fungoides; Neuroblastoma; Non-Hodgkin lymphoma; Ovarian cancer; Retinoblastoma |
| Nexavar (Sorafenib Tosylate) | Hepatocellular carcinoma; Renal cell carcinoma; Thyroid cancer |
| Nilotinib | Chronic myelogenous leukemia |
| Nivolumab | Melanoma; Squamous non-small cell lung cancer |
| Nolvadex (Tamoxifen Citrate) | Breast cancer |

TABLE 2-continued

Cancer therapeutic agents
Cancer Drugs

| Drug | Target(s) |
| --- | --- |
| Odomzo (Sonidegib) | Basal cell carcinoma |
| OEPA | Hodgkin lymphoma |
| OFF | Pancreatic cancer |
| Olaparib | Ovarian cancer |
| Oncaspar (Pegaspargase) | Acute lymphoblastic leukemia |
| OPPA | Hodgkin lymploma |
| Oxaliplatin | Colorectal cancer; Stage III colon cancer |
| Paclitaxel | AIDS-related Kaposi sarcoma; Breast cancer; Non-small cell lung cancer; Ovarian cancer |
| Paclitaxel Albumin-stabilized Nanoparticle Formulation | Breast cancer; Non-small lung cancer; Pancreatic cancer |
| PAD | Multiple myeloma |
| Palbociclib | Breast cancer |
| Pamidronate Disodium | Breast cancer; Multiple myeloma |
| Panitumumab | Colorectal cancer |
| Panobinostat | Multiple myeloma |
| Paraplat (Carboplatin) | Non-small cell lung cancer; Ovarian cancer |
| Paraplatin (Carboplatin) | Non-small cell lung cancer; Ovarian cancer |
| Pazopanib Hydrochloride | Renal cell carcinoma; Soft tissue sarcoma |
| Pegaspargase | Acute lymphoblastic leukemia |
| Pemetrexed Disodium | Malignant pleural mesothelioma; Non-small cell lung cancer |
| Platinol (Cisplatin) | Bladder cancer; Cervical cancer; Malignant mesothelioma; Non-small cell lung cancer; Ovarian cancer; Squamous cell carcinoma of the head and neck; Testicular cancer |
| Platinal-AQ (Cisplatin) | Bladder cancer; Cervical cancer; Malignant mesothelioma; Non-small cell lung cancer; Ovarian cancer; Squamous cell carcinoma of the head and neck; Testicular cancer |
| Plerixafor | Multiple myeloma; Non-Hodgkin lymphoma |
| Pomalidomide | Multiple myeloma |
| Pomalyst (Pomalidomide) | Multiple myeloma |
| Pontinib Hydrochloride | Acute lymphoblastic leukemia; Chronic myelogenous leukemia |
| Pralatrexate | Peripheral T-cell lymphoma |
| Prednisone | Acute lymphoblastic leukemia; Chronic lymphocytic leukemia; Hodgkin lymphoma; Multiple myeloma; Non-Hodgkin lymphoma; Prostate cancer; Thymoma and thymic carcinoma |
| Procarbazine Hydrochloride | Hodgkin lymphoma |
| Provenge (Sipuleucel-T) | Prostate cancer |
| Purincthol (Mercaptopurine) | Acute lymphoblastic leukemia |
| Radium 223 Dichloride | Prostate cancer |
| Raloxifene Hydrochloride | Breast cancer |
| R-CHOP | Non-Hodgkin lymphoma |
| R-CVP | Non-Hodgkin lymphoma |
| Regorafenib | Colorectal cancer; Gastrointestinal stromal tumor |
| R-EPOCH | B-cell non-Hodgkin lymphoma |
| Revlimid (Lenalidomide) | Mantle cell lymphoma; Multiple myeloma; Anemia |
| Rheumatrex (Methotrexate) | Acute lymphoblastic leukemia; Breast cancer; Gestational trophoblastic disease; Head and neck cancer; Lung cancer; Non-Hodgkin lymphoma; Osteosarcoma |
| Romidepsin | Cutaneous T-cell lymphoma |
| Rubidomycin (Daunorubicin Hydrochloride) | Acute lymphoblastic leukemia; Acute myeloid leukemia |
| Sipuleucel-T | Prostate cancer |
| Somatuline Depot (Lanreotide Acetate) | Gastroenteropancreatic neuroendocrine tumors |
| Sonidegib | Basal cell carcinoma |
| Sorafenib Tosylate | Hepatocellular carcinoma; Renal cell carcinoma; Thyroid cancer |
| Sprycel (Dasatinib) | Acute lymphoblastic leukemia; Chronic myelogenous leukemia |
| STANFORD V | Hodgkin lymphoma |
| Stivarga (Regorafenib) | Colorectal cancer; Gastrointestinal stromal tumor |
| Sunitnib Malate | Gastronintestinal stromal tumor; Pancreatic cancer; Renal cell carcinoma |
| Sutent (Sunitinib Malate) | Gastrointestinal stromal tumor; Pancreatic cancer; Renal cell carcinoma |
| Synovir (Thalidomide) | Multiple myeloma |

TABLE 2-continued

Cancer therapeutic agents
Cancer Drugs

| Drug | Target(s) |
| --- | --- |
| Synribo (Omacetaxine Mepesuccinate) | Chronic myelogenous leukemia |
| TAC | Breast cancer |
| Tafinlar (Dabrafenib) | Melanoma |
| Tamoxifen Citrate | Breast cancer |
| Tarabine PFS (Cytarabine) | Acute lymphoblastic leukemia; Acute myeloid leukemia; Chronic myelogenous leukemia |
| Tarceva (Erlotinib Hydrochloride) | Non-small cell lung cancer; Pancreatic cancer |
| Targretin (Bexarotene) | Skin problems caused by cutaneous T-cell lymphoma |
| Tasigna (Niltinib) | Chronic myelogenous leukemia |
| Taxol (Paclitaxel) | AIDS-related Kaposi sarcoma; Breast cancer; Non-small cell lung cancer; Ovarian cancer |
| Taxotere (Docetaxel) | Breast cancer; Adenocarcinoma; Non-small cell lung cancer; Prostate cancer; Squamous cell carcinoma of the head and neck |
| Temodar (Temozolomide) | Anaplastic astrocytoma; Glioblastoma multiforme |
| Temozolomide | Anaplastic astrocytoma; Glioblastoma multiforme |
| Thiotepa | Bladder cancer; Breast cancer; Malignant pleural effusion, malignant pericardial effusion, and malignant peritoneal effusion; Ovarian cancer |
| Toposar (Etoposide) | Small cell lung cancer; Testicular cancer |
| Topotecan Hydrochloride | Cervical cancer; Ovarian cancer; Small cell lung cancer |
| Toremifene | Breast cancer |
| Torisel (Temsirolimus) | Renal cell carcinoma |
| TPF | Squamous cell carcinoma of the head and neck; Gastric (stomach) cancer |
| Trastuzumab | Adenocarcinoma; Breast cancer |
| Treanda (Bendamustine Hydrochloride) | B-cell non-Hodgkin lymphoma; Chronic lymphocytic leukemia |
| Trisenox (Arsenic Trioxide) | Acute promyelocytic leukemia |
| Tykerb (Lapatinib Ditosylate) | Breast cancer |
| Vandetabib | Medullary thyroid cancer |
| VAMP | Hodgkin lymphoma |
| VeIP | Ovarian germ cell; Testicular cancer |
| Velban (Vinblastine Sulfate) | Breast cancer; Choriocarcinoma; Hodgkin lymphoma; Kaposi sarcoma; Mycosid fungoides; Non-Hodgkin lymphoma; Testicular cancer |
| Velcade (Bortezomib) | Mulitple myeloma; Mantle cell lymphoma |
| Velsar (Vinblastine Sulfate) | Breast cancer; Choriocarcinoma; Hodgkin lymphoma; Kaposi sarcoma; Mycosis fungoides; Non-Hodgkin lymphoma; Testicular cancer |
| VePesid (Etoposide) | Small cell lung cancer; Testicular cancer |
| Viadur (Leuprolide Acetate) | Prostate cancer |
| Vidaza (Azacitidine) | Myelodysplastic syndromes |
| Vincasar PFS (Vincristine Sulfate) | Acute leukemia; Hodgkin lymphoma; Neuroblastoma; Non-Hodgkin lymphoma; Rhabdomyosarcoma; Wilms tumor |
| Vincristine Sulfate Liposome | Acute lymphoblastic leukemia |
| Vinorelbine Tartrate | Non-small cell lung cancer |
| VIP | Testicular cancer |
| Visbodegib | Basal cell carcinoma |
| Voraxaze (Glucarpidase) | Toxic blood levels of the anticancer drug methotrexate |
| Votrient (Pazopanib Hydrochloride) | Renal cell carcinoma; Soft tissue sarcoma |
| Wellcovorin (Leucovorin Calcium) | Colorectal cancer; Anemia |
| Xalkori (Crizotinib) | Non-small cell lung cancer |
| Xeloda (Capecitabine) | Breast cancer; Colorectal cancer |
| XELIRI | Colorectal cancer; Esophageal cancer; Gastric (stomach) cancer |
| XELOX | Colorectal cancer |
| Xofigo (Radium 223 Dichloride) | Prostate cancer |
| Xtandi (Enzalutamide) | Prostate cancer |
| Zaltrap (Ziv-Aflibercept) | Colorectal cancer |
| Zelboraf (Vemurafenib) | Melanoma |
| Ziv-Aflibercept | Colorectal cancer |
| Zoladex (Goserelin Acetate) | Breast cancer; Prostate cancer |
| Zolinza (Vorinostat) | Cutaneous T-cell lymphoma |
| Zometa (Zoledronic Acid) | Multiple myeloma |

TABLE 2-continued

Cancer therapeutic agents
Cancer Drugs

| Drug | Target(s) |
|---|---|
| Zydelig (Idelalisib) | Chronic lymphocytic leukemia; Non-Hodgkin lymphoma (Follicula B-cell non Hodgkin lymphoma and Small lymphocytic lymphoma) |
| Zykadia (Certinib) | Non-small cell lung cancer |
| Zytiga (Abiraterone Acetate) | Prostate cancer |

It is to be understood that the therapeutic agent may be located inside the nanoparticle, on the outside surface of the nanoparticle, or both. The nanoparticle may contain more than one therapeutic agent, for example, two therapeutic agents, three therapeutic agents, four therapeutic agents, five therapeutic agents, or more. Furthermore, a nanoparticle may contain the same or different therapeutic agents inside and outside the nanoparticle.

In some embodiments any carrier protein, antibody, therapeutic agent, or any combination thereof is expressly excluded. For example in some embodiments a composition may comprise any carrier protein and chemotherapeutic except Abraxane® and/or any targeting antibody except bevacizumab.

In one aspect, the nanoparticle comprises at least 100 antibodies non-covalently bound to the surface of the nanoparticle. In one aspect, the nanoparticle comprises at least 200 antibodies non-covalently bound to the surface of the nanoparticle. In one aspect, the nanoparticle comprises at least 300 antibodies non-covalently bound to the surface of the nanoparticle. In one aspect, the nanoparticle comprises at least 400 antibodies non-covalently bound to the surface of the nanoparticle. In one aspect, the nanoparticle comprises at least 500 antibodies non-covalently bound to the surface of the nanoparticle. In one aspect, the nanoparticle comprises at least 600 antibodies non-covalently bound to the surface of the nanoparticle.

In one aspect, the nanoparticle comprises between about 100 and about 1000 antibodies non-covalently bound to the surface of the nanoparticle. In one aspect, the nanoparticle comprises between about 200 and about 1000 antibodies non-covalently bound to the surface of the nanoparticle. In one aspect, the nanoparticle comprises between about 300 and about 1000 antibodies non-covalently bound to the surface of the nanoparticle. In one aspect, the nanoparticle comprises between about 400 and about 1000 antibodies non-covalently bound to the surface of the nanoparticle. In one aspect, the nanoparticle comprises between about 500 and about 1000 antibodies non-covalently bound to the surface of the nanoparticle. In one aspect, the nanoparticle comprises between about 600 and about 1000 antibodies non-covalently bound to the surface of the nanoparticle. In one aspect, the nanoparticle comprises between about 200 and about 800 antibodies non-covalently bound to the surface of the nanoparticle. In one aspect, the nanoparticle comprises between about 300 and about 800 antibodies non-covalently bound to the surface of the nanoparticle. In preferred embodiments, the nanoparticle comprises between about 400 and about 800 antibodies non-covalently bound to the surface of the nanoparticle. Contemplated values include any value or subrange within any of the recited ranges, including endpoints.

In one aspect, the average particle size in the nanoparticle composition is less than about 1 μm. In one aspect, the average particle size in the nanoparticle composition is between about 130 nm and about 1 μm. In one aspect, the average particle size in the nanoparticle composition is between about 130 nm and about 900 nm. In one aspect, the average particle size in the nanoparticle composition is between about 130 nm and about 800 nm. In one aspect, the average particle size in the nanoparticle composition is between about 130 nm and about 700 nm. In one aspect, the average particle size in the nanoparticle composition is between about 130 nm and about 600 nm. In one aspect, the average particle size in the nanoparticle composition is between about 130 nm and about 500 nm. In one aspect, the average particle size in the nanoparticle composition is between about 130 nm and about 400 nm. In one aspect, the average particle size in the nanoparticle composition is between about 130 nm and about 300 nm. In one aspect, the average particle size in the nanoparticle composition is between about 130 nm and about 200 nm. In a preferred embodiment, the average particle size in the nanoparticle composition is between about 150 nm and about 180 nm. In an especially preferred embodiment, the mean particle size in the nanoparticle composition is about 160 nm. Contemplated values include any value, subrange, or range within any of the recited ranges, including endpoints.

In one aspect, the nanoparticle composition is formulated for intravenous injection. In order to avoid an ischemic event, the nanoparticle composition formulated for intravenous injection should comprise nanoparticles with an average particle size of less than about 1 μm.

In one aspect, the average particle size in the nanoparticle composition is greater than about 1 μm. In one aspect, the average particle size in the nanoparticle composition is between about 1 μm and about 5 μm. In one aspect, the average particle size in the nanoparticle composition is between about 1 μm and about 4 μm. In one aspect, the average particle size in the nanoparticle composition is between about 1 μm and about 3 μm. In one aspect, the average particle size in the nanoparticle composition is between about 1 μm and about 2 μm. In one aspect, the average particle size in the nanoparticle composition is between about 1 μm and about 1.5 μm. Contemplated values include any value, subrange, or range within any of the recited ranges, including endpoints.

In one aspect, the nanoparticle composition is formulated for direct injection into a tumor. Direct injection includes injection into or proximal to a tumor site, perfusion into a tumor, and the like. When formulated for direct injection into a tumor, the nanoparticle may comprise any average particle size. Without being bound by theory, it is believed that larger particles (e.g., greater than 500 nm, greater than 1 μm, and the like) are more likely to be immobilized within the tumor, thereby providing a beneficial effect. Larger particles can accumulate in the tumor or specific organs. See, e.g., 20-60 micron glass particle that is used to inject into the hepatic artery feeding a tumor of the liver, called "TheraSphere®" (in clinical use for liver cancer). Therefore, for intravenous administration, particles under 1 μm are typically used. Particles over 1 μm are, more typically, administered directly into a tumor ("direct injection") or into an artery feeding into the site of the tumor.

In one aspect, less than about 0.01% of the nanoparticles within the composition have a particle size greater than 200 nm, greater than 300 nm, greater than 400 nm, greater than 500 nm, greater than 600 nm, greater than 700 nm, or greater than 800 nm. In one aspect, less than about 0.001% of the nanoparticles within the composition have a particle size greater than 200 nm, greater than 300 nm, greater than 400 nm, greater than 500 nm, greater than 600 nm, greater than 700 nm, or greater than 800 nm. In a preferred embodiment, less than about 0.01% of the nanoparticles within the composition have a particle size greater than 800 nm. In a more preferred embodiment, less than about 0.001% of the nanoparticles within the composition have a particle size greater than 800 nm.

In a preferred aspect, the sizes and size ranges recited herein relate to particle sizes of the reconstituted lyophilized nanoparticle composition. That is, after the lyophilized nanoparticles are resuspended in an aqueous solution (e.g., water, other pharmaceutically acceptable excipient, buffer, etc.), the particle size or average particle size is within the range recited herein.

In one aspect, at least about 50%, 60%, 70%, 80%, 90%, 95%, 96%, 97%, 98%, 99%, 99.5%, or 99.9% of the nanoparticles are present in the reconstituted composition as single nanoparticles. That is, fewer than about 50%, 40%, 30%, etc. of the nanoparticles are dimerized or multimerized (oligomerized).

In some embodiments, the size of the nanoparticle can be controlled by the adjusting the amount (e.g., ratio) of carrier protein to antibody. The size of the nanoparticles, and the size distribution, is also important. The nanoparticles of the invention may behave differently according to their size. At large sizes, an agglomeration may block blood vessels. Therefore, agglomeration of nanoparticles can affect the performance and safety of the composition. On the other hand, larger particles may be more therapeutic under certain conditions (e.g., when not administered intravenously).

In one aspect, the nanoparticle composition comprises at least one additional therapeutic agent. In one embodiment, the at least one additional therapeutic agent is non-covalently bound to the outside surface of the nanoparticle. In one embodiment, the at least one additional therapeutic agent is arranged on the outside surface of the nanoparticle. In one embodiment, the at least one additional therapeutic agent is selected from the group consisting of abiraterone, bendamustine, bortezomib, carboplatin, cabazitaxel, cisplatin, chlorambucil, dasatinib, docetaxel, doxorubicin, epirubicin, erlotinib, etoposide, everolimus, gemcitabine, gefitinib, idarubicin, imatinib, hydroxyurea, imatinib, lapatinib, leuprorelin, melphalan, methotrexate, mitoxantrone, nedaplatin, nilotinib, oxaliplatin, pazopanib, pemetrexed, picoplatin, romidepsin, satraplatin, sorafenib, vemurafenib, sunitinib, teniposide, triplatin, vinblastine, vinorelbine, vincristine, and cyclophosphamide. In one embodiment, the at least one additional therapeutic agent is an anti-cancer antibody.

Methods of Making Nanoparticles

In some aspects, the current invention relates to methods of making nanoparticle compositions as described herein.

In one aspect, the nanoparticles of the nanoparticle composition are formed by contacting the carrier protein or carrier protein-therapeutic agent particle with the antibody at a ratio of about 10:1 to about 10:30 carrier protein particle or carrier protein-therapeutic agent particle to antibody. In one embodiment, the ratio is about 10:2 to about 10:25. In one embodiment, the ratio is about 10:2 to about 1:1. In a preferred embodiment, the ratio is about 10:2 to about 10:6. In an especially preferred embodiment, the ratio is about 10:4. Contemplated ratios include any value, subrange, or range within any of the recited ranges, including endpoints.

In one embodiment, the amount of solution or other liquid medium employed to form the nanoparticles is particularly important. No nanoparticles are formed in an overly dilute solution of the carrier protein (or carrier protein-therapeutic agent) and the antibodies. An overly concentrated solution will result in unstructured aggregates. In some embodiments, the amount of solution (e.g., sterile water, saline, phosphate buffered saline) employed is between about 0.5 mL of solution to about 20 mL of solution. In some embodiments, the amount of carrier protein is between about 1 mg/mL and about 100 mg/mL. In some embodiments, the amount of antibody is between about 1 mg/mL and about 30 mg/mL. For example, in some embodiments, the ratio of carrier protein:antibody:solution is approximately 9 mg of carrier protein (e.g., albumin) to 4 mg of antibody (e.g., BEV) in 1 mL of solution (e.g., saline). An amount of therapeutic agent (e.g., taxol) can also be added to the carrier protein. For example, 1 mg of taxol can be added 9 mg of carrier protein (10 mg carrier protein-therapeutic) and 4 mg of antibody in 1 mL of solution. When using a typical i.v. bag, for example, with the solution of approximately 1 liter one would need to use 1000× the amount of carrier protein/carrier protein-therapeutic agent and antibodies compared to that used in 1 mL. Thus, one cannot form the present nanoparticles in a standard i.v. bag. Furthermore, when the components are added to a standard i.v. bag in the therapeutic amounts of the present invention, the components do not self-assemble to form nanoparticles.

In one embodiment, the carrier protein or carrier protein-therapeutic agent particle is contacted with the antibody in a solution having a pH between about 4 and about 8. In one embodiment, the carrier protein or carrier protein-therapeutic agent particle is contacted with the antibody in a solution having a pH of about 4. In one embodiment, the carrier protein or carrier protein-therapeutic agent particle is contacted with the antibody in a solution having a pH of about 5. In one embodiment, the carrier protein or carrier protein-therapeutic agent particle is contacted with the antibody in a solution having a pH of about 6. In one embodiment, the carrier protein or carrier protein-therapeutic agent particle is contacted with the antibody in a solution having a pH of about 7. In one embodiment, the carrier protein or carrier protein-therapeutic agent particle is contacted with the antibody in a solution having a pH of about 8. In a preferred embodiment, the carrier protein or carrier protein-therapeutic agent particle is contacted with the antibody in a solution having a pH between about 5 and about 7.

In one embodiment, the carrier protein particle or carrier protein-therapeutic agent particle is incubated with the antibody at a temperature of about 5° C. to about 60° C., or any range, subrange, or value within that range including endpoints. In a preferred embodiment, the carrier protein particle or carrier protein-therapeutic agent particle is incubated with the antibody at a temperature of about 23° C. to about 60° C.

Without being bound by theory, it is believed that the stability of the nanoparticles within the nanoparticle composition is, at least in part, dependent upon the temperature and/or pH at which the nanoparticles are formed, as well as the concentration of the components (i.e., carrier protein, antibody, and optionally therapeutic agent) in the solution. In one embodiment, the $K_d$ of the nanoparticles is between about $1 \times 10^{-11}$ M and about $2 \times 10^{-5}$ M. In one embodiment, the $K_d$ of the nanoparticles is between about $1 \times 10^{-11}$ M and about $2 \times 10^{-8}$ M. In one embodiment, the $K_d$ of the nanoparticles is between about $1 \times 10^{-11}$ M and about $7 \times 10^{-9}$ M. In a preferred embodiment, the $K_d$ of the nanoparticles is between about $1 \times 10^{-11}$ M and about $3 \times 10^{-8}$ M. Contemplated values include any value, subrange, or range within any of the recited ranges, including endpoints.

Lyophilization

The lyophilized compositions of this invention are prepared by standard lyophilization techniques with or without the presence of stabilizers, buffers, etc. Surprisingly, these conditions do not alter the relatively fragile structure of the nanoparticles. Moreover, at best, these nanoparticles retain their size distribution upon lyophilization and, more importantly, can be reconstituted for in vivo administration (e.g., intravenous delivery) in substantially the same form and ratios as if freshly made.

Formulations

In one aspect, the nanoparticle composition is formulated for direct injection into a tumor. Direct injection includes injection into or proximal to a tumor site, perfusion into a tumor, and the like. Because the nanoparticle composition is not administered systemically, a nanoparticle composition is formulated for direct injection into a tumor may comprise any average particle size. Without being bound by theory, it is believed that larger particles (e.g., greater than 500 nm, greater than 1 µm, and the like) are more likely to be immobilized within the tumor, thereby providing what is believed to be a better beneficial effect.

In another aspect, provided herein is a composition comprising a compound provided herein, and at least one pharmaceutically acceptable excipient.

In general, the compounds provided herein can be formulated for administration to a patient by any of the accepted modes of administration. Various formulations and drug delivery systems are available in the art. See, e.g., Gennaro, A. R., ed. (1995) *Remington's Pharmaceutical Sciences*, 18$^{th}$ ed., Mack Publishing Co.

In general, compounds provided herein will be administered as pharmaceutical compositions by any one of the following routes: oral, systemic (e.g., transdermal, intranasal or by suppository), or parenteral (e.g., intramuscular, intravenous or subcutaneous) administration.

The compositions are comprised of in general, a compound of the present invention in combination with at least one pharmaceutically acceptable excipient. Acceptable excipients are non-toxic, aid administration, and do not adversely affect the therapeutic benefit of the claimed compounds. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols. Other suitable pharmaceutical excipients and their formulations are described in Remington's Pharmaceutical Sciences, edited by E. W. Martin (Mack Publishing Company, 18th ed., 1990).

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition, Treatment Methods The nanoparticle compositions as described herein are useful in treating cancer cells and/or tumors in a mammal. In a preferred embodiment, the mammal is a human (i.e., a human patient). Preferably, the lyophilized nanoparticle composition is reconstituted (suspended in an aqueous excipient) prior to administration.

In one aspect is provided a method for treating a cancer cell, the method comprising contacting the cell with an effective amount of nanoparticle composition as described herein to treat the cancer cell. Treatment of a cancer cell includes, without limitation, reduction in proliferation, killing the cell, preventing metastasis of the cell, and the like.

In one aspect is provided a method for treating a tumor in a patient in need thereof, the method comprising administering to the patient a therapeutically effective amount of a nanoparticle composition as described herein to treat the tumor. In one embodiment, the size of the tumor is reduced. In one embodiment, the tumor size does not increase progress) for at least a period of time during and/or after treatment.

In one embodiment, the nanoparticle composition is administered intravenously. In one embodiment, the nanoparticle composition is administered directly to the tumor. In one embodiment, the nanoparticle composition is administered by direct injection or perfusion into the tumor.

In one embodiment, the method comprises:
a) administering the nanoparticle composition once a week for three weeks;
b) ceasing administration of the nanoparticle composition for one week; and
c) optionally repeating steps a) and b) as necessary to treat the tumor.

In one embodiment, the therapeutically effective amount of the nanoparticles described herein comprises about 50 mg/m$^2$ to about 200 mg/m$^2$ carrier protein or carrier protein and therapeutic agent. In a preferred embodiment, the therapeutically effective amount comprises about 75 mg/m$^2$ to about 175 mg/m$^2$ carrier protein or carrier protein and therapeutic agent. Contemplated values include any value, subrange, or range within any of the recited ranges, including endpoints.

In one embodiment, the therapeutically effective amount comprises about 20 mg/m$^2$ to about 90 mg/m$^2$ antibody. In a preferred embodiment, the therapeutically effective amount comprises 30 mg/m$^2$ to about 70 mg/m$^2$ antibody. Contemplated values include any value, subrange, or range within any of the recited ranges, including endpoints.

Cancers or tumors that can be treated by the compositions and methods described herein include, but are not limited to: biliary tract cancer; brain cancer, including glioblastomas and medulloblastomas; breast cancer; cervical cancer; choriocarcinoma; colon cancer; endometrial cancer; esophageal cancer, gastric cancer; hematological neoplasms, including acute lymphocytic and myelogenous leukemia; multiple myeloma; AIDS associated leukemias and adult T-cell leukemia lymphoma; intraepithelial neoplasms, including Bowen's disease and Paget's disease; liver cancer (hepato-carcinoma); lung cancer; lymphomas, including Hodgkin's disease and lymphocytic lymphomas; neuroblastomas; oral cancer, including squamous cell carcinoma; ovarian cancer, including those arising from epithelial cells, stromal cells, germ cells and mesenchymal cells; pancreas cancer; prostate cancer; rectal cancer; sarcomas, including leiomyosarcoma, rhabdomyosarcoma, liposarcoma, fibrosarcoma and osteosarcoma; skin cancer, including melanoma, Kaposi's sarcoma, basocellular cancer and squamous cell cancer; testicular cancer, including germinal tumors (seminoma, non-seminoma[teratomas, choriocarcinomas]), stromal tumors and germ cell tumors; thyroid cancer, including thyroid adenocarcinoma and medullar carcinoma; and renal cancer including adenocarcinoma and Wilms tumor. In important embodiments, cancers or tumors include breast cancer, lymphoma, multiple myeloma, and melanoma.

In general, the compounds of this invention will be administered in a therapeutically effective amount by any of the accepted modes of administration for agents that serve similar utilities. The actual amount of the compound of this invention, i.e., the nanoparticles, will depend upon numerous factors such as the severity of the disease to be treated, the age and relative health of the subject, the potency of the compound used, the route and form of administration, and other factors well known to the skilled artisan.

An effective amount of such agents can readily be determined by routine experimentation, as can the most effective and convenient route of administration, and the most appropriate formulation. Various formulations and drug delivery systems are available in the art. See, e.g., Gennaro, A. R., ed. 0995) *Remington's Pharmaceutical Sciences*, 18$^{th}$ ed., Mack Publishing Co.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

EXAMPLES

The present disclosure is illustrated using nanoparticles composed of albumin-bound paclitaxel (i.e., Abraxane®) or cisplatin as core, and bevacizumab (i.e., Avastin®) or Rituximab (i.e., Rituxan®) as antibodies.

One skilled in the art would understand that making and using the nanoparticles of the Examples are for the sole purpose of illustration, and that the present disclosure is not limited by this illustration.

Any abbreviation used herein, has normal scientific meaning. All temperatures are ° C. unless otherwise stated. Herein, the following terms have the following meanings unless otherwise defined:

ABX=Abraxane®/(albumin-bound paclitaxel)
AC=cisplatin-bound ABX
ACN=acetonitrile
ADC=antibody dependent chemotherapy
BEV=bevacizumab
BSA=bovine serum albumin
dH$_2$O=distilled water
DMEM=Dulbecco's Modified Eagle's Medium
nM=nano molar
EdU=5-ethynyl-2'-deoxyuridine
EM=electron microscopy
FCB=flow cytometry buffer
FITC=Fluorescein
kD=kilo-dalton
k$_d$=dissociation constant
kg=kilogram
KV=kilo-volts
L/hr=liter/hour
LC-MS=liquid chromatography-mass spectrometry
M=molar
mCi=millicuries
mg=milligram
ml or mL=milliliter
m$^2$=square meters
mm$^3$=cubic millimeter
μg=microgram
μl=microliter
μm=micrometer/micron
PBS=Phosphate buffered saline
pK=pharmacokinetics
RT=room temperate
rpm=rotations per minute
V=volts
xg=times gravity Example 1: Nanoparticle Preparation Abraxane (ABX) (10 mg) was suspended in bevacizumab (BEV) (4 mg [160 μl] unless otherwise indicated), and 840 μl of 0.9% saline was added to give a final concentration of 10 mg/ml and 2 mg/ml of ABX and BEV, respectively. The mixture was incubated for 30 minutes at room temperature (or at the temperature indicated) to allow particle formation. For Mastersizer experiments to measure particle size of ABX:BEV complexes, 10 mg of ABX was suspended in BEV at concentrations of 0 to 25 mg/ml. Complexes of ABX with rituximab (0-10 mg/ml) or trastuzumab (0-22 mg/ml) were formed under similar conditions.

For use in humans, the ABX:BEV complexes may be prepared by obtaining the dose appropriate number of 4 mL vials of 25 mg/mL, BEV and diluting each vial per the following directions to 4 mg/mL. The dose appropriate number of 100 mg vials of ABX can be prepared by reconstituting to a final concentration containing 10 mg/mL ABX nanoparticles. Using a sterile 3 mL syringe, 1.6 mL (40 mg) of bevacizumab (25 mg/mL) can be withdrawn and slowly injected, over a minimum of 1 minute, onto the inside wall of each of the vials containing 100 mg of ABX. The bevacizumab solution should not be injected directly onto the lyophilized cake as this will result in foaming. Then, using a sterile 12 mL sterile syringe, 8.4 mL 0.9% Sodium Chloride Injection, USP, can be withdrawn and slowly injected, over a minimum of 1 minute, 8.4 mL onto the inside wall of each vial containing ABX 100 mg and BEV 40 mg. Once the addition of BEV 1.6 mL and 0.9% Sodium Chloride Injection, USP 8.4 mL is completed, each vial can be gently swirled and/or inverted slowly for at least 2 minutes until complete dissolution of any cake/powder occurs. Generation of foam should be avoided. At this point, the concentration of each vial should be 100 mg/10 mL ABX and 40 mg/10 mL BEV. The vials containing the ABX and BEV should sit for 60 minutes. The vial(s) should be gently swirled and/or inverted every 10 minutes to continue to mix the complex. After 60 minutes has elapsed, the calculated dosing volume of ABX and BEV should be withdrawn from each vial and slowly added to an empty viaflex bag. An equal volume of 0.9% Sodium Chloride Injection, USP is then added to make the final concentration of ABX 5 mg/mL and BEV 2 nag/mL. The bag should then be gently swirled and/or inverted slowly for 1 minute to mix. The ABX:BEV nanoparticles can be stored for up to 4 hours at room temperature following final diluation.

Example 2: Binding of ABX and BEV in Vitro

Figure 1B:
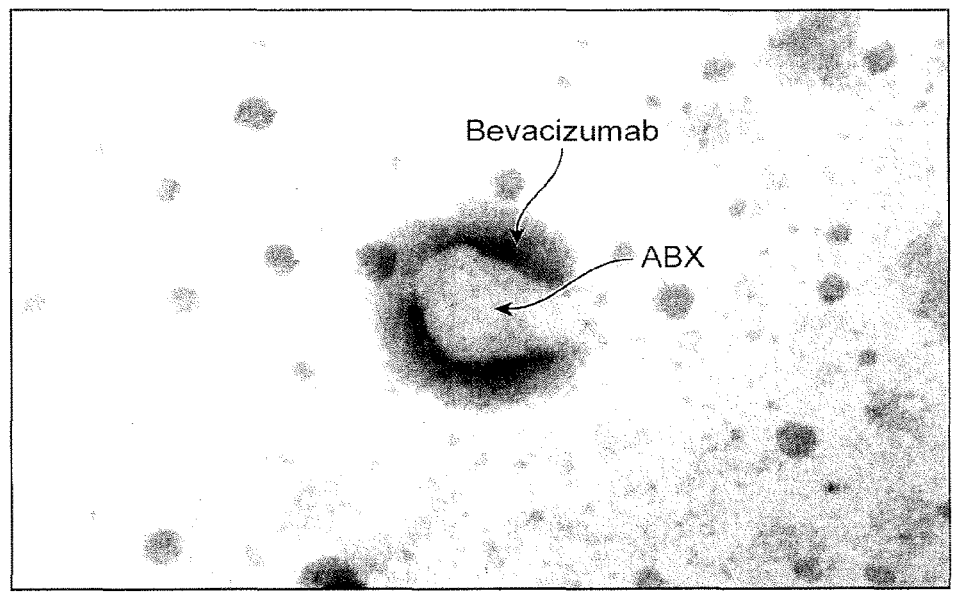
FIG. 1B shows a representative electron micrograph after incubation of AB160 with gold particle-labeled anti-human IgG Fc.

To determine whether ABX and BEV interact, the nanoparticles formed in Example 1 were analyzed by flow cytometry and electron microscopy.
Methods
Flow Cytometry:
AB160 was produced as described in Example 1 above. To determine binding of BEV to ABX, visualization of AB160 was performed on an Accuri C6 flow cytometer (BD Franklin Lakes, N.J.) and data analysis was done using Accuri C6 software. Biotinylated (5 µg) goat anti-mouse IgG (Abcam, Cambridge, Mass.) was labeled with 5 µg of streptavidin PE (Abcam, Cambridge, Mass.). The goat anti-mouse IgG was chosen to label AB160 because the Fab portion of the BEV is mouse derived. ABX and AB160 were incubated with the PE-labeled goat anti-mouse IgG for 30 minutes at room temperature, washed and visualized by flow cytometery.
Electron Microscopy:
Five µl ABX, dissolved in PBS at 6 mg/ml, was added to a 300-mesh parlodian-carbon coated copper grid and allowed to sit for 1 minute. A pointed piece of filter paper was touched to the drop to remove excess liquid, leaving a thin film on the grid. The grids were allowed to dry. To dissolve the buffer crystals left on the dried grid, the sample was washed three times in dH$_2$O. A small drop of 1% phosphotungstic acid (PTA), pH 7.2, was added to the grid. The grid was then again touched by a pointed piece of filter paper to remove excess liquid, leaving a thin film on the grid and allowed to dry. BEV (Genentech) at 25 mg/ml in 0.9% sodium chloride solution was diluted with PBS at 1:10 ratio. Five µl of BEV was loaded on nickel formvar-coated grid and allowed to air dry for 30 minutes to 1 hour. For the AB160, 10 mg/ml ABX, dissolved in PBS, and 4 mg/ml BEV, in 0.9% sodium chloride solution, were mixed at 2.5:1 ratio. The complex was further diluted with PBS at 1:5. Five µl of the complex was loaded on nickel formvar-coated grid and air dried for 30 minutes to 1 hour. Both samples were incubated for 1 hour in goat anti-mouse IgG with 6 nm gold-conjugated particles (Electron Microscopy Sciences), diluted 1:30 with 10% FCB/PBS, washed 6 times with PBS (each 2 minutes), 6 times with dH$_2$O, then stained with the mixture of 2% methylcellulose and 4% UA (9:1) for 5 minutes. Filter paper was used to drain the stain and the grid was air dried for 1 hour, Both samples were incubated overnight in donkey anti-mouse IgG with 6 nm gold-conjugated particles (Jackson ImmunoResearch) diluted 1:25 with 10% FCB/PBS, washed 6 times with PBS (each 2 minutes), 6 times with dH$_2$O water, stained with 1% PTA for 5 minutes, air dried, covered with 2% methylcellulose, and air dried for 1 hour. The micrographs were taken on a JEOL1400 at operating at 80 KV.
Results
ABX (10 mg/ml) was co-incubated with 4 mg/ml BEV in vitro and found that they formed 160 nm nanoparticles (referred to herein as AB160). Because the Fab portion of the IgG1 (BEV) is of mouse origin, particles containing BEV were selectively labeled with purified goat anti-mouse IgG followed by anti-goat PE as a secondary antibody. As a negative control, samples were stained with the anti-goat PE only. Particles were visualized by flow cytometry and demonstrated a bright signal of anti-mouse IgG1 binding to AB160 (41.2% positive) relative to ABX (6.7% positive) alone (FIG. 1A). To validate binding of BEV to ABX, the BEV were labeled with gold-labeled mouse anti-human IgG and the particles were visualized with electron microscopy (FIG. 1B). Surprisingly, the EM pictures suggest a monolayer of BEV surrounding ABX nanoparticles.

Figure 1C:
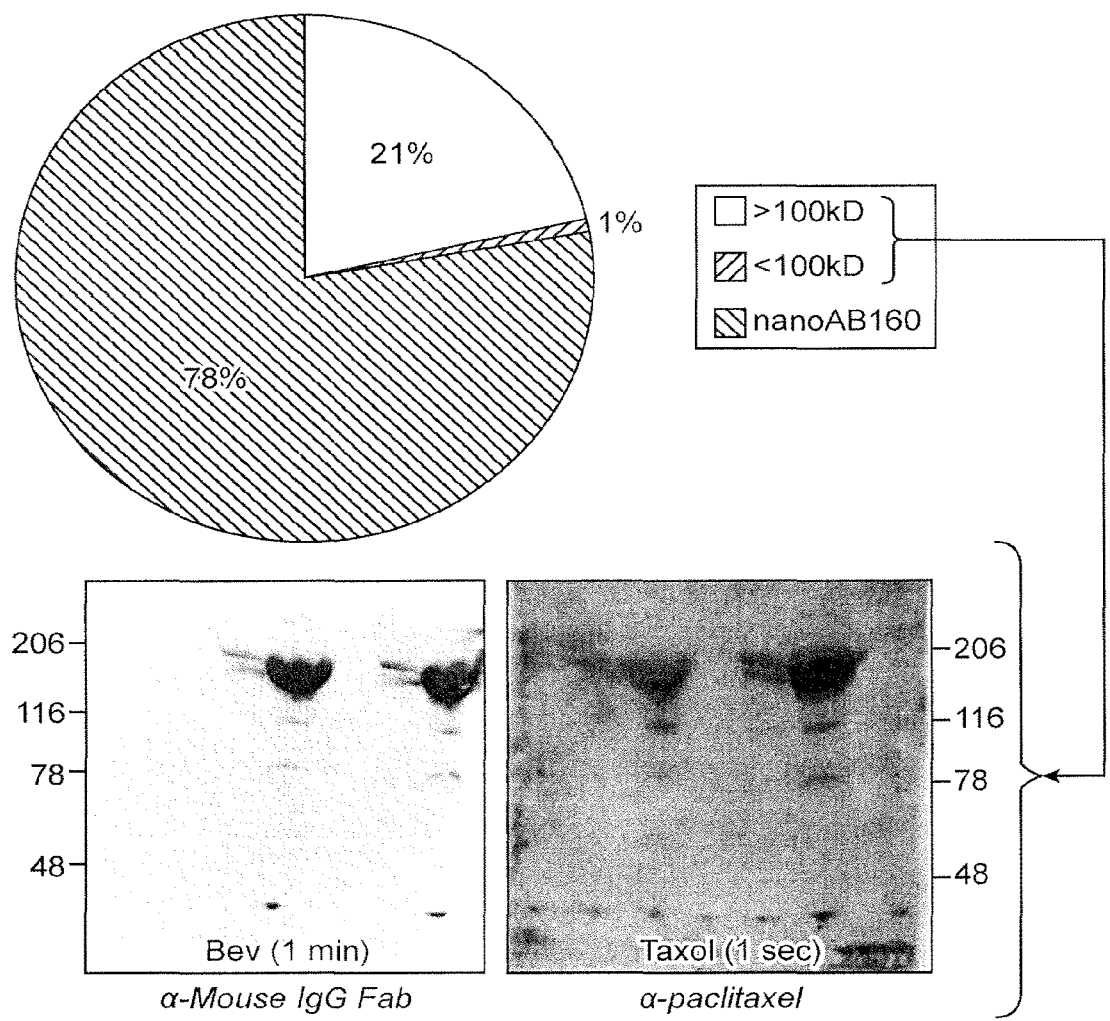
FIG. 1C shows a pie chart (top) indicating the percentages of total paclitaxel in AB160 fractions (particulate, proteins greater than 100 kD and proteins less than 100 kD); and a Western blot with antibodies against mouse IgG Fab (BEV) and paclitaxel to verify co-localization (bottom).

To determine what protein (albumin or BEV) the paclitaxel remains bound to when the complex breaks down, AB160 were made and collected fractions: the particulate (nanoAB160), proteins greater than 100 kD and proteins less than 100 kD. Paclitaxel was measured in each fraction by liquid chromatography-mass spectrometry (LC-MS). Roughly 75% of the paclitaxel remained within the particulate, and the majority of the remaining paclitaxel was associated with the fraction containing proteins 100 kD or greater (FIG. 1C, top), suggesting that when the particulate dissociates the paclitaxel is bound to BEV alone or a BEV and albumin heterodimer. This indicates that the dissociated complexes contain the chemotherapy drug with the antibody, which would still traffic to the high-VEGF tumor microenvironment. These findings were confirmed by Western blot analysis of the supernatants from AB160, which showed that BEV and paclitaxel co-localize at approximately 200 kD, a size consistent with a paclitaxel-BEV-albumin protein complex (FIG. 1C, bottom).

Example 3: Function of AB160 in Vitro

Confirmation that the two key elements in the complexes, the antibody and the paclitaxel, retained their function when present in the complexes was demonstrated.
Methods
In Vitro Toxicity:
The A375 human melanoma cell line (ATCC Manassa, Va.) and Daudi B-cell lymphoma line (ATCC Manassa, Va.) were cultured in DMEM with 1% PSG and 10% FBS. Cells were harvested and plated at 0.75×10⁶ cells per well in 24 well plates. Cells were exposed to ABX or AB160 at paclitaxel concentrations from 0 to 200 μg/ml overnight at 37° C. and 5% $CO_2$. To measure proliferation, the Click-iT EdU (Molecular Probes, Eugene, Oreg.) kit was utilized. Briefly, 10 mM EdU was added to the wells and incubated overnight with the cells and ABX or AB160. The cells were permeabilized with 1% saponin and intercalated EdU was labeled with a FITC-conjugated antibody. The proliferation index was determined by dividing the FITC positive cells from each treatment by the maximum proliferation of untreated EdU labeled cells.

VEGF ELISA:

To determine whether BEV can still hind its ligand, VEGF, when bound to ABX, a standard VEGF ELISA (R and D Systems, Minneapolis, Minn.) was employed. AB160 was prepared as described and 2000 pg/ml VEGF was added to the AB160 complex or ABX alone. The VEGF was incubated with the nanoparticles for 2 hours at room temperature. The suspension was spun at 6000 rpm for 15 minutes, supernatants were collected and free VEGF was measured by ELISA. Briefly, ELISA plates were coated with capture antibody overnight at 4° C. Plates were washed, blocked and standards and samples were added. After washing, detection antibody was added and plates were developed with substrate (R and D Systems, Minneapolis, Minn.). Absorbance was measured at 450 nm using a Versamax ELISA plate reader (Molecular Devices, Sunnyvale, Calif.). The concentration of unbound VEGF was determined with a standard curve from 0 to 2000 pg/ml.

Results

Figure 1D:
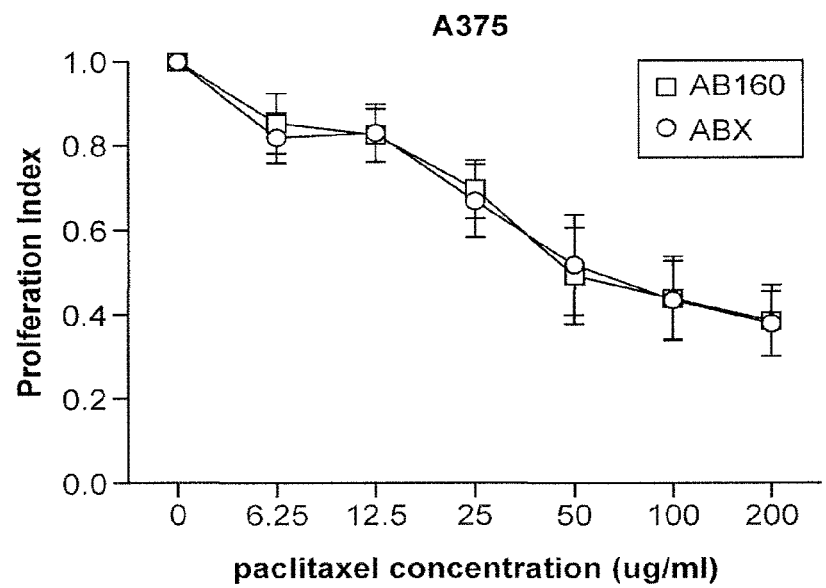
FIG. 1D represents the activity of paclitaxel in an in vitro toxicity assay with A375 human melanoma cells, compared to ABX alone. The results are represented by the average (+/−SEM) proliferation index, which is the percentage of total proliferation of untreated cells. This data represents 3 experiments and differences were not significant.

AB160 has similar toxicity relative to ABX alone in an in vitro toxicity assay with the human melanoma cell line, A375, suggesting that the paclitaxel functions equally in either formulation (FIG. 1D).

Figure 1E:
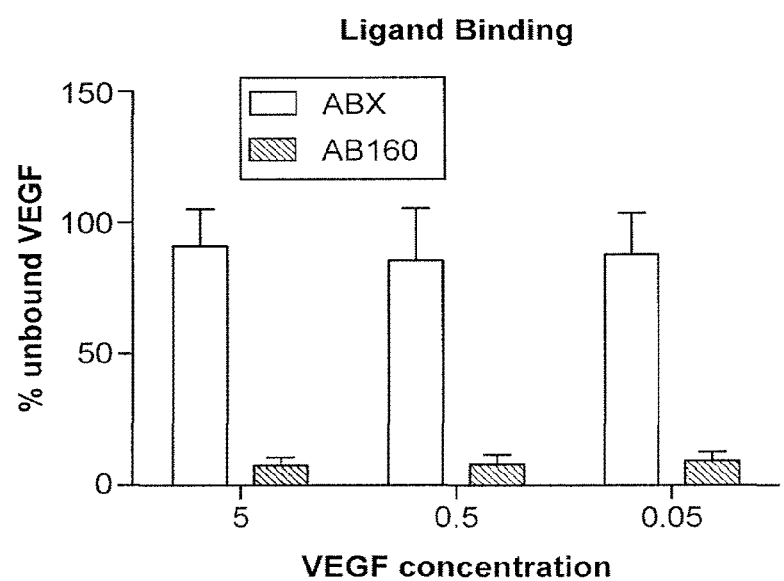
FIG. 1E represents results from a VEGF ELISA of supernatant after co-incubation of VEGF with ABX and AB160 to determine binding of the ligand, VEGF, by the antibody. The results are shown as the average percentage +/−SEM of VEGF that was unbound by the 2 complexes. The data represents 3 experiments **$P<0.005$.

To test the binding of VEGF to BEV in the AB160 complex, AB160 or ABX was co-incubated with VEGF, the particulate removed, and the supernatant tested for VEGF content. The lack of VEGF in the supernatant measured from AB160 (<10% VEGF unbound) indicated that the VEGF was bound by the BEV in the AB160 complex, while it remained free when incubated with the ABX (>80% VEGF unbound) alone (FIG. 1E).

Importantly, these assays demonstrated that the paclitaxel in AB160 retains its toxic to tumor cells and the bound BEV maintains the ability to bind its ligand, VEGF.

Example 4: Particle Size and Protein Affinity

To understand the characteristics of the nanoparticles formed when binding BEV to ABX, the size of the ABX: BEV complexes was determined relative to ABX.

Methods

Mastersizer and Nanosight:

The particle size of ABX and antibody-ABX drug complexes were measured by dynamic light scattering on a Mastersizer 2000 (Malvern Instruments, Westborough, Mass.). To measure particle size, 2 ml (5 mg/ml) of Abraxane or complex was added to the sample chamber. Data were analyzed with Malvern software and particle size distributions were displayed by volume. The particle sizes and stability were later validated using the Nanosight System (Malvern Instruments, Westborough, Mass.). The ABX or complex particles were diluted to the appropriate range to accurately measure particle sizes. Data was displayed by particle size distribution; however, the nanoparticle tracking analysis uses Brownian motion to determine particle size.

Binding Assay:

Biotinylated BEV, rituximab or trastuzumab at 100 μg/ml was bound to the streptavidin probe (ForteBio Corp. MenloPark, Calif.). The binding of ABX was measured by light absorbance on the BLItz system (ForteBio Corp. MenloPark, Calif.) at 1000, 500 and 100 mg/ml. The association and dissociation constants were calculated using the BLItz software.

Bio-Layer Interferometry (BLItz) technology was utilized to assess the binding affinity of BEV to ABX. Biotinylated BEV was bound to the streptavidin probe and exposed to ABX (1000, 500, and 100 μg/ml). The dissociation constant (Kd) of BEV and ABX is $2.2 \times 10^{-8}$ M at room temperature and pH 7, consistent with a strong non-covalent interaction. The binding affinity of BEV and ABX is within the range of dissociation constants observed between albumin and natural or engineered albumin-binding domains of some bacterial proteins. Nilvebrant, J. et al. (2013) *Comput Struct Biotechnol J* 6:e201303009.

Results

Figure 2A:
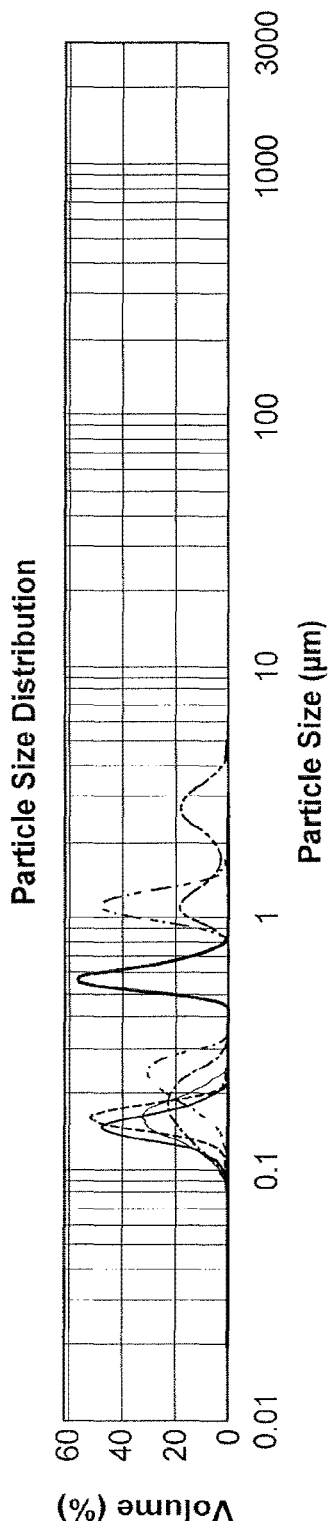
FIG. 2A shows the size of the complexes (determined by light scattering technology) formed by adding BEV (bevacizumab) to ABX under conditions where nanoparticles and higher are formed. Increasing concentrations of BEV (0-25 mg) were added to 10 mg of ABX and the size of the complexes formed was determined. The average size of the complexes (146 nm to 2,166 nm) increased as the concentration of BEV was increased. The data is displayed as volume of sample/size and graphs show the size distribution of the particles. This data is representative of 5 separate drug preparations. As a comparison, ABX, by itself, has an average particle size of about 130 nm.

ABX:BEV nanoparticles were consistently larger (approximately 160 nm) than the 130 nm ABX alone (FIG. 2a). The size of the nanoparticle created directly correlated to the concentration of BEV used, with median sizes ranging from 0.157 to 2.166 μm. (FIG. 2A). With the goal of these studies being a Phase I clinical trial, the smallest ABX:BEV particle (AB160) were focused on because it is the most similar to the 130 nm ABX. The size of the AB160 particle was consistent with ABX plus a monolayer of BEV surrounding it and with the EM image of the particle (see FIG. 1B).

To determine whether intravenous administration conditions affect nanoparticle size distributions, the particle size distributions of AB160 (or ABX) incubated in saline for up to 24 hours at room temperature were evaluated. AB160 size distribution does not significantly change for up to 24 hours (FIGS. 9A and 9B). However, by 4 hours at room temperature, there is some evidence of AB160 breakdown by ELISA (FIG. 9C).

Figure 10:
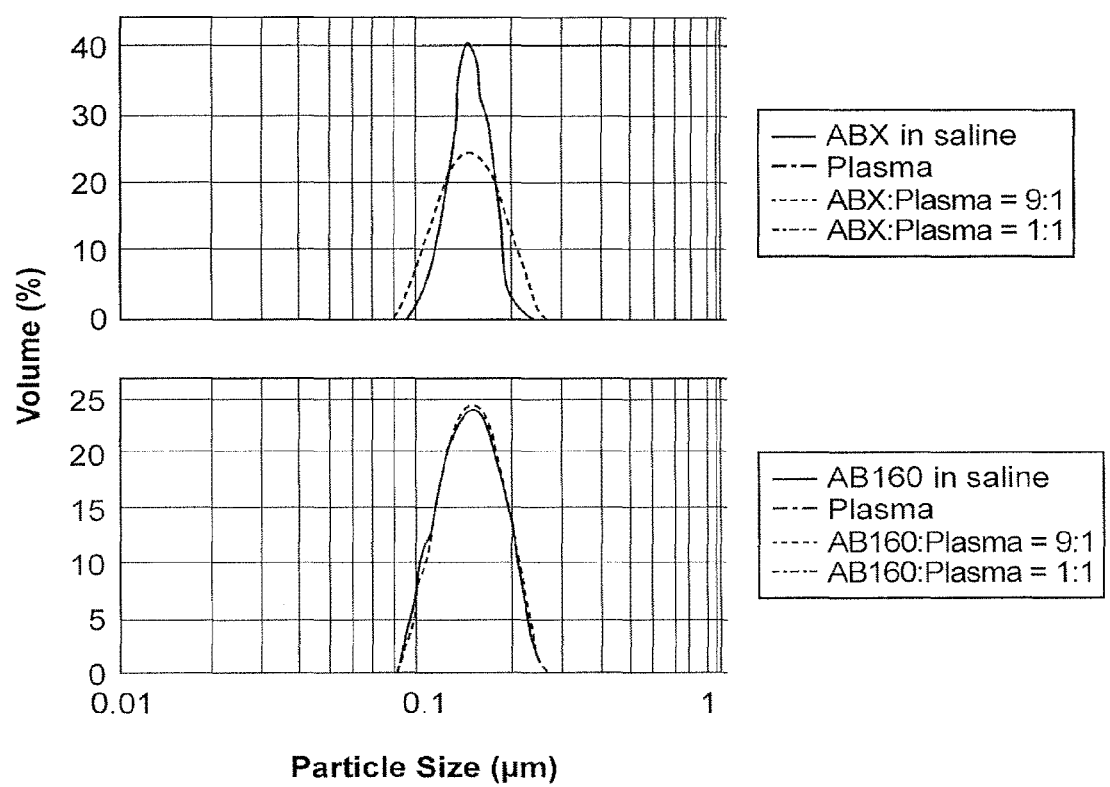
FIG. 10 shows in vitro incubation for 30 seconds of ABX (top panel) or AB160 (bottom panel) in saline or heparinized human plasma at relative volume ratios of 9:1 or 1:1.

To determine the stability of AB160 in plasma, ABX or AB160 was incubated in saline or heparinized human plasma at relative volume ratios of 9:1 or 1:1. Notably, no particles (0.01 to 1 μm) were detected when either ABX (FIG. 10, top panel) or AB160 (FIG. 10, bottom panel) is incubated in plasma at equal volumes (1:1).

Western blot (data not shown) indicated that, in saline or heparinized human plasma, the AB160 dissociated into smaller protein conjugates that still contain the tumor-targeting antibody, albumin and the cytotoxic agent, paclitaxel. These protein conjugates retain their ability to target the tumor and, once at the tumor site, can quickly dissolve and release the cytotoxic payload to effectively initiate tumor regression without internalization of the entire nanoparticle by tumor cells.

Next, the ABX was suspended in BEV and the mixture diluted with saline at pH 3, 5, 7, or 9 prior to incubation at various temperatures (RT, 37° C. and 58° C.) to allow particle formation in order to test whether binding affinity was pH- and/or temperature-dependent. The binding affinity of ABX and BEV is both pH- and temperature-dependent, with the highest binding affinity observed when the particles are formed at pH 5 and 58° C. (FIG. 2B).

To determine if the higher affinity binding of BEV and ABX at 58° C. and pH 5 translated into stability of the complex, various preparations were compared by nanoparticle tracking analysis (Nanosight). The stability of AB160 prepared at 58° C. and pH 5 (AB1600558), room temperature and pH 7 (AB16007), or 58° C. and pH 7 (AB1600758)

was compared to ABX exposed to the same conditions (ABX0558, ABX07, and ABX0758, respectively) after incubation in human AR serum for 0, 15, 30, or 60 minutes.

Figure 2C:
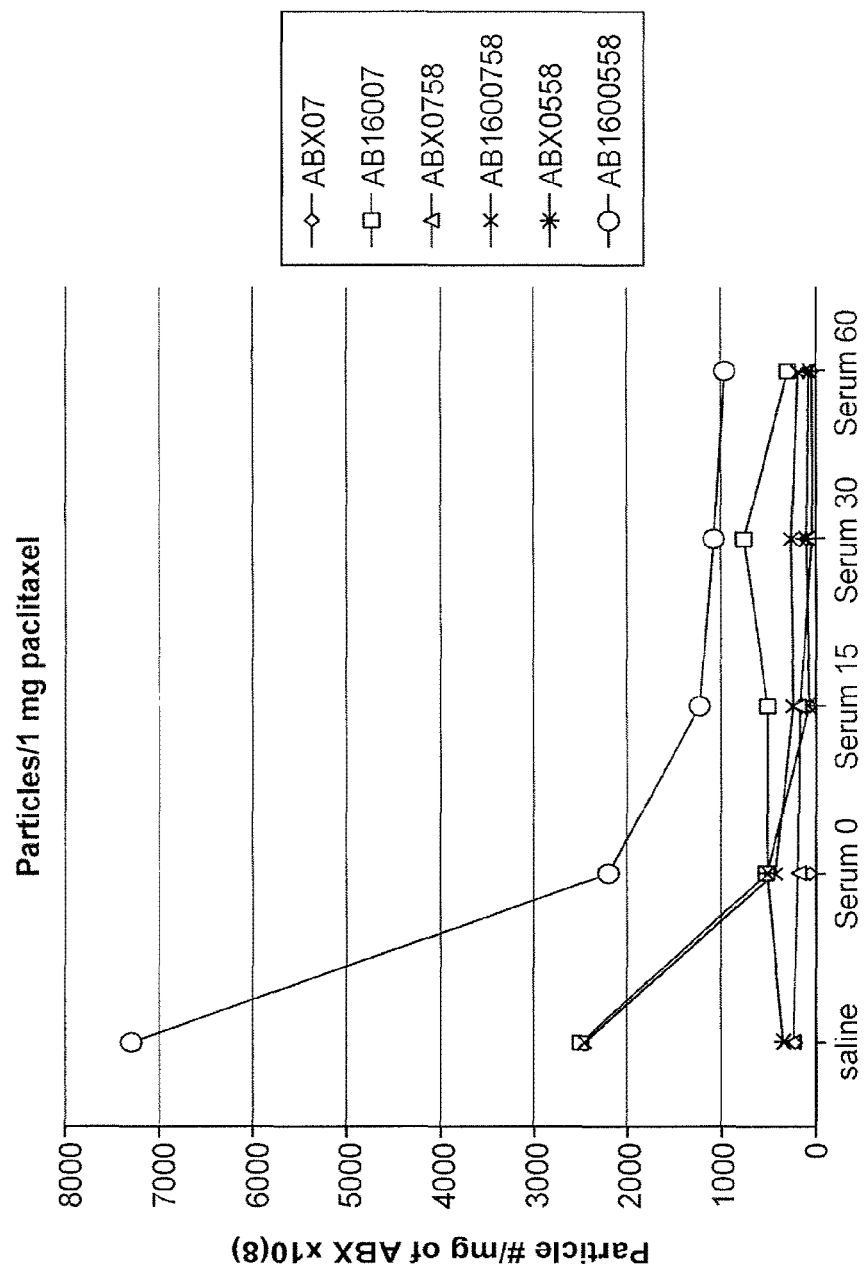
FIG. 2C shows the stability of the nanoparticle complexes from FIG. 2B in serum as determined by a nanoparticle tracking analysis (NTA) on Nanosight 300 (NS300). The data are displayed as the number of particles/mg of ABX and compares AB160 prepared at RT and pH 7 (AB16007; particle size, pH), 58° C. and pH 7 (AB1600758; particle size, pH, temperature) and 58° C. and pH 5 (AB1600558; particle size, pH, temperature), relative to ABX alone under each condition. Once particles were prepared, they were added to human AB serum for 15, 30, and 60 minutes to determine stability in serum over time.

The particles made under higher affinity conditions (pH 7 and 58° C.) were also more stable, as indicated by the number of particles present per mg ABX after exposure to human AB serum. The AB160 particles exhibited increased stability in human serum that correlated with their binding affinities. In particular, AB16007 and AB1600558 were more stable in both saline and human serum than ABX alone, as determined by size and number of particles measured per mg ABX (FIG. 2C and Table 3). This shows that the stability of AB160 particles can be manipulated by changing the conditions under which the AB160 particles are formed.

TABLE 3

Stability of AB160 and ABX in human AB serum

| | Saline | Human AB Serum | | | |
|---|---|---|---|---|---|
| | | 0 min | 15 min | 30 min | 60 min |
| ABX07 | 221.5 | 54.4 | 85.2 | 84 | 32.1 |
| AB16007 | 2500 | 516 | 508 | 756 | 296 |
| ABX0758 | 236 | 182.4 | 155.4 | 54 | 66 |
| AB1600758 | 2460 | 436 | 236 | 260 | 176 |
| ABX0558 | 348 | 510 | 86.8 | 90 | 64 |
| AB1600558 | 7296 | 2200 | 1224 | 1080 | 960 |

Particles per mg ABX × $10^8$

These data demonstrated that BEV binds to ABX with affinity in the picomolar range, indicating a strong non-covalent bond, and demonstrated a particle size distribution consistent with ABX surrounded by a monolayer of antibody molecules; the size of the particles created is dependent on the antibody concentration.

Example 5: Efficacy of A13160 in Mice

Figure 3A:
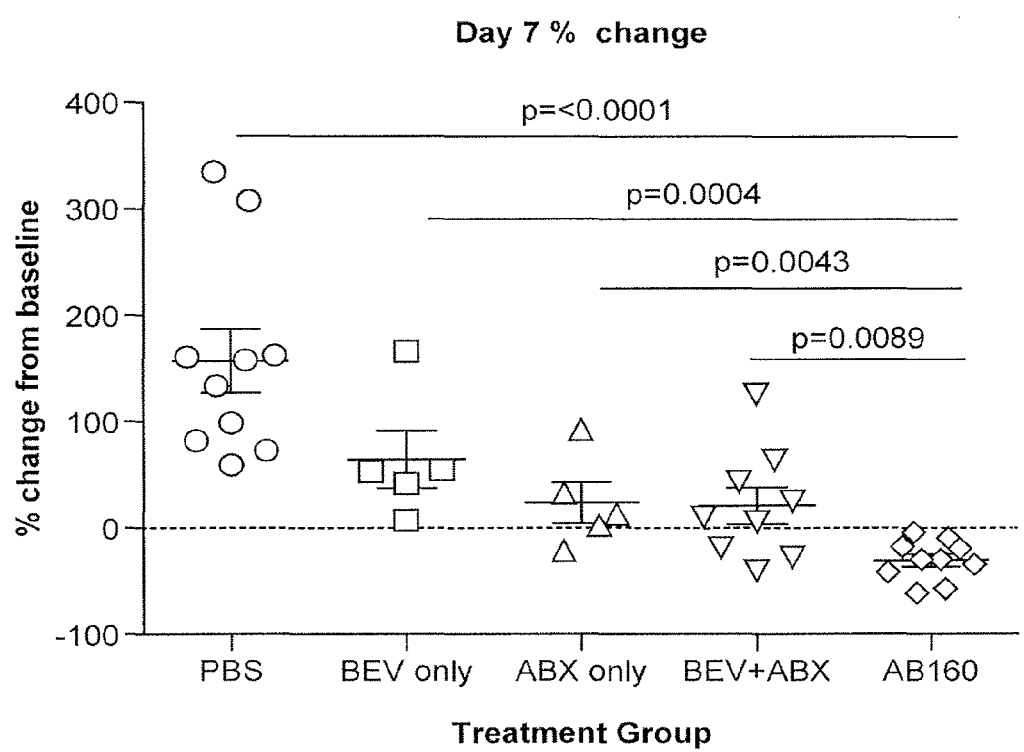
FIG. 3A shows in vivo testing of AB nanoparticles in athymic nude mice injected with 1×10⁶ A375 human melanoma cells in the right flank and treated with PBS, 12 mg/kg BEV, 30 mg/kg ABX, 12 mg/kg BEV+30 mg/kg ABX, or AB160 (having about 12 mg/kg BEV and about 30 mg/kg ABX) at tumor size between approximately 600 mm³ to 900 mm³. Data is represented at day 7-post treatment as the percent change in tumor size from baseline (the size of the tumor on the day of treatment). Student's t-test was used to determine significance. The p-values for the AB particles were all significantly different than PBS, the individual drugs alone and the 2 drugs given sequentially.
Figure 3B:
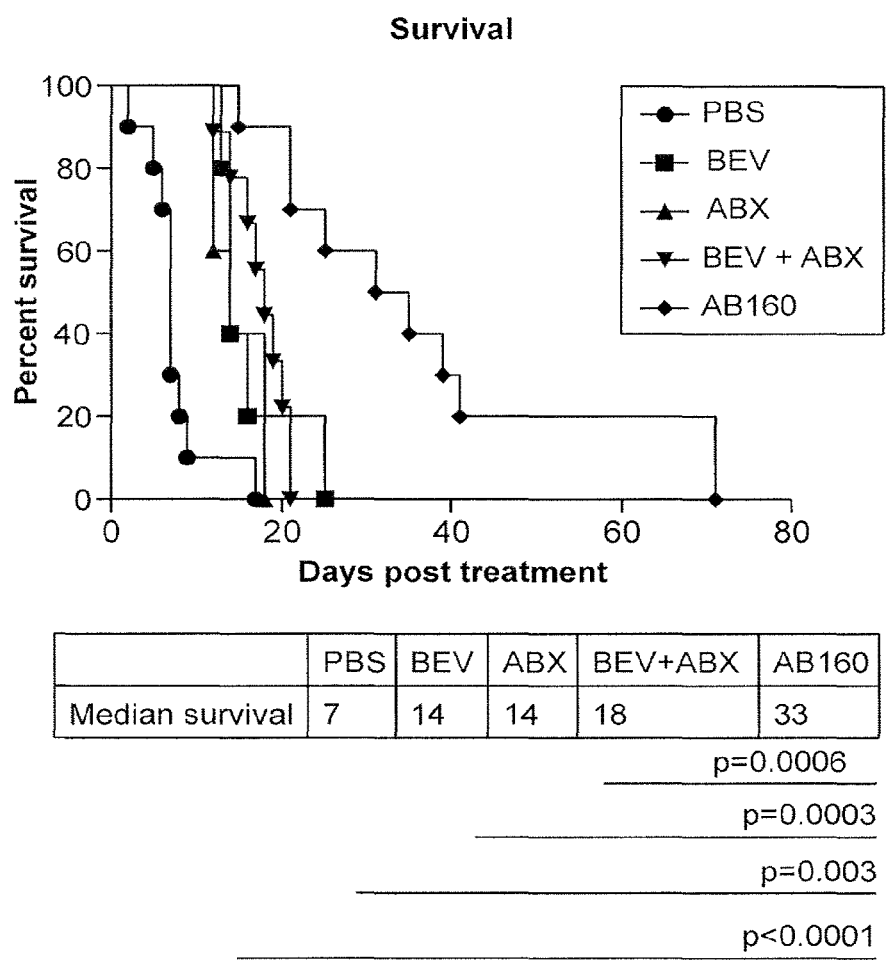
FIG. 3B shows Kaplan-Meier curves generated for median survival of the mice analyzed in FIG. 3A. Significance was determined using the Mantle-Cox test comparing survival curves.

A xenograft model of A375 human melanoma cells implanted into athymic nude mice was employed to test AB160 efficacy in vivo.
Methods
In vivo experiments were performed at least 2 times. The number of mice required for those experiments was determined by power analysis. Mouse tumors were measured 2-3 times/week and mice were sacrificed when the tumor was 10% by weight. Mice that had complete tumor responses were monitored for 60-80 days post-treatment. The end point of the mouse studies was median survival. Kaplan-Meier curves were generated and Mantle-Cox test was performed to determine significance of median survival between treatment groups. The in vitro results presented are representative of at least 5 repeated experiments. Statistical analyses of in vitro and in vivo percent change from baseline experiments were done using the Student's t-test.
Mouse Model:
To test tumor efficacy, $1 \times 10^6$ A375 human melanoma cells were implanted into the right flank of athymic nude mice (Harlan Sprague Dawley, Indianapolis, Ind.). When the tumors had reached a size of about 700 mm³, the mice were randomized and treated with PBS, ABX (30 mg/kg), BEV (12 mg/kg), BEV followed by ABX, or AB160 at the above concentrations. For the mouse experiments testing bigger AB particles, the highest dose of BEV (45 mg/kg) necessary to create the larger particles was used in the BEV-only treatment group. Tumor size was monitored 3 times/week and tumor volume was calculated with the following equation: (length*width²)/2. Mice were sacrificed when the tumor size equaled 10% of the mouse body weight or about 2500 mm³. The day 7 percent change from baseline was calculated as follows: [(tumor size on treatment day-tumor size on day 7)/tumor size on treatment day]*100. The in vivo testing of the AR160 was similar except $5 \times 10^6$ Daudi cells were injected into the right flank of athymic nude mice.
Results
AB160 was tested relative to PBS, the single drugs alone, and the drugs administered sequentially. Mice treated with AB160 had significantly reduced tumor size compared to all other treatment groups (p=0.0001 to 0.0089) at day 7 post-treatment, relative to baseline (FIG. 3A). Tumors in all of the mice treated with AB160 had regressed at day 7, and this tumor response translated into significantly increased median survival of the AB160 group relative to all other groups (FIG. 3B), with a survival of 7, 14, 14, 18 and 33 days for the PBS (p<0.0001), BEV (p=0.003), ABX (p=0.0003), BEV+ABX (p=0.0006) and AB160 groups, respectively.

Figure 3C:
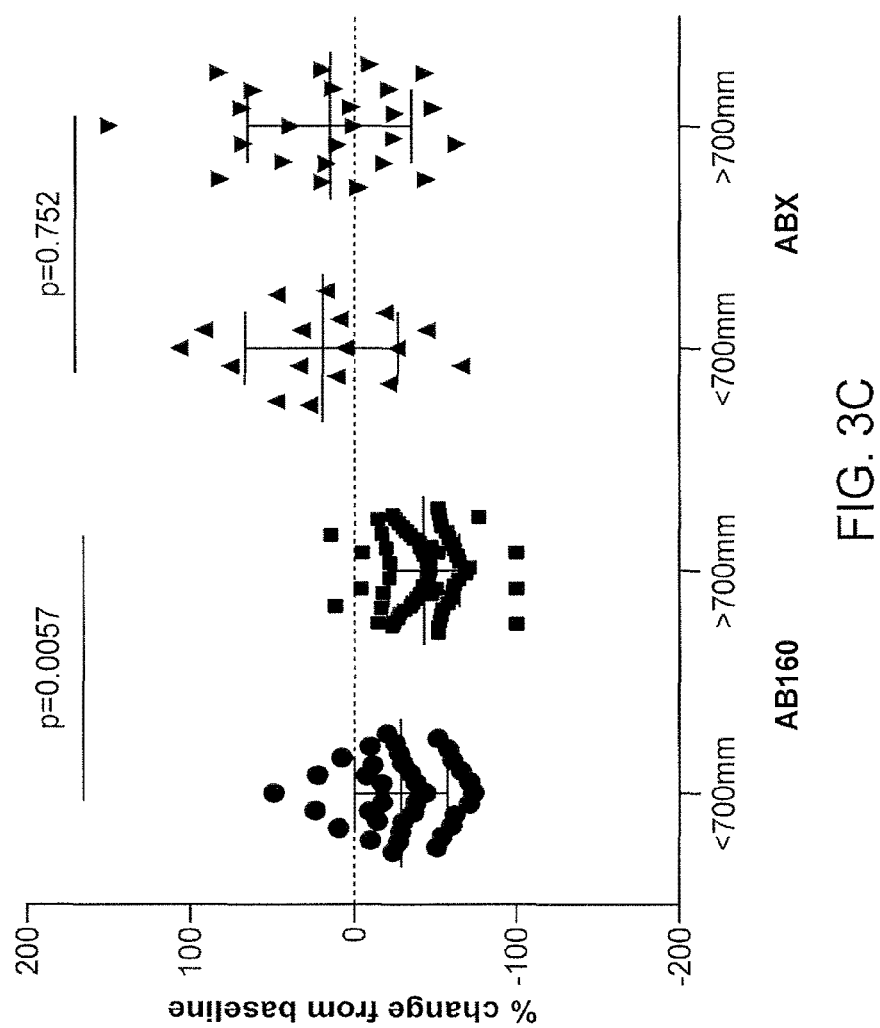
FIG. 3C shows the percent change from baseline for mice treated when tumors were less than or greater than 700 mm³, to ascertain whether the size of the tumor affected tumor response for the ABX only and AB160 groups. The Student's t-test was used to determine significance; the ABX only groups showed no significant difference (p=0.752) based on tumor size, while the AB160 groups were significantly different (p=0.0057).

It is likely that larger tumors have a higher local VEGF concentration. When data were analyzed based on the size of the tumor on day of treatment (<700 mm³ and >700 mm³), the larger tumors were shown to have a greater response to AB160, suggesting that higher tumor VEGF concentration attracts more BEV-targeted ABX to the tumor. The difference in the percent change from baseline was significant for the AB160 groups (p=0.0057). This observation was not seen in the ABX only (p=0.752) group, where the ABX has no targeting capability (FIG. 3C).

Figure 3D:
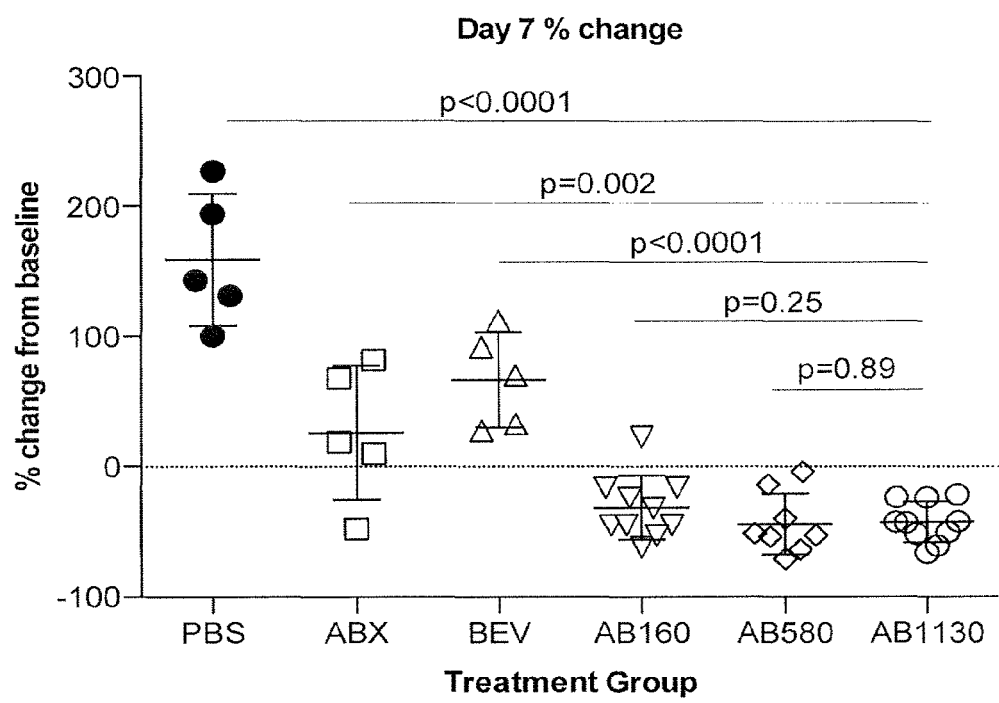
FIG. 3D shows in vivo testing of AB nanoparticles in athymic nude mice injected with 1×10⁶ A375 human melanoma cells in the right flank and treated with PBS, 30 mg/kg ABX, or 45 mg/kg BEV and AB160, AB580 (nanoparticle of albumin-bound paclitaxel to bevacizumab having an average particle size of 580 nm) or AB1130 (nanoparticle of albumin-bound paclitaxel to bevacizumab having an average particle size of 1130 nm) at tumor size between approximately 600 mm³ to 900 mm³. Data is represented at day 7-post treatment as the percent change in tumor size from baseline (the size of the tumor on the day of treatment). Student's t-test was used to determine significance. The p-values for the AB particles were all significantly different than PBS, the individual drugs alone and the 2 drugs given sequentially. The difference among the AB particles of different sizes was not significant.
Figure 3E:
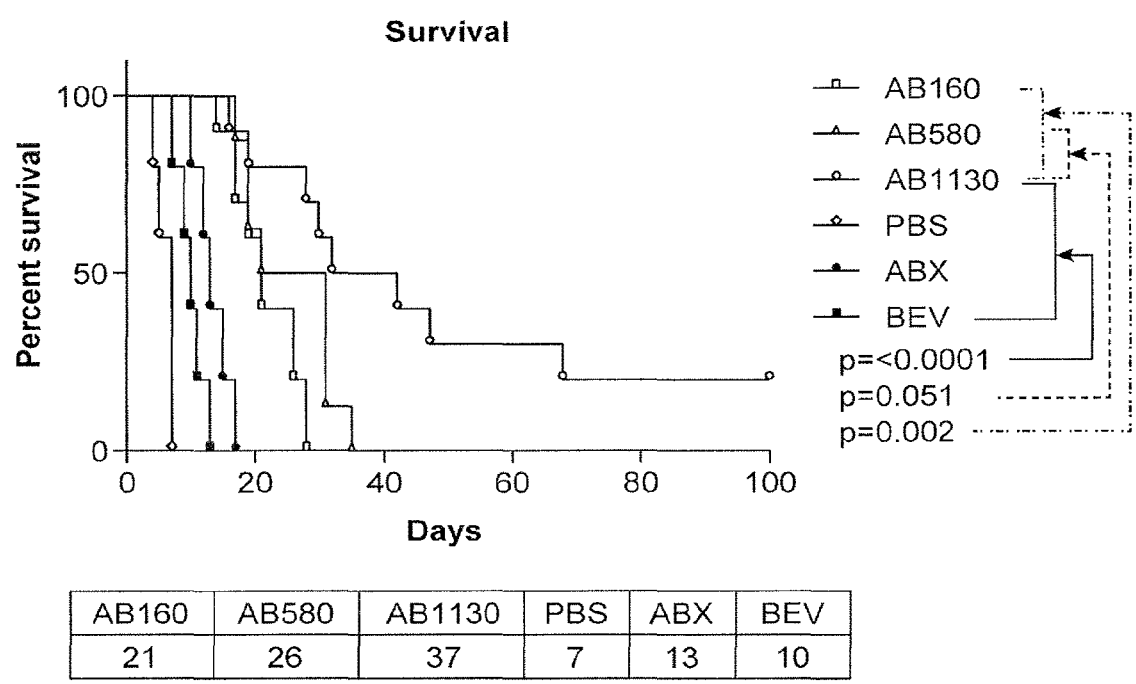
FIG. 3E shows Kaplan-Meier curves generated for median survival of the mice analyzed in FIG. 3D. Significance was determined using the Mantle-Cox test comparing survival curves.

Particles of increasing size were prepared using increasing BEV:ABX ratios as shown in FIG. 2A. Tumor regression and median survival positively correlated with increasing particle size, indicating that biodistribution of larger particles may be altered relative to the smaller ones (FIGS. 3D and 3E). Full toxicity studies were performed on the mice and no toxicities were noted.

Example 6: Paclitaxel Pharmakokinetics in Mice

To compare the pharmacokinetics (pk) of AB160 and ABX, plasma paclitaxel concentrations were measured in mice administered AB160 or ABX at 0, 4, 8, 12 and 24 hours.
Methods
Paclitaxel Pharmacokinetics:
The liquid chromatographic separation of paclitaxel and d5 paclitaxel were accomplished using an Agilent Poroshell 120 EC-C18 precolumn (2.1×5 mm, 2.7 µm, Chrom Tech, Apple Valley, Minn.) attached to an Agilent Poroshell 120 EC-C18 analytical column (2.1×100 mm, 2.7 µm Chrom Tech, Apple Valley, Minn.) at 40° C., eluted with a gradient mobile phase composed of water with 0.1% formic acid (A) and ACN with 0.1% formic acid (B) with a constant flow rate of 0.5 ml/minute. The elution was initiated at 60% A and 40% B for 0.5 minutes, then B was linearly increased from 40-85% for 4.5 minutes, held at 85% B for 0.2 minutes, and returned to initial conditions for 1.3 minutes. Autosampler temperature was 10° C. and sample injection volume was 2 µl. Detection of paclitaxel and the internal standard d5-paclitaxel were accomplished using the mass spectrometer in positive ESI mode with capillary voltage 1.75 kV, source temp 150° C., desolvation temp 500° C., cone gas flow 150 L/hr, desolvation gas flow 1000 L/hr, using multiple reaction monitoring (MRM) scan mode with a dwell time of 0.075 seconds. The cone voltages and collision energies were determined by MassLynx-Intellistart, v4.1, software and varied between 6-16 V and 12-60 eV, respectively. The MRM precursor and product ions were monitored at m/z 854.3>105.2 for paclitaxel and 859.3>291.2 for d5 paclitaxel. The primary stock solutions of paclitaxel (1 mg/ml in EtOH) and d5 paclitaxel (1 mg/ml in EtOH) were prepared in 4 ml amber silanized glass vials and stored at −20° C. Working standards were prepared by dilution of the stock solution with ACN in 2 ml amber silanized glass vials and stored at −20° C. Plasma samples were extracted as follows, 100 µl plasma sample was added to a 1.7 ml microcentrifuge tube containing d5 paclitaxel (116.4 nM or 100 ng/ml) and 300 µl ACN, vortexed, incubated at room temperature for 10 minutes to precipitate proteins, and centrifuged (14,000 rpm) for 3 minutes. The supernatant was filtered on an Agilent Captiva ND$^{lipids}$ plate (Chrom Tech, Apple Valley, Minn.), collected in a deep 96-well plate, and dried using nitrogen gas. The samples were reconstituted using 100 µl ACN and shaken on a plate shaker (high speed) for 5 minutes. Plasma standard curves were prepared daily containing paclitaxel (0.59-5855 nM or 0.5-5000 ng/ml) and d5 paclitaxel (116.4 nM) for paclitaxel quantitation. Mouse tumors were thawed on ice, weighed, and diluted 2 parts (weight to volume) in 1×PBS. Tumors were then homogenized using a PRO200 tissue homogenizer using the saw tooth probe (5 mm×75 mm). Tumor homogenate was than processed the same as the human plasma samples.

Mouse Imaging:

Avastin and IgG control solutions were prepared and I-125 labeled per protocol (Imanis Life Sciences). Briefly, Tris Buffer (0.125 M Tris-HCl, pH 6.8, 0.15 M NaCl) and 5 mCi Na$^{125}$I were added directly to iodination tubes (ThermoFischer Scientific, Waltham, Mass.). The iodide was allowed to activate and was swirled at room temperature. Activated iodide was mixed with the protein solution. 50 µl of Scavenging Buffer (10 mg tyrosine/mL in PBS, pH 7.4) was added and incubated for five minutes. After addition of Tris/BSA buffer and mixing, samples were applied in 10K MWCO dialysis cassettes against pre-cooled PBS for 30 minutes, 1 hour, 2 hours, and overnight at 4° C. Radioactivity was determined by Gamma counter, then disintegrations per minute (DPM) and specific activity were calculated. Mice were injected in their tail vein with Avastin I-125, Abraxane-Avastin I-125, Abraxane-human IgG I-125, or Abraxane only. Animals were imaged at 3, 10, 24 and 72 hours post-administration via SPECT-CT imaging using the U-SPECT-II/CT scanner (MILabs, Utrecht, The Netherlands). SPECT reconstruction was performed using a POSEM (pixelated ordered subsets by expectation maximization) algorithm, CT data were reconstructed during the Feldkamp algorithm. Co-registered images were further rendered and visualized using PMOD software (PMOD Technologies, Zurich, Switzerland). Animals were sacrificed and dissected at 72 hours post-injection. Selected tissues and organs of interest were measured using radioisotope dose calibrator (Capintec CRC-127R, Capintec Inc.).

Results

Figure 4A:
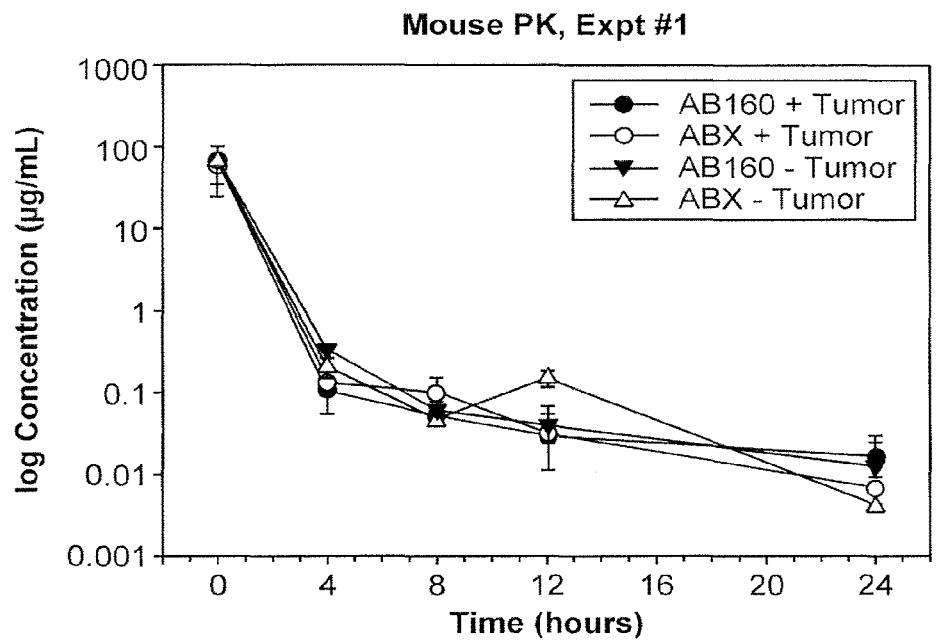
FIG. 4A demonstrates blood paclitaxel concentration displayed in line graph with y-axis in log scale, based on blood and tumor samples taken from non-tumor and tumor bearing mice at 0-24 hours after IV injection with 30 mg/kg of paclitaxel in the context of ABX or AB160 and measured by LC-MS. Mice were IV injected at time 0, with blood samples taken and the mice sacrificed at time points of 0, 4, 8, 12, and 24 hours. There were at least 3 mice per time point. Student's t-test was utilized to determine if any differences in concentrations between ABX and AB160 were significant.
Figure 4B:
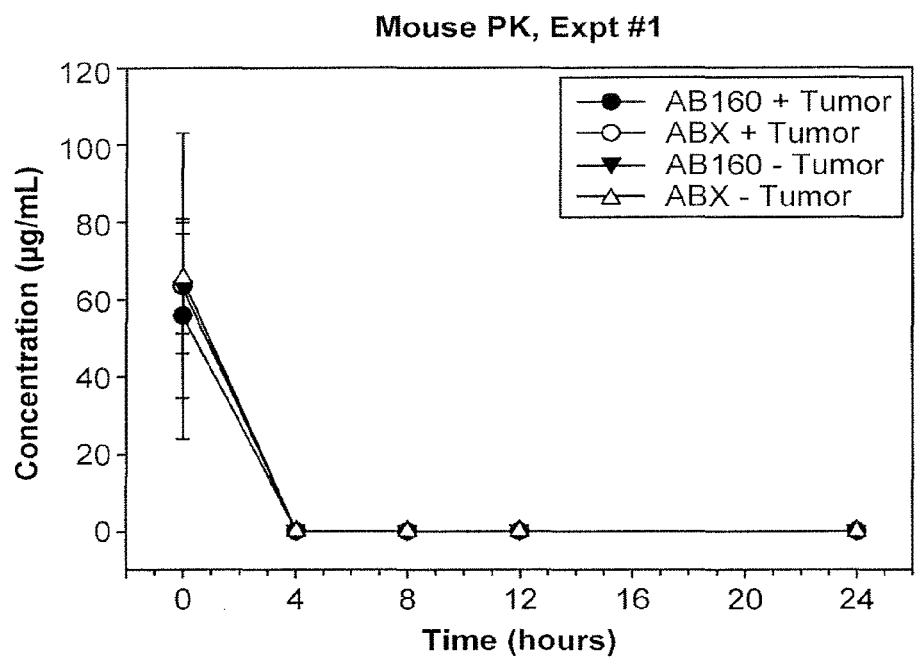
FIG. 4B demonstrates the blood paclitaxel concentration from FIG. 4A, displayed in line graph with y-axis in numeric scale.

Results of the first pk experiment are provided in FIGS. 4A and 4B. The area under the curve (AUC) and maximum serum concentration ($C_{max}$) were calculated in A375 tumor bearing and non-tumor bearing mice. In the first pk experiment the and AUC were very similar in the non-tumor bearing mice for AB160 and ABX (63.3+/−39.4 vs. 65.5+/−14.4 and 129 vs. 133 µg/ml, respectively). However, in the tumor bearing mice, the $C_{max}$ and AUC for the treatment groups were different (55.7+/−21.2 vs 63.3+/−17.3 and 112 vs 128 µg/ml, respectively) (FIG. 4C). Although this difference was not statistically significant, it is consistent with superior targeting by AB160, relative to ABX.

Figure 4D:
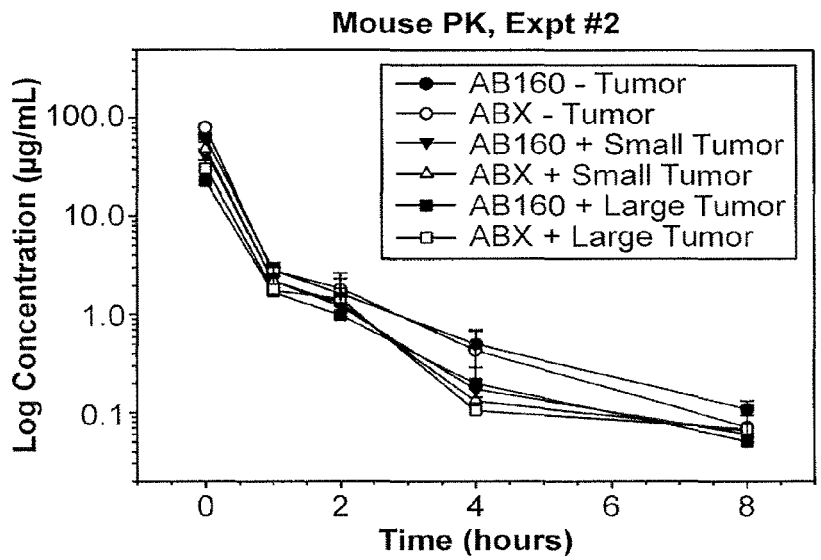
FIG. 4D demonstrates blood paclitaxel concentration displayed in line graph with y-axis in log scale from a second pharmacokinetic experiment using earlier time points (2 to 8 hours).
Figure 4E:
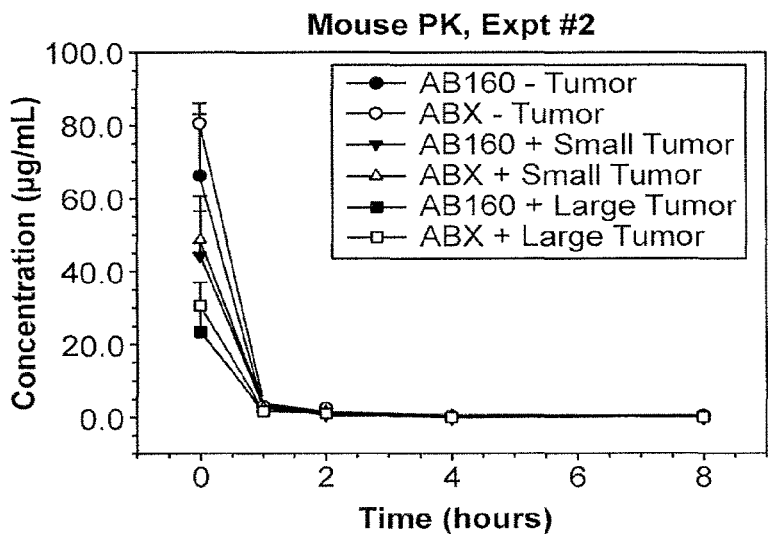
FIG. 4E demonstrates the blood paclitaxel concentration from FIG. 4D, displayed in line graph with y-axis in numeric scale.
Figure 4F:
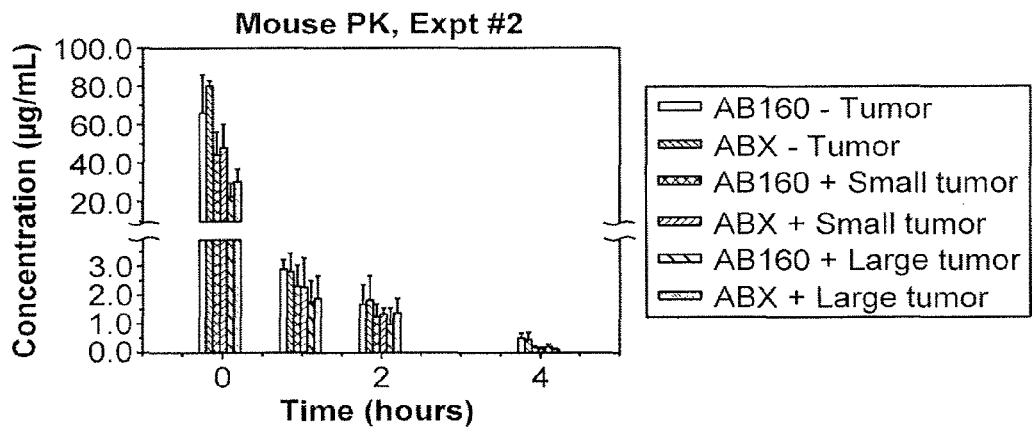
FIG. 4F shows blood paclitaxel concentration in mice in which the tumors were allowed to grow to a larger size before ABX and AB160 injections.

A second pk experiment was performed with additional early time points and large versus small tumor sizes (FIGS. 4D-4F). The results of this experiment demonstrated smaller AUC in tumor bearing mice relative to non-tumor bearing mice, with the lowest blood values of paclitaxel in the large tumor mice relative to the small tumor mice (80.4+/−2.7, 48.4+/−12.3, and 30.7+/−5.2 for ABX-treated non-tumor, small tumor and large tumor bearing mice, respectively; 66.1+/−19.8, 44.4+/−12.1 and 22.8+/−6.9 for AB160-treated). Similarly, the $C_{max}$ dropped in both treatment groups in mice with larger tumors (47.2, 28.9 and 19.7 µg/ml for ABX and 40.1, 26.9 and 15.3 µg/ml for AB160) (FIG. 4G). The AUC and $C_{max}$ of paclitaxel in blood were lower in AB160-treated mice relative to ABX-treated mice. Although not statistically significant, this data is further consistent with higher deposition of paclitaxel in the tumors treated with AB160.

Figure 4H:
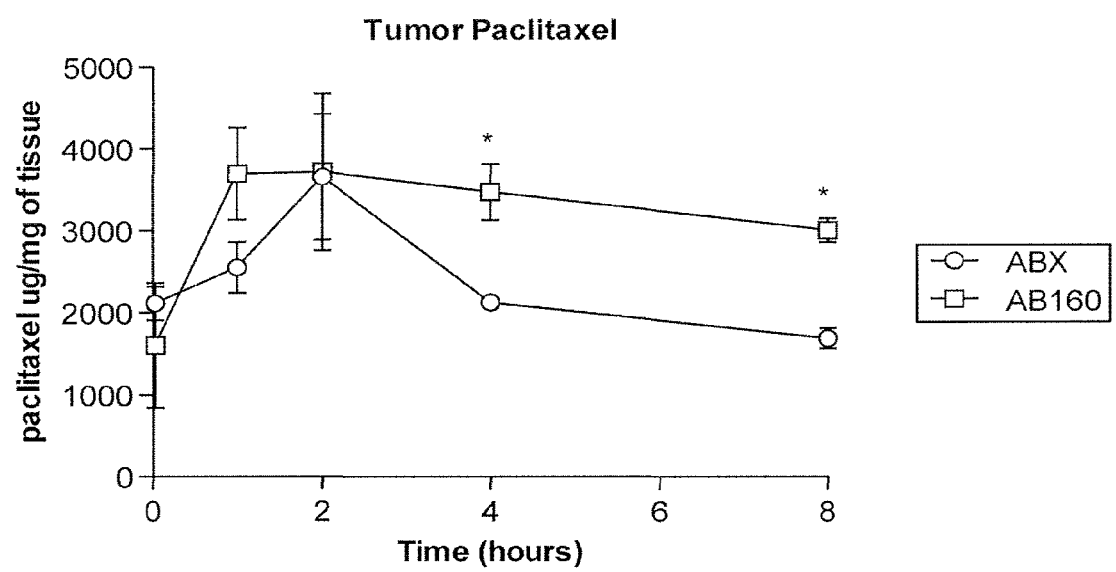
FIG. 4H shows paclitaxel concentrations in the tumors from the second mouse experiment as determined by LC-MS. Data are displayed as μg of paclitaxel/mg of tumor tissue. Student's t-test was utilized to determine if differences were significant.

To directly test this hypothesis, tumor paclitaxel concentrations by LC-MS were measured. The tumor paclitaxel concentration was significantly higher in tumors treated with AB160 relative to ABX at the 4 hour (3473 µg/mg of tissue +/−340 vs 2127 µg/mg of tissue +/−3.5; p=0.02) and 8 hour (3005 µg/mg of tissue +/−146 vs 1688 µg/mg of tissue +/−146; p=0.01) time points, suggesting paclitaxel stays in the tumor longer when targeted by the antibody (FIG. 4H). This explains the blood pk and is consistent with redistribution of drug to tissues including the tumor.

Figure 4J:
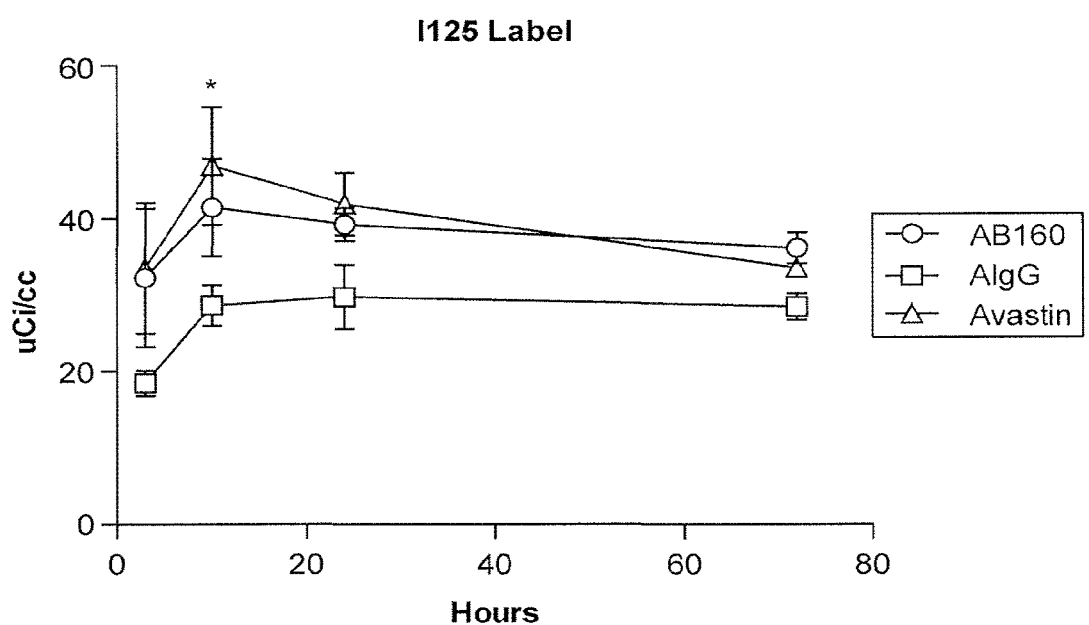
FIG. 4J shows a graphical representation of the I-125 radioactivity levels shown in FIG. 4I.

Live in vivo imaging of I-125 labeled AB160 (Abx-AvtI125) and IgG isotype bound ABX (Abx-IgGI125) confirmed the results of the LC-MS, with higher levels of I-125 in the tumor of mice treated with AB160 relative to IgG-ABX at 3 hours (32.2 uCi/g +/−9.1 vs 18.5 uCi/g +/−1.65; p=0.06) and 10 hours (41.5 uCi/g +/−6.4 vs 28.7 uCi/g +/−2.66; p=0.03) post injection (FIGS. 4I and 4J). Taken together, these data demonstrate that binding BEV to ABX alters blood pk, and this alteration is due to a redistribution of the drug to the tumor tissue as shown by both LC-MS of paclitaxel and I-125 labeling of BEV relative to an isotype matched IgG1.

Without being bound by theory, it is believed that by binding a tumor-targeted antibody to ABX, the pk is altered more dramatically than ABX alone, lowering the $C_{max}$ and AUC in the blood because of redistribution of AB160 to the tumor tissue. These results from mouse blood paclitaxel pk, tumor tissue levels of paclitaxel, and I-125 radioactivity levels in mice treated with AB160 relative to ABX alone suggest that antibody targeting of the ABX alters biodistribution of paclitaxel such that increased levels reach the tumor and are retained there for a longer period of time, yielding enhanced tumor regression.

Example 7: Binding of Other Therapeutic Antibodies

The binding of the anti-human CD20 antibody (rituxamab) and the anti-HER2/neu receptor antibody (trastuzumab) to ABX was tested to determine if other IgG therapeutic antibodies also exhibit binding to ABX when combined ex vivo.

Methods

Nanoparticles containing rituximab or trastuzumab were prepared and tested as described in the above examples.

Results

Figure 5A:
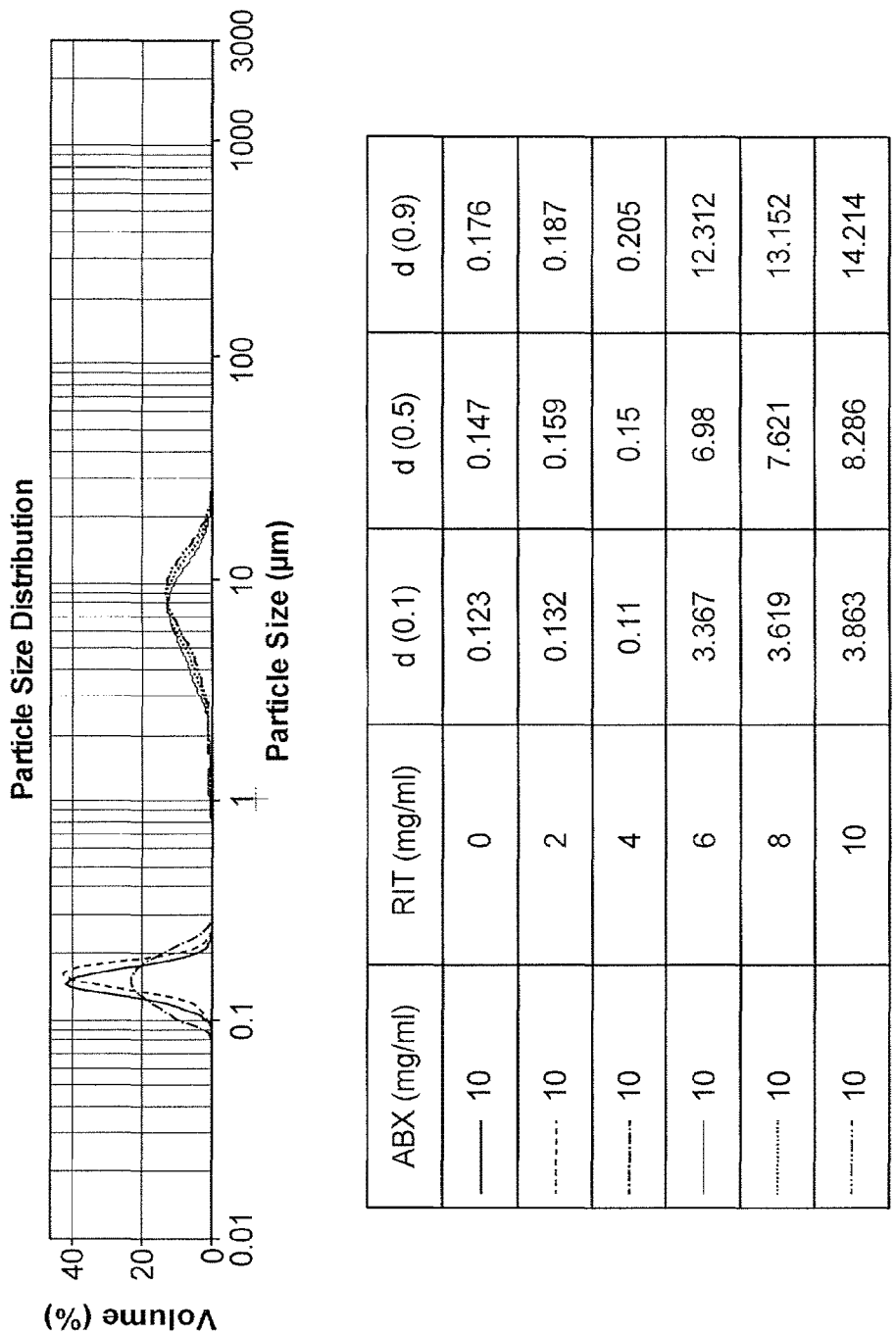
FIG. 5A shows particle size measurements and affinity of nanoparticles made with rituximab. 10 mg/ml of ABX was incubated with rituximab (RIT) at 0-10 mg/ml and light scatter technology (Mastersizer 2000) was used to determine resulting particle sizes. Data are displayed as the percent volume of particles at each size and the curves represent particle size distributions (top). The table (bottom) shows the sizes of the resulting particles at each concentration of antibody.
Figure 5B:
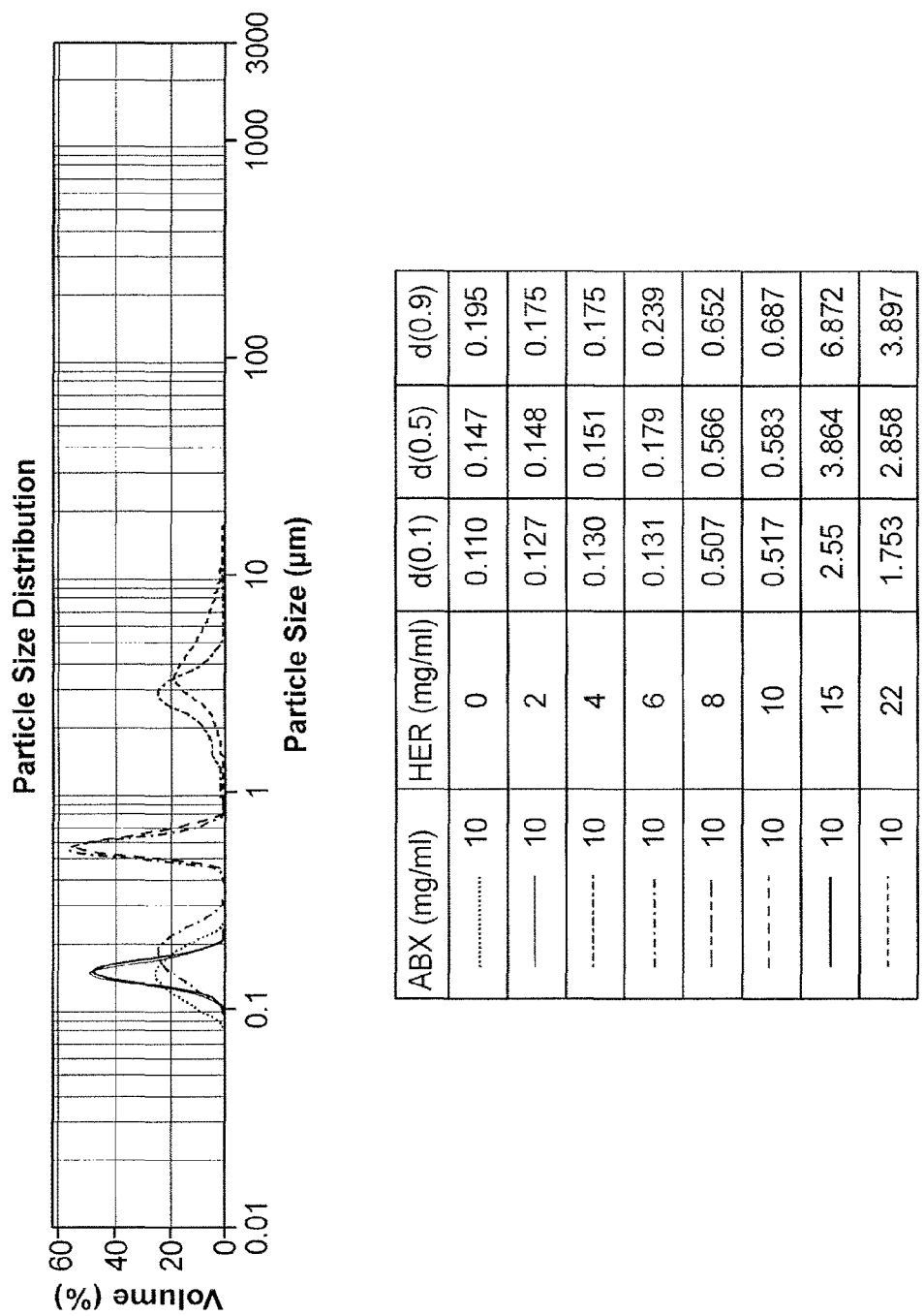
FIG. 5B shows particle size measurements and affinity of nanoparticles made with trastuzumab. 10 mg/ml of ABX was incubated with trastuzumab (HER) at 0-22 mg/ml and light scatter technology (Mastersizer 2000) was used to determine resulting particle sizes. Data are displayed as the percent volume of particles at each size and the curves represent particle size distributions (top). The table (bottom) shows the sizes of the resulting particles at each concentration of antibody.

The particle size of the complexes with both BEV and trastuzumab (HER) were very similar, with average sizes ranging from 0.157 to 2.166 μm (FIG. 2A) and 0.148 to 2.868 μm (FIG. 5B), respectively. In contrast, particles formed with rituximab became much larger at lower antibody:ABX ratios, with particle sizes ranging from 0.159 to 8.286 μm (FIG. 5A).

The binding affinities of rituximab and trastuzumab with ABX were determined by BLItz under variable pH. Both antibodies bind with relatively high affinity in the picomolar range (FIG. 5C). The rituximab affinity to ABX decreased with higher pH, but trastuzumab affinity to ABX was unaffected by pH (FIG. 5C).

Figure 6A:
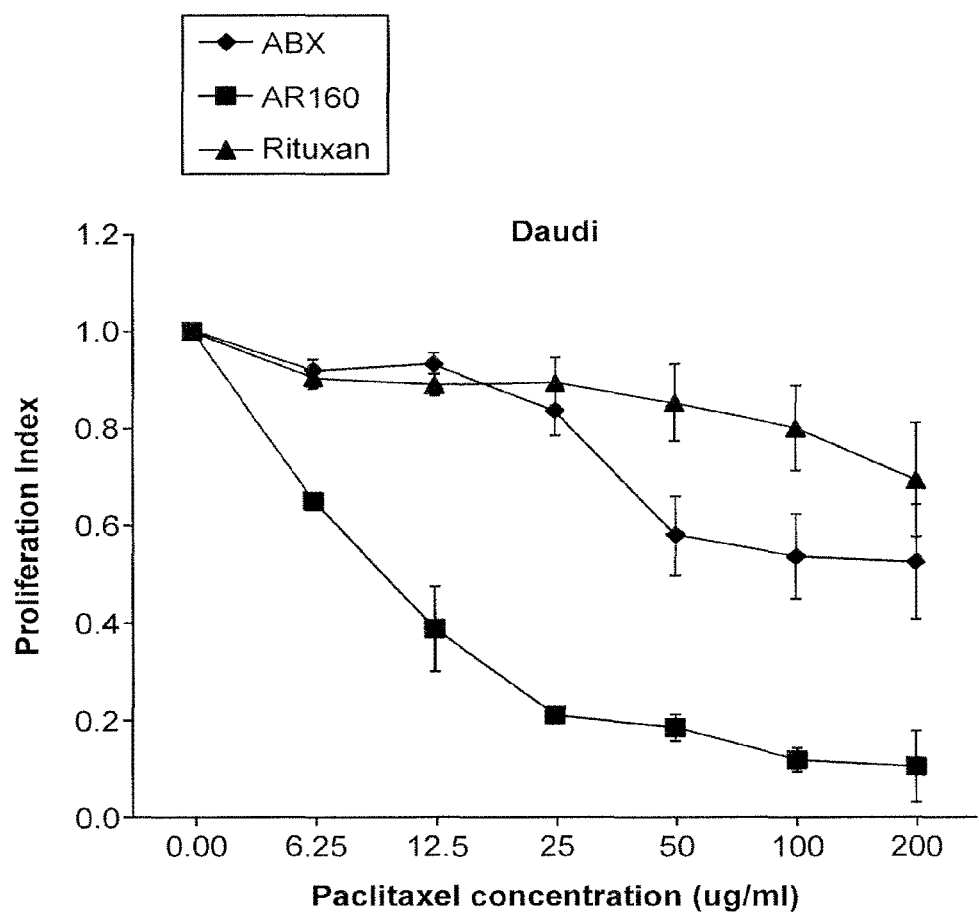
FIG. 6A shows in vitro toxicity of AR160 as tested with the CD20-positive Daudi human lymphoma cell line. The data are displayed in a graph of the proliferation index, which is the percent of FITC positive cells in treated wells relative to FITC positive cells in the untreated well (the highest level of proliferation).

The efficacy of the 160 nm particle made with rituximab (AR160) was tested in vitro and in vivo. In vitro, the B-cell lymphoma cell line Daudi was treated with AR160, ABX, or rituximab alone at increasing concentrations (0 to 200 μg/ml) of paclitaxel. AR160 ($IC_{50}$=10 μg/ml) significantly inhibited proliferation of Daudi cells treated for 24 hours (p=0.024) compared to either ABX ($IC_{50}$>200 μg/ml) or rituximab ($IC_{50}$>200 μg/ml) alone (FIG. 6A).

Figure 6B:
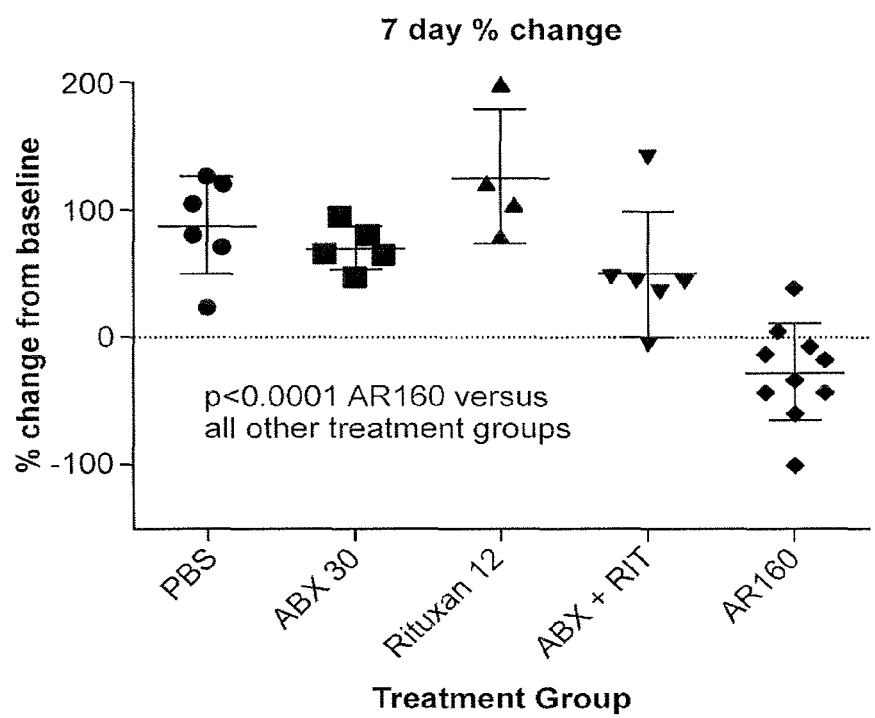
FIG. 6B shows in vivo tumor efficacy in athymic nude mice injected with $5 \times 10^6$ Daudi human lymphoma cells in the right flank. The tumors were allowed to grow to 600 mm$^3$ to 900 mm$^3$ and the mice were treated with PBS, 30 mg/kg ABX, 12 mg/kg rituximab, 12 mg/kg rituximab+30 mg/kg ABX, or AR160. Tumor response was determined at day 7 post-treatment by the percent change in tumor size from the first day of treatment. Significance was determined by Student's t-test; the percent change from baseline was significantly different between the AR160 treated mice and all other groups (p<0.0001).
Figure 6C:
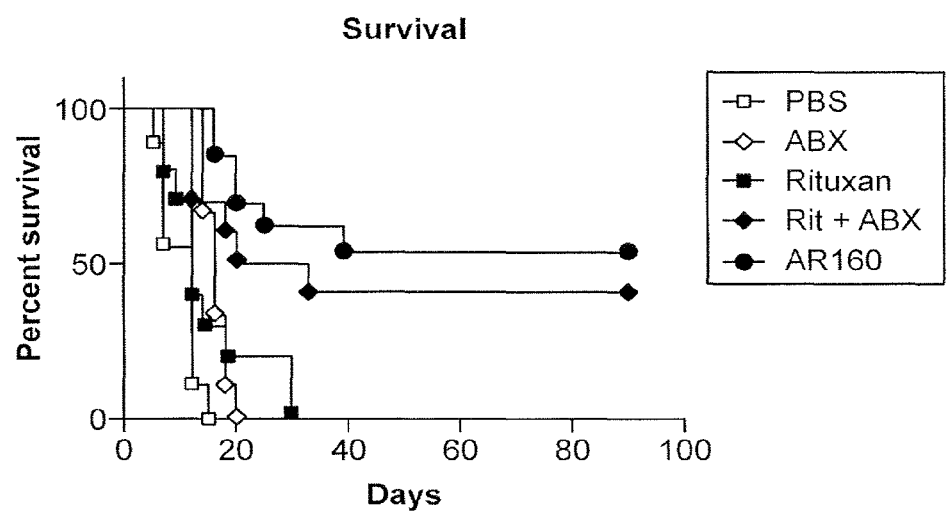
FIG. 6C shows Kaplan-Meier survival curves generated from the experiment shown in FIG. 6B. Median survival for each treatment group is shown. A Mantle-Cox test was used to determine whether survival curve differences were significant.

In vivo, a xenotransplant model of Daudi cells was established in athymic nude mice. Once tumors were established, mice were treated with PBS, ABX, rituximab, ABX and rituximab given sequentially, or AR160. On day 7 post treatment, tumors were measured and the percent change in tumor size from baseline was calculated. AR160-treated tumors regressed or remained stable, while tumors in all other treatment groups progressed (FIG. 6B). The percent change from baseline tumor size in the AR160 group compared to all other groups was significant (p<0.0001). The mice treated with AR160 had a significantly longer median survival of greater than 60 days compared to 12, 16, and 12 days for mice treated with PBS (p<0.0001), ABX (p<0.0001), or rituximab (p=0.0002), respectively (FIG. 6C). However, the difference in median survival was not significant between AR160 and the sequentially treated groups (p=0.36). This may be because the rituximab binds to the tumor cells and remains on the cell surface, allowing the subsequently-administered ABX to bind to the antibody when it enters the tumor site, unlike BEV which binds a soluble target and not a cell surface marker.

Example 8: Binding of Other Chemotherapy Drugs to AB160

Figure 7A:
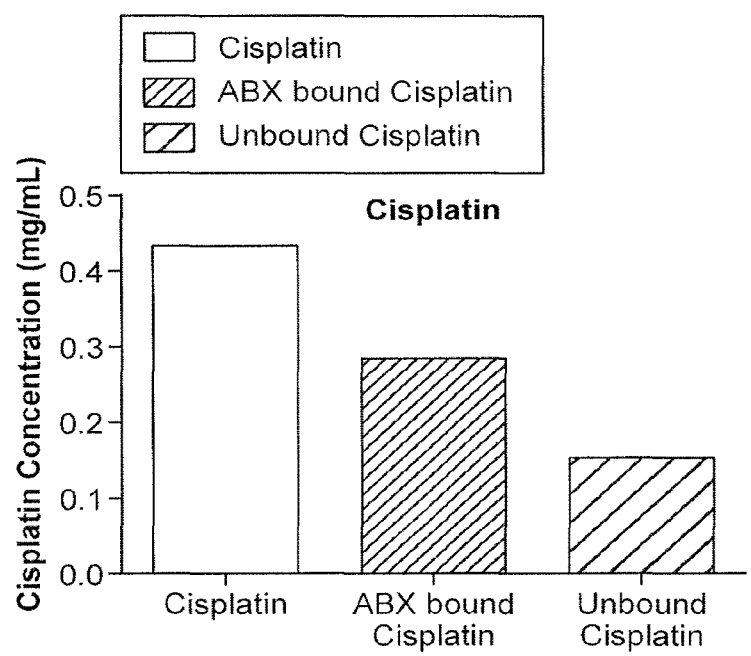
FIG. 7A demonstrates addition of another chemotherapy drug (cisplatin) cisplatin to AB160. ABX (5 mg/ml) was incubated with cisplatin (0.5 mg/ml) at room temperature for 30 minutes and free cisplatin was measured by HPLC in the supernatant after ABX particulate was removed. The quantity of free cisplatin was subtracted from the starting concentration to determine the quantity of cisplatin that bound to the ABX. The data are displayed in a column graph, along with the starting concentration (cisplatin).

The efficacy of other chemotherapy drugs to form functional nanoparticles was evaluated.
Methods
Nanoparticles containing cisplatin were prepared and tested as described in the above examples.
Results
To test if another chemotherapy drug could bind to the AB160 particles, cisplatin and ABX were co-incubated and the amount of free cisplatin remaining in the supernatant was measured by HPLC. Approximately 60% (i.e., only 40% remains in the supernatant) of the cisplatin bound to the ABX (FIG. 7A).

Figure 7B:
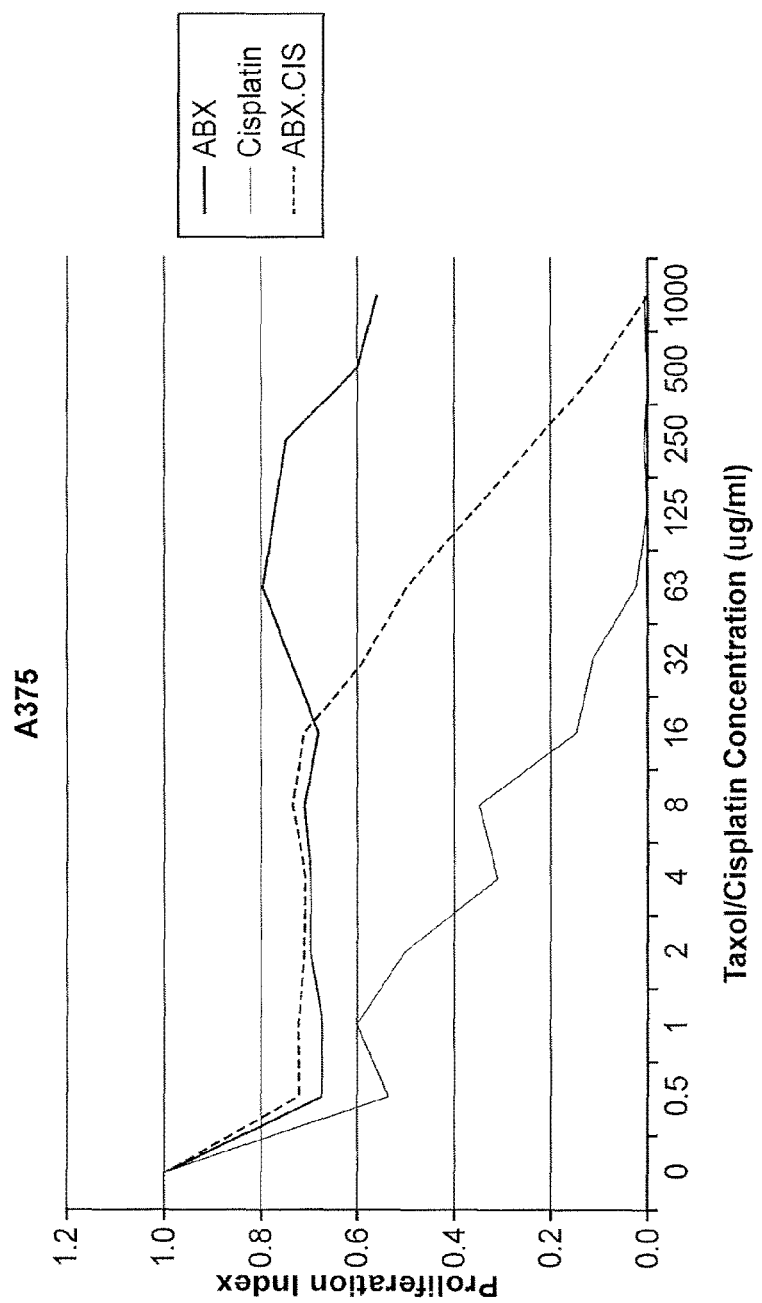
FIG. 7B shows the toxicity of cisplatin-bound ABX (AC) in a proliferation assay of A375 human melanoma cells. After 24 hours of drug exposure and EdU incorporation, the cells were fixed, permeabilized and labeled with a FITC conjugated anti-EdU antibody. The data is displayed in a graph of the proliferation index, which is the percent of FITC positive cells in treated wells compared to FITC positive cells in the untreated well (the highest level of proliferation).

Next, tumor toxicity of AC relative to ABX and cisplatin alone was tested using A375 cells. The complexes were centrifuged to remove highly toxic unbound cisplatin, and reconstituted in media to ensure that any additional toxicity of AC relative to ABX is due only to ABX-bound cisplatin. For parity, the ABX only was centrifuged in a similar manner. AC ($IC_{50}$=90 μg/ml) inhibited proliferation of A375 cells to a greater extent than ABX alone ($IC_{50}$>1000 μg/ml) (FIG. 7B). The diminished toxicity in this experiment relative to other toxicity experiments is due to some loss of drug in the centrifugation step, but the comparison of ABX to AC remains relevant.

Figure 7C:
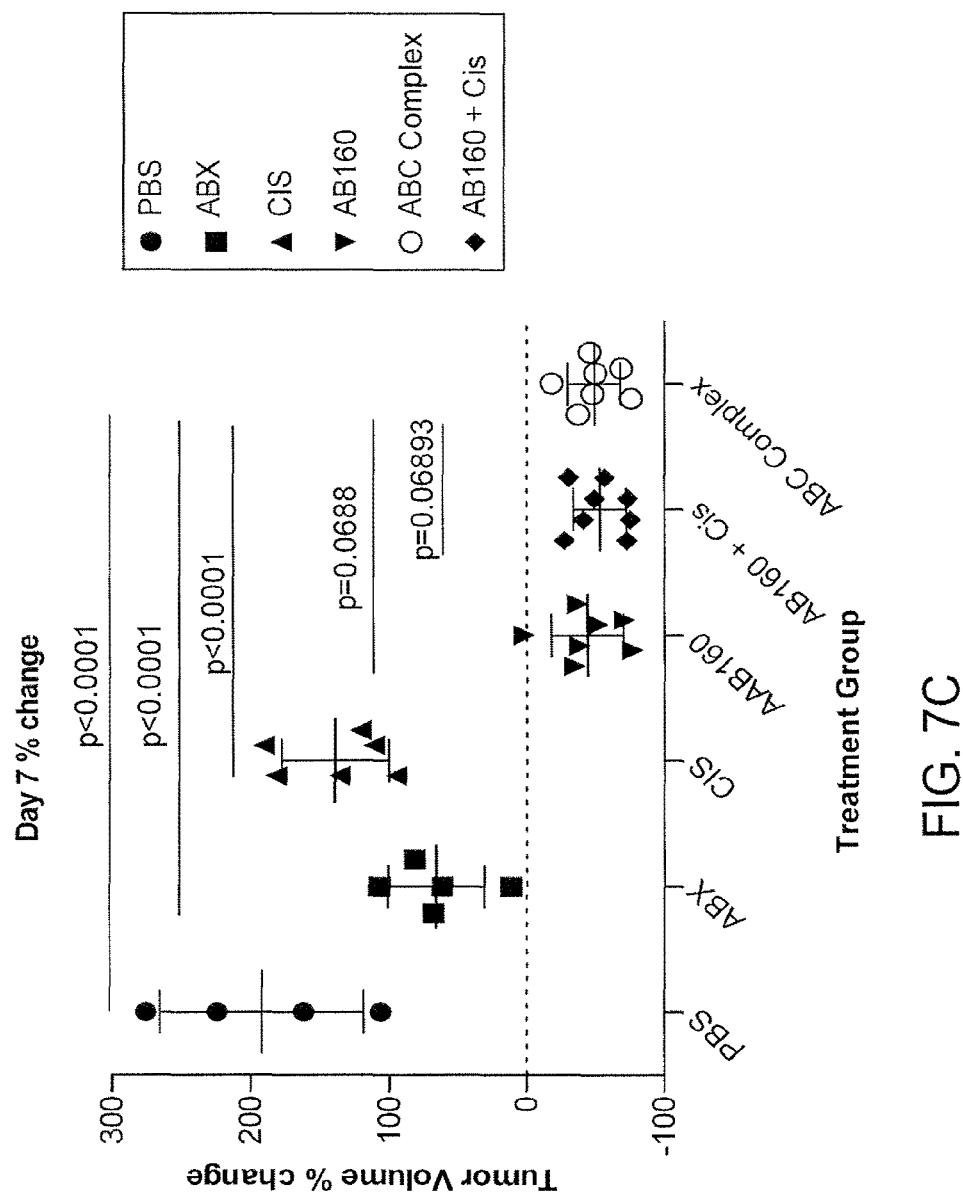
FIG. 7C shows in vivo tumor efficacy of AC (ABC complex; cisplatin-bound ABX) in athymic nude mice injected with $1 \times 10^6$ A375 human melanoma cells in the right flank. The tumors were allowed to grow to 600 mm$^3$ to 900 mm$^3$ and the mice were treated with PBS, 30 mg/kg ABX, 2 mg/kg cisplatin, AB160, 2 mg/kg cisplatin+AB160 or ABC 160. Tumor response was determined at day 7 post-treatment by the percent change in tumor size from the day of treatment. Significance was determined by Student's t-test; the percent change from baseline was significantly different between the ABC 160 treated mice and PBS-, cisplatin-, or ABX-treated mice (p<0.0001). There was no significant difference between the AB160, AB160+cisplatin, and ABC 160 treated groups for day 7 post-treatment percent change from baseline.
Figure 7D:
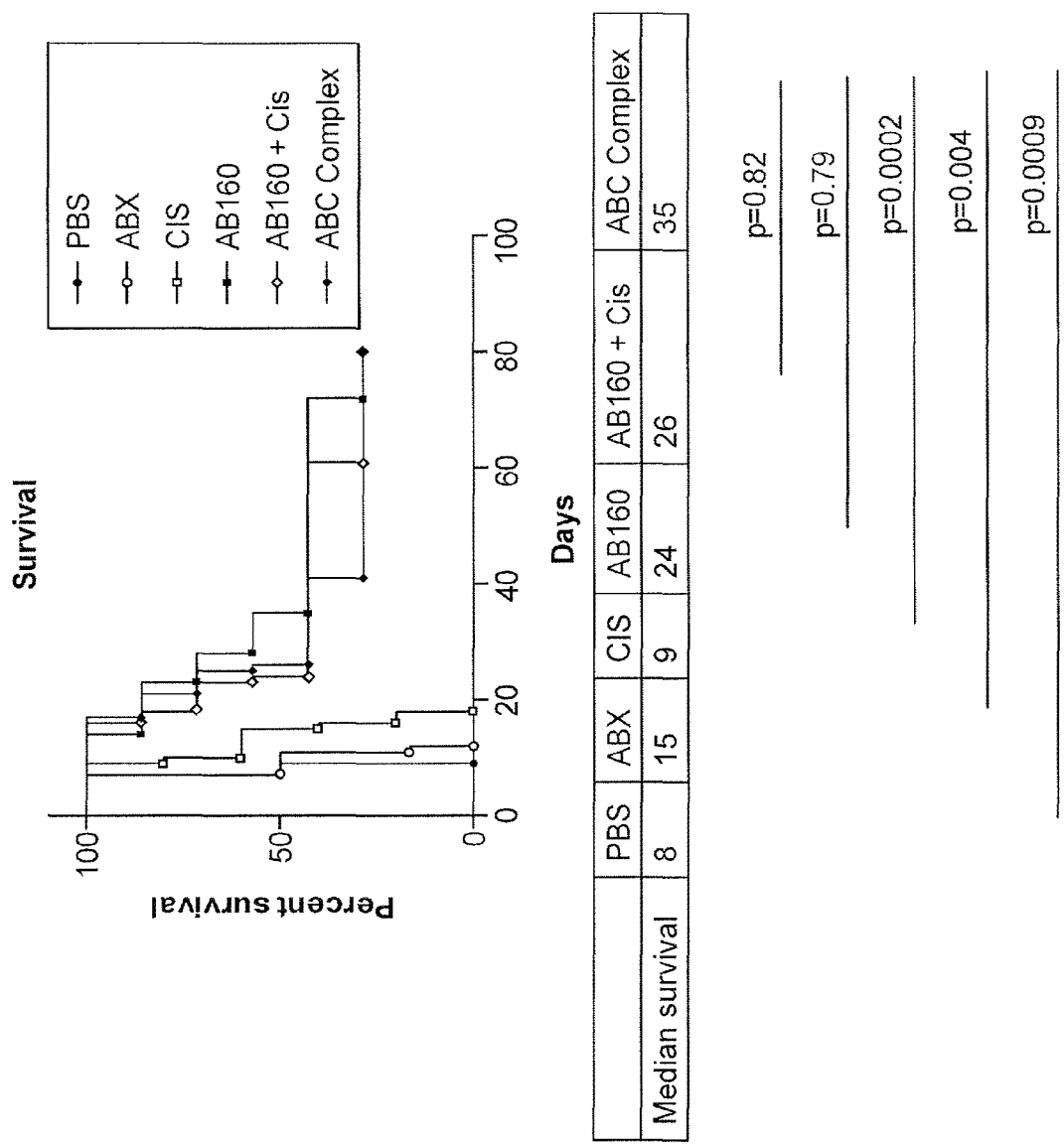
FIG. 7D shows Kaplan-Meier survival curves generated based on the experiment shown in FIG. 7C and median survival for each treatment group is shown. A Mantle-Cox test was used to determine whether survival curve differences were significant.

To determine the tumor toxicity of cisplatin-containing AB160 complexes, AB160 was co-incubated with cisplatin to form cisplatin containing particles (ABC complex). The ABC complex was tested in the A375 melanoma xenotransplant model relative to each drug alone and AB160. Tumors treated with AB160, AB160 cisplatin given sequentially, and the ABC complex all showed regression in tumor size at 7 days post treatment (FIG. 7C), but the ABC complex conferred the longest median survival (35 days, relative to AB160 and AB160+cisplatin at 24 and 26 days, respectively). Although the difference was not statistically significant (p=0.82 and 0.79) (FIG. 7D), the data is consistent with benefits of the ABC complex to long-term survival rates.

These data demonstrated that the albumin portion of the ABX provides a platform for other therapeutic antibodies to bind, such as rituximab and trastuzumab, as well as other chemotherapy agents (e.g., cisplatin), which all had similar efficacy in vitro and in vivo as AB160.

Together these data demonstrate a simple way to construct a versatile nano-immune conjugate, which allows multiple proteins or cytotoxic agents to be bound to a single albumin scaffold. Improved efficacy of the targeted drug relative to the single agents alone was demonstrated in the mouse model, which is at least in part due to altered pk of the antibody-targeted drug. Furthermore, without being bound by theory, it is believed that the versatility of the presently disclosured nano-immune conjugate that does not require a linker or target cell internalization will overcome the obstacles faced by other nanomedicines in translating results from mice to humans.

Example 9: Lyophilization of AB160

AB160 was synthesized by adding 8 mg (3200 of bevacizumab to 20 mg of Abraxane. 1.66 ml of 0.9% saline was then added for a final volume of 2 ml for a final concentration of 4 mg/ml bevacizumab and 10 mg/ml Abraxane, and the mixture was allowed to incubate at room temperature for 30 minutes in a 15 ml polypropylene conical tube.

After the 30 minute room temperature incubation, the mixture was diluted 1:2 in 0.9% saline to 2 mg/ml and 5 mg/ml bevacizumab and Abraxane, respectively. These are the concentrations of the 2 drugs when prepared by the pharmacy for administration to patients.

AB160 was divided into twenty 200 μl aliquots in 1.5 ml polypropylene eppendorfs and frozen at −80° C.

Once frozen, the aliquots were lyophilized overnight with the Virtis 3L benchtop lyophilizer (SP Scientific, Warmister, Pa.) with the refrigeration on. A lyophilized preparation was generated.

The dried aliquots were stored at room temperature in the same 1.5 ml polypropylene eppendorfs. These samples were readily reconstituted in saline at room temperature for 30 minutes, followed by centrifugation for 7 minutes at 2000× g. The resulting sample was then resuspended in the appropriate buffer, as needed.

By comparison, a sample that was dried with heat and a speed vacuum was impossible to reconstitute.

Example 10: Testing of Lyophilized Preparations

Samples were reconstituted at different time points after lyophilization and tested for their physical properties against ABX, and freshly made AB160.

Particle size distribution was evaluated as described above.

VEGF binding was evaluated by incubation of the sample with VEGF for 2 hours at room temperature, centrifuged at 2000×g for 7 minutes. The amount of VEGF bound to the pellet (corresponding to the nanoparticles) or remaining in the supernatant was measured with ELISA.

Paclitaxel activity was assessed by cytotoxicity against A375 cells in vitro.

Figure 8A:
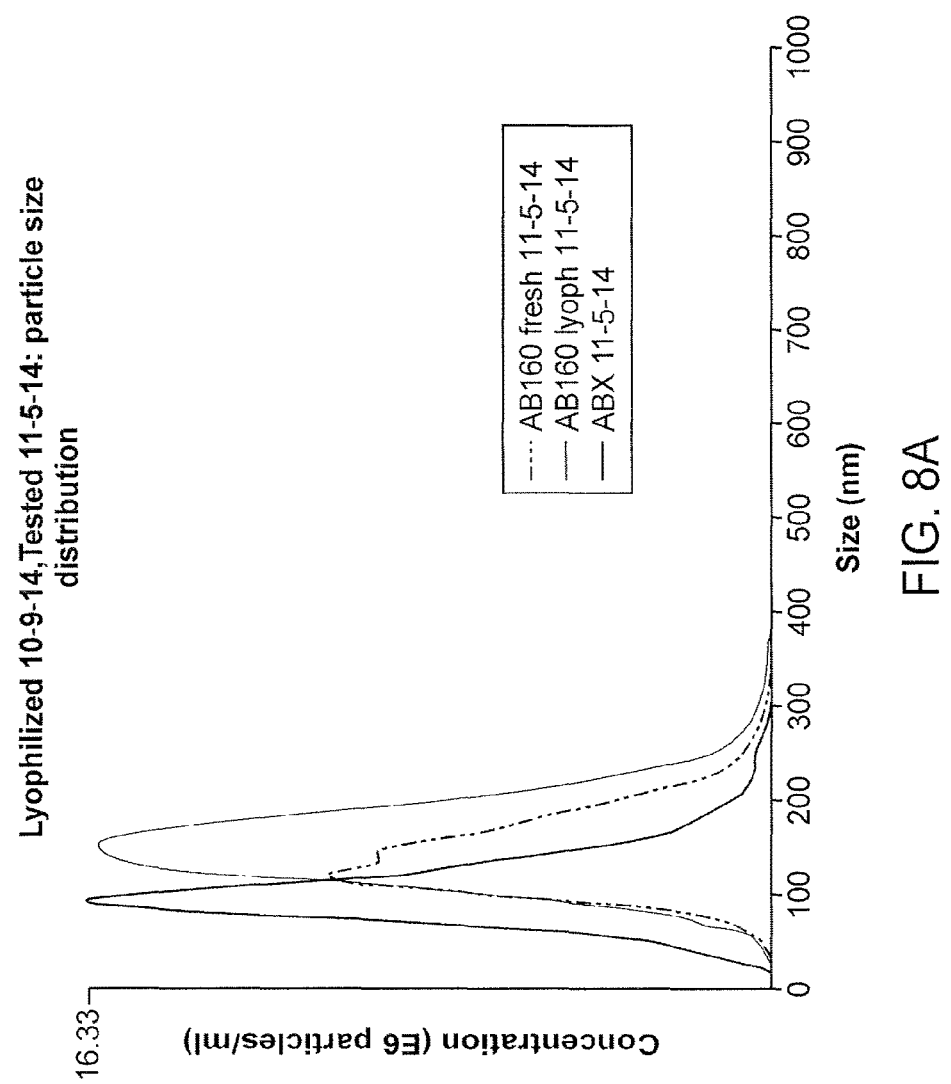
FIG. 8A shows the size distribution of AR160 nanoparticles that were lyophilized, stored at room temperature for one month, and reconstituted, as compared to fresh AB160 or ABX alone.
Figure 8B:
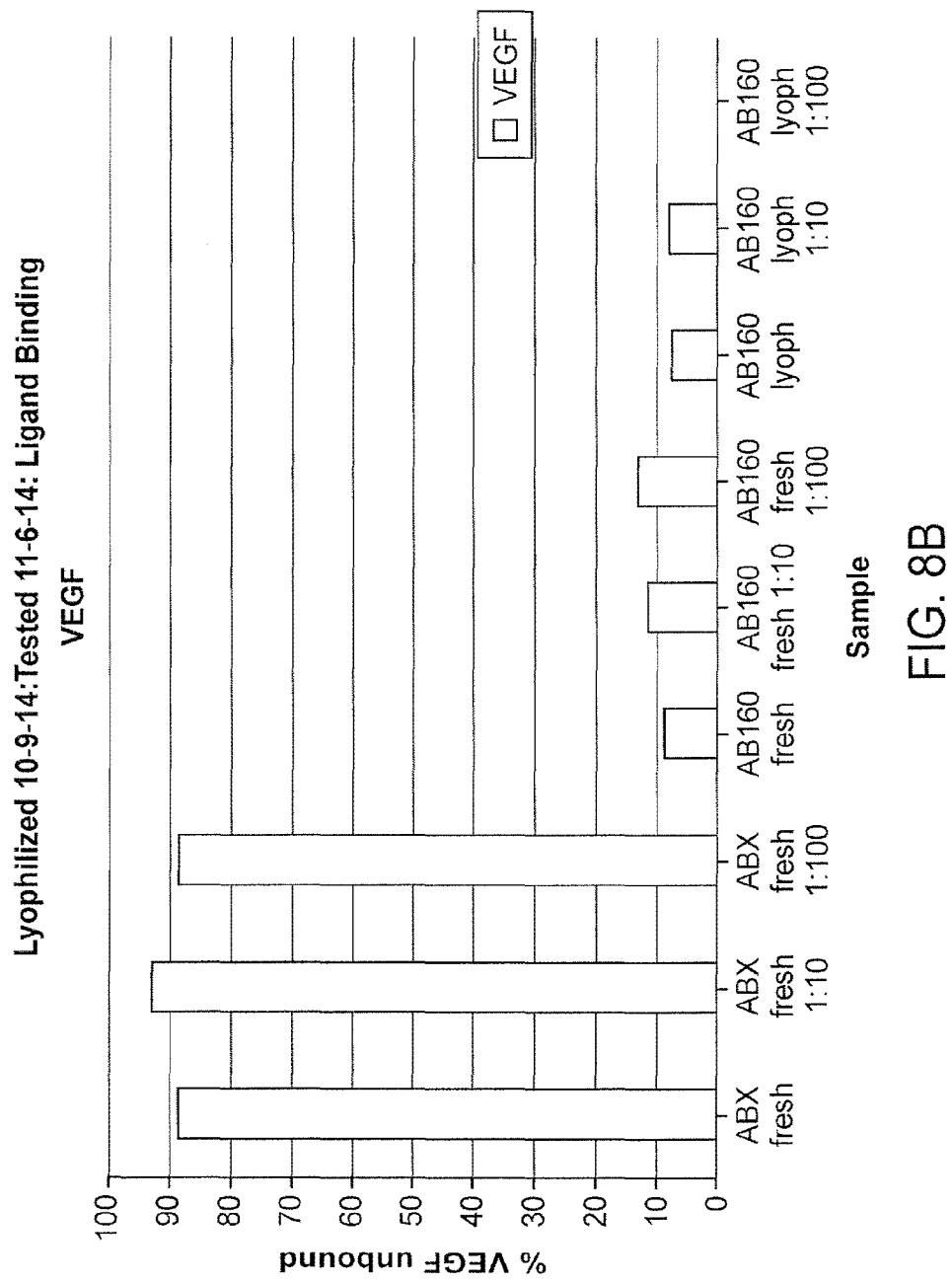
FIG. 8B shows the ligand (VEGF) binding ability of AB160 nanoparticles that were lyophilized, stored at room temperature for one month, and reconstituted, as compared to fresh AB160 or ABX alone.
Figure 8C:
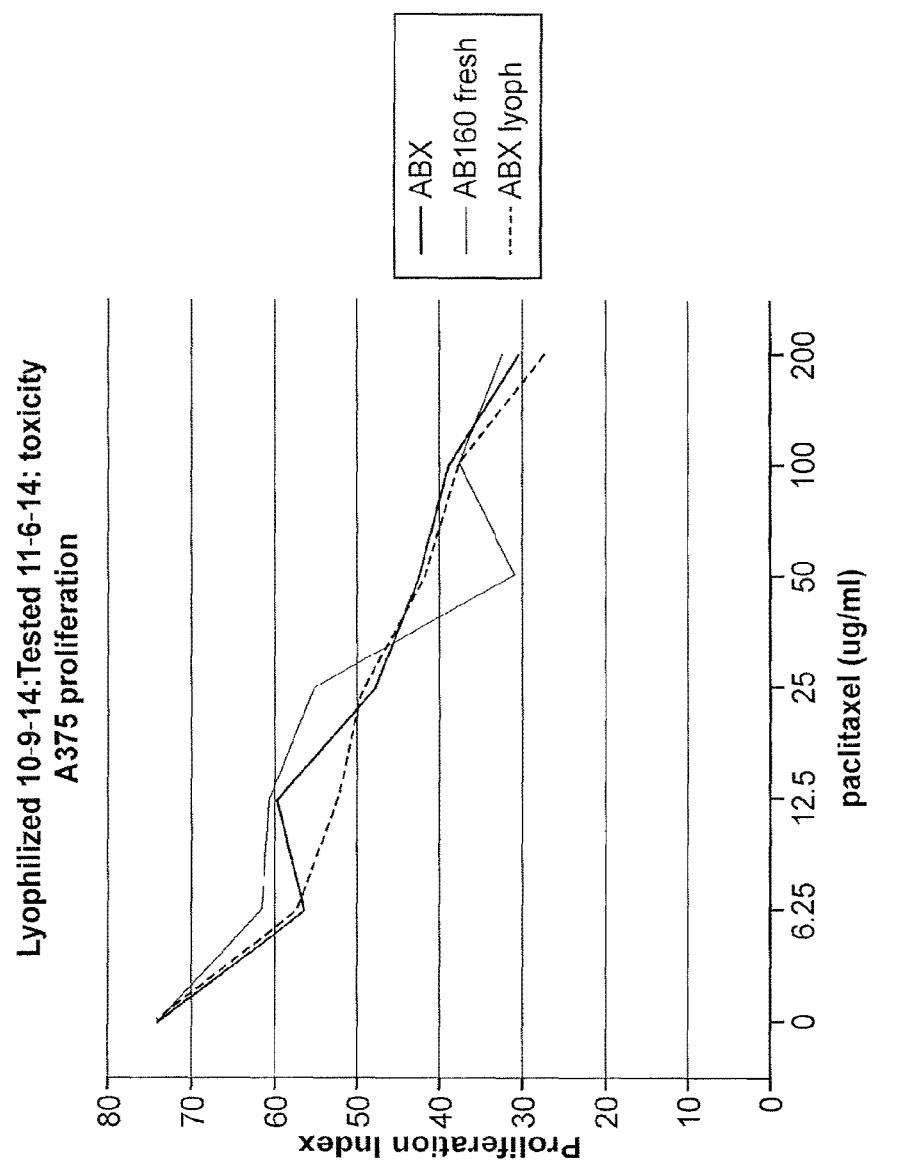
FIG. 8C shows in vitro cancer cell toxicity of AB160 nanoparticles that were lyophilized, stored at room temperature for one month, and reconstituted, as compared to fresh AB160 or ABX alone.
Figure 8F:
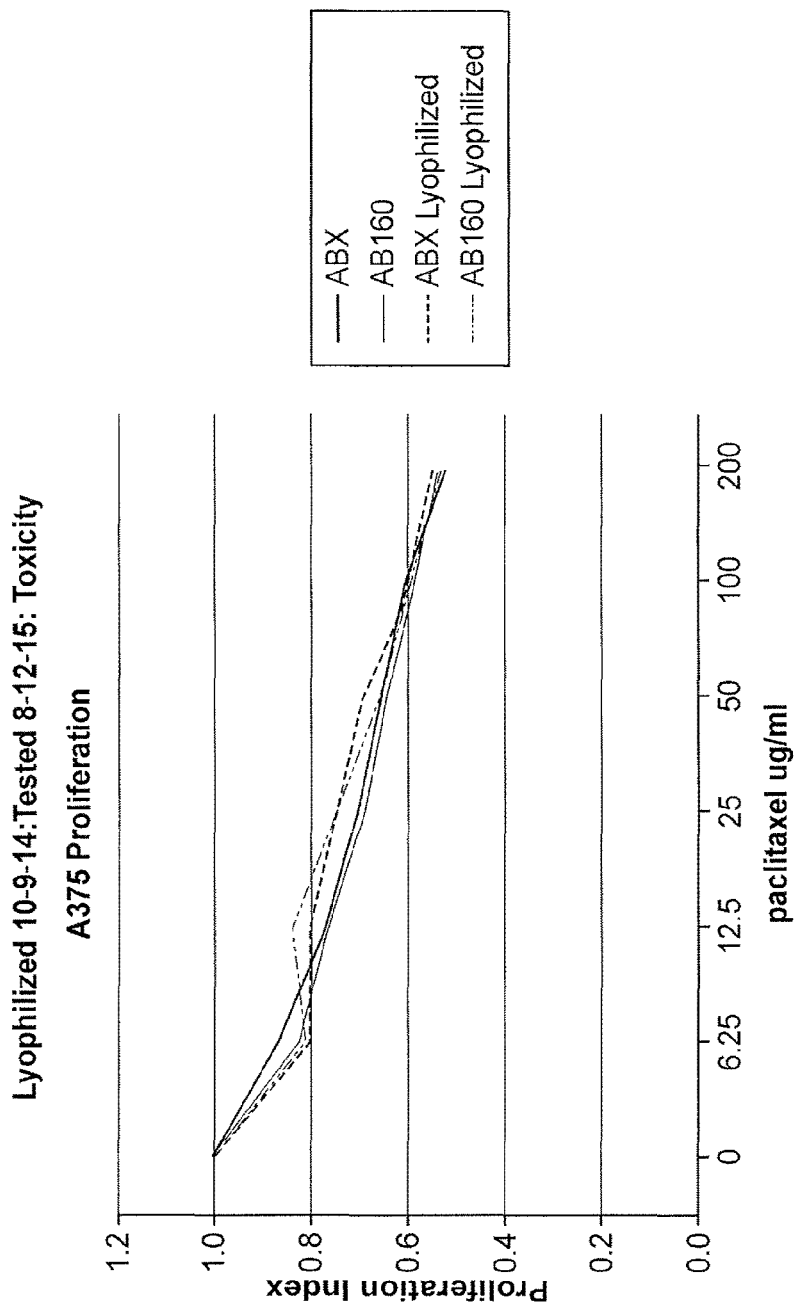
FIG. 8F shows in vitro cancer cell toxicity of AB160 nanoparticles that were lyophilized, stored at room temperature for ten months, and reconstituted, as compared to fresh AB160 or ABX alone.

Surprisingly, lyophilization did not significantly affect either the particle size, VEGF binding, or the activity of paclitaxel as shown by the ability to inhibit cancer cell proliferation. This result held for lyophilized samples stored for 1 month (FIGS. 8A-8C) or 10 months (FIGS. 8D-8F).

Further surprising is that these results were observed with nanoparticles lyophilized without the use of cryoprotectants or other agents that may adversely effect human therapeutic use.

Example 11: Efficacy of AB160 in Humans

AB160 was tested in a phase 1, first-in-man, clinical trial testing the safety of AB160 administered to patients with metastatic malignant melanoma that have failed prior therapies. The study utilizes a classical 3+3, phase 1 clinical trial design, testing 3 different doses of AB160 in the following schema:

TABLE 4

| Dose Level | AB-complex Both drugs MUST be reduced | |
|---|---|---|
| | ABX dose | Accompanying BEV dose |
| 3 | 175 mg/m$^2$ | 70 mg/m$^2$ |
| 2 | 150 mg/m$^2$ | 60 mg/m$^2$ |
| 1* | 125 mg/m$^2$ | 50 mg/m$^2$ |
| −1 | 100 mg/m$^2$ | 40 mg/m$^2$ |
| −2 | 75 mg/m$^2$ | 30 mg/m$^2$ |

*Dose level 1 refers to the starting dose.

The doses were selected relevant to doses of Abraxane currently used in clinical practice. AB160 was made prior to each treatment dose. Treatments were administered as a 30 minute intravenous infusion on days 1, 8 and 15 of a 28-day treatment cycle. Treatments were continued until intolerable toxicity, tumor progression or patient refusal. Prior to every treatment cycle, patients were evaluated for toxicity; tumor evaluations were performed every other cycle (RECIST).

The study is accompanied by formal (in-patient) pharmacokinetic studies associated with dose 1 of cycles 1 and 2 of therapy.

Five patients have been administered AB160, at 100 mg/m2 of ABX and 40 mg/m2 of BEV, of which four have been analyzed.

TABLE 5

Disease course in Phase I study
Disease Course: Dose Level 100 mg/m$^2$

| Patient | number of cycles | response | PFS time | off, treatment reasons | follow-up time |
|---|---|---|---|---|---|
| 1 | 8 | stable | 238 | off, progression | 444+ |
| 2 | 6 | stable | 400+ | off, toxicity | 400+ |
| 3 | 1 | — | 182+ | off, toxicity | 182+ |
| 4 | 6 | stable | 181 | off, progression | 203+ |

PFS refers to median progression free survival, i.e. the number of days of treatment before the cancer recurred. Adverse events are listed below. There was no dose limiting toxicity (DLT), i.e. the adverse events were not linked to the dose of AB160. More detail is provided in Table 6

TABLE 6

Adverse events in Phase I study

| patient | toxicity | DLT |
|---|---|---|
| 1 | grade 2 lymphopenia | NO |
| 2 | grade 3 neutropenia and leukopenia grade 2 hypertension and anemia | NO |
| 3 | grade 2 colonic perforation, fatigue, and blood bilirubin increase | NO |
| 4 | grade 2 neutropenia | NO |

TABLE 7

Treatment Course: Dose Level 100 mg/m$^2$

| patient | number of cycles administered | number of cycles where day 15 omitted | cycles where day 15 omitted | reasons day 15 omitted | number of dose reductions taken | cycles where dose reduction taken | reason for dose reductions | status |
|---|---|---|---|---|---|---|---|---|
| 1 | 8 | 0 | | | 1 | 4 | grd 2 sensory neuropathy | off, progression |
| 2 | 6 | 3 | 1, 2, 4 | grd 3 neutropenia and leukopenia- all 3 cycles | 2 | 3, 5 | cycle 3: grade 3 neutropenia and leukopenia cycle 5: grade 3 neutropenia, leukopenia, and fatigue and grd 2 sensory neuropathy | off toxicity persistent grd 2 sensory neuropathy |
| 3 | 1 | | | | | | | off toxicity grd 2 colonic perforation |

TABLE 7-continued

Treatment Course: Dose Level 100 mg/m²

| patient | number of cycles administered | number of cycles where day 15 omitted | cycles where day 15 omitted | reasons day 15 omitted | number of dose reductions taken | cycles where dose reduction taken | reason for dose reductions | status |
|---|---|---|---|---|---|---|---|---|
| 4 | 6 | | | | 2 | 3, 5 | grd 2 sensory neuropathy-both cycles | off, progression |

The mean PFS was 7.6 months and the median was 7.0 months.

Comparison with Other Clinical Trials

The following table shows other published clinical studies for taxane therapy for metastatic melanoma.

TABLE 8

Taxane therapy for metastatic melanoma

| Study or Author | N | Rx regimens | PFS | OS |
|---|---|---|---|---|
| Hauschild | 135 | C = AUC 6 (q21)<br>P = 225 mg/m2; D1 (q21) | 4.5 | 10.5 |
| Flaherty | 411 | C = AUC 6 (q21)<br>P = 225 mg/m2; D1 (q21) | 4.9 | 11.3 |
| N057E | 41 | C = AUC2; D1, 8 15 (q28) | 4.5 | 11.1 |
| | 35 | A = 100 mg/m2; D1, 8, 15 (q28) | 4.1 | 10.9 |
| N047A | 53 | C = AUC 6; D1 (q28)<br>P = 80 mg/m2; D1, 8, 15 (q28)<br>B = 10 mg/kg; D1, 15 (q28) | 6.0 | 12.0 |
| BEAM | 71 | C = AUC 5; D1 (q21)<br>P = 175 mg/m2; D1 (q21) | 4.2 | 8.6 |
| | 143 | C = AUC5; D1 (q21)<br>P = 175 mg/m2; D1 (q21)<br>B = 15 mg/kg; D1 (q21) | 5.6 | 12.3 |
| N0775 | 51 | C = AUC6 (5); D1 (q28)<br>A = 100 (80) mg/m2; D1, 8, 15 (q28)<br>B = 10 mg/kg; D1, 15 (q28) | 6.2 | 13.9 |
| Spitler | 50 | A = 150 mg/m2; D1, 8, 15 (q28)<br>B = 10 mg/kg; D1, 15 (q28) | 7.6 | 15.6 |

C = carboplatin,
P = paclitaxel,
A = nab-paclitaxel,
B = bevacizumab
References:
Hauschild: Hauschild et al., (2009) *J Clin Oncol.* 27(17): 2823-30
Flaherty: Flaherty et al., (2010) *J Clin Oncol.* 28: 15s (suppl; abstr 8511)
N057E: Kottschade et al., (2010) *Cancer* 117(8): 1704-10
N057A: Perez et al., (2009) *Cancer* 115(1): 119-27
BEAM: Kim et al., (2012) *J Clin Oncol.* 30(1): 34-41
N0775: Kottschade et al., (2013) *Cancer* 119(3): 586-92
Spitler: Boasberg et al., (2011) *J Clin Oncol.* 29 (suppl; abstr 8543)

In the current trial, administration of AB160 particles is equivalent to a dose of 100 mg/m² of abraxane, and 40 mg/m² of bevacizumab. The only study that used BEV and ABX alone was Spitler. Spitler, however, used a higher dose of ABX. The present study also used less than 10% of the dose of BEV reported in previous studies, if the doses are adjusted to the average patient (assumed to have a surface area of 1.9 m² and a mass of 90 kg).

Spilter also examined patients who had not been previously treated, while the current study examined patients who had failed previous treatments. Ineffective prior treatment not only takes time from the expected PFS, but selects for cancer cells that are more resistant to treatment, and typically leaves a patient in poorer physical condition. Thus, the PFS for a population of patients on a "rescue" therapy (as here, with AB160) is expected to have a lower PFS than a naïve population. This can be seen in a Phase 2 clinical trial (Hersh et al., *Cancer*, January 2010, 116:155) that examined both rescue and naïve patients with Abraxane alone. For previously treated patients with Abraxane alone, the PFS was 3.5 months. Hersh et al. *Ann. Oncol* 2015, (epub Sep. 26, 2015), reported a 4.8 month PFS for naïve patients treated with ABX alone.

TABLE 9

Performance of AB160 in a limited study against published data

| Study | Prior treatment | ABX dose in average patient (relative dose) | BEV dose in average patient (relative dose) | PFS (months) |
|---|---|---|---|---|
| AB160 | Yes | 190 mg/patient (100 mg/m²) | 76 mg/patient (40 mg/m²) | 7.0 |
| Spitler | No | 285 mg/patient (150 mg/m²) | 900 mg/patient (10 mg/kg) | 8.3 |
| Hersh 2010 | Yes | 190 mg/patient (100 mg/m²) | — | 3.5 |
| Hersh 2010 | No | 285 mg/patient (150 mg/m²) | — | 4.5 |
| Hersh 2015 | No | 285 mg/patient (150 mg/m²) | — | 4.8 |

Thus, early results of the Phase I clinical trial with AB160 indicate an increase in PFS in late-stage metastatic malignant melanoma in previously treated patients. This increase is particularly surprising given that the PFS was greater than those in Spitler, who were chemotherapy naïve and were given a higher dose of Abraxane, and an almost 12 fold higher dose of bevacizumab. The dose of BEV used in AB160 is far lower than any other study, so the best comparison is not Spitler, but Hersh.

Thus, the ABX/BEV complex (AB160) is superior to sequential administration of ABX and BEV, or ABX alone, and achieves this superior result with a very low effective dose of BEV. The data is therefore consistent with AB160 having improved targeting of the chemotherapeutics to the tumor, and that this targeting is mediated by BEV. It is possible that the ABX nanoparticle aids in targeting the BEV to the tumor, as albumin is selectively taken up by tumors. It is also possible that the existence of the BEV/ABX complex shows greater stability in vivo than Abraxane.

Example 12: Follow Up Study to Investigate Whether Pretreatment with BEV Improves Targeting Following the general protocol above, athymic nude mice were injected with $1 \times 10^6$ A375 human melanoma cells in the right flank and then treated with PBS, 12 mg/kg BEV, 30 mg/kg ABX, AB160, or pretreated with 1.2 mg/kg BEV and, 24 hr later, AB160. Data is represented at day 7-post and day 10-post treatment as tumor volume in mm³. F 11A-E track tumor size over 10 days. Only mice treated with AB160 (with or without pretreatment with BEV) showed a reduction in average tumor volume. See also FIG. 11F and FIG. 11G.

Figure 11A:
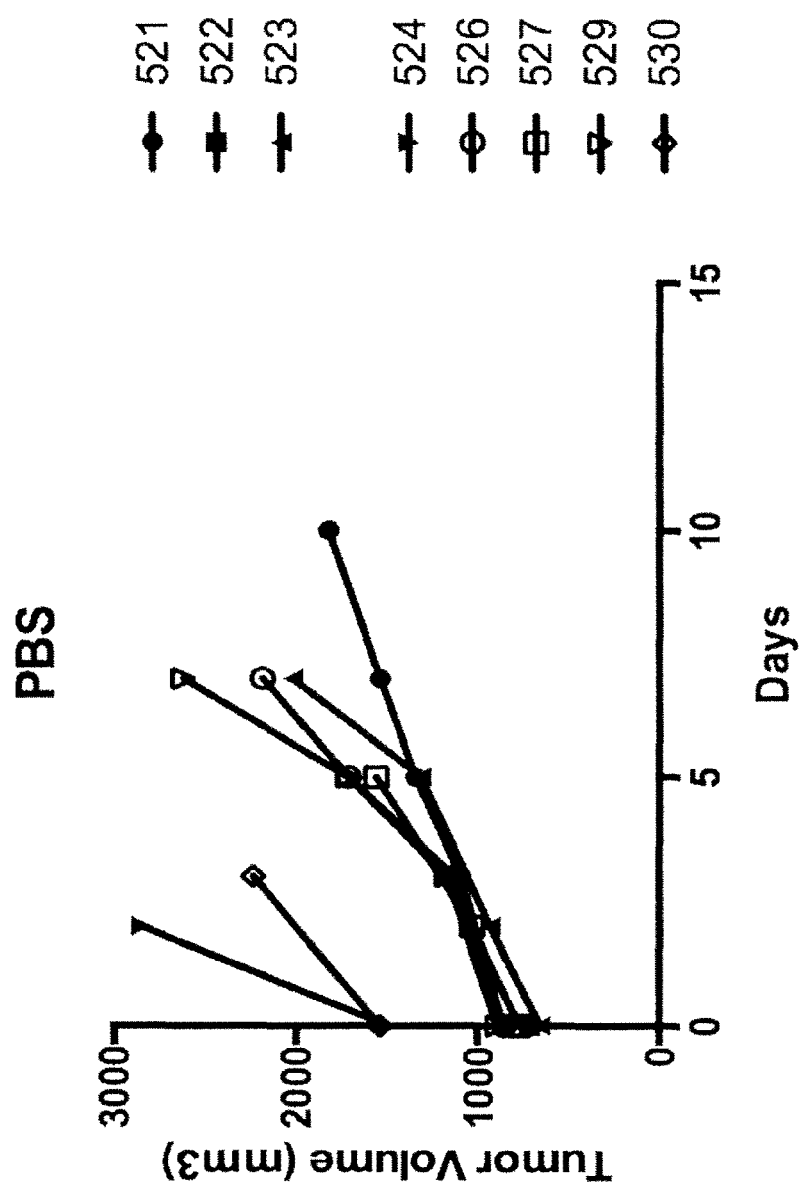
FIGS. 11A-E show in vivo testing of athymic nude mice injected with $1 \times 10^6$ A375 human melanoma cells in the right flank and treated with (FIG. 11A) PBS, (FIG. 11B) 12 mg/kg BEV, (FIG. 11C) 30 mg/kg ABX, (FIG. 11D) AB160, or (FIG. 11E) pretreated with 01.2 mg/kg BEV and, 24 hr later, AB160. Data is represented at day 7-post and 10-day treatment as tumor volume in $mm^3$.
Figure 11B:
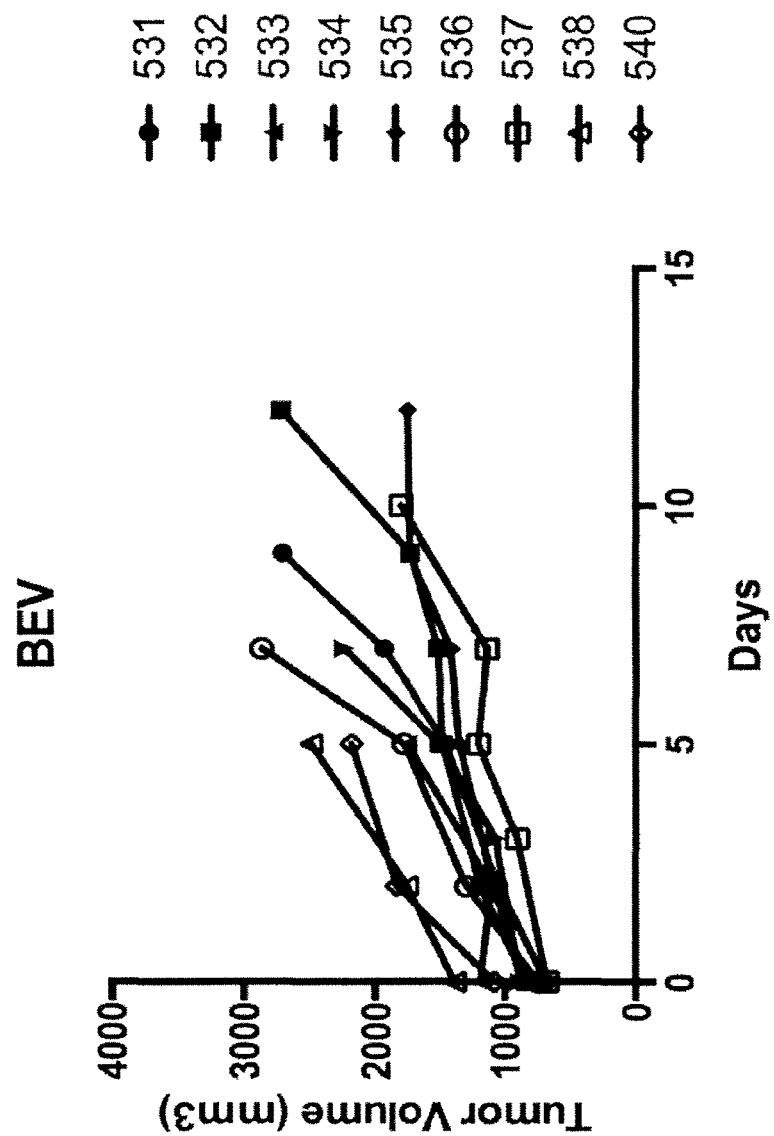
Figure 11C:
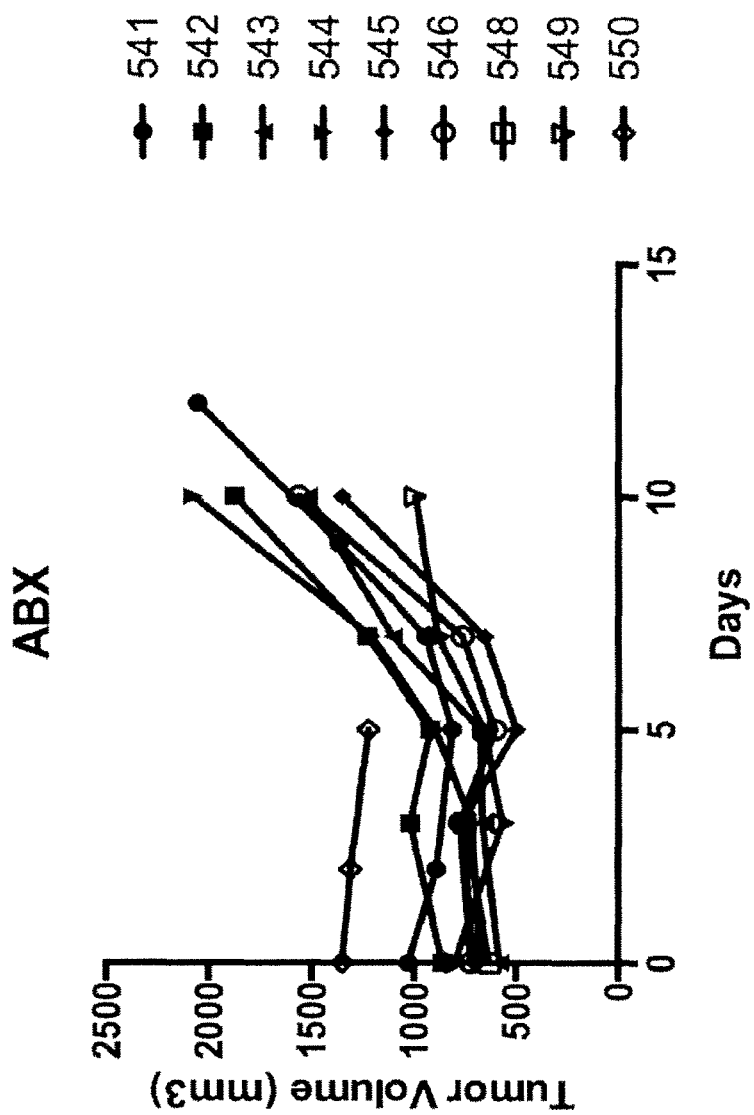
Figure 11D:
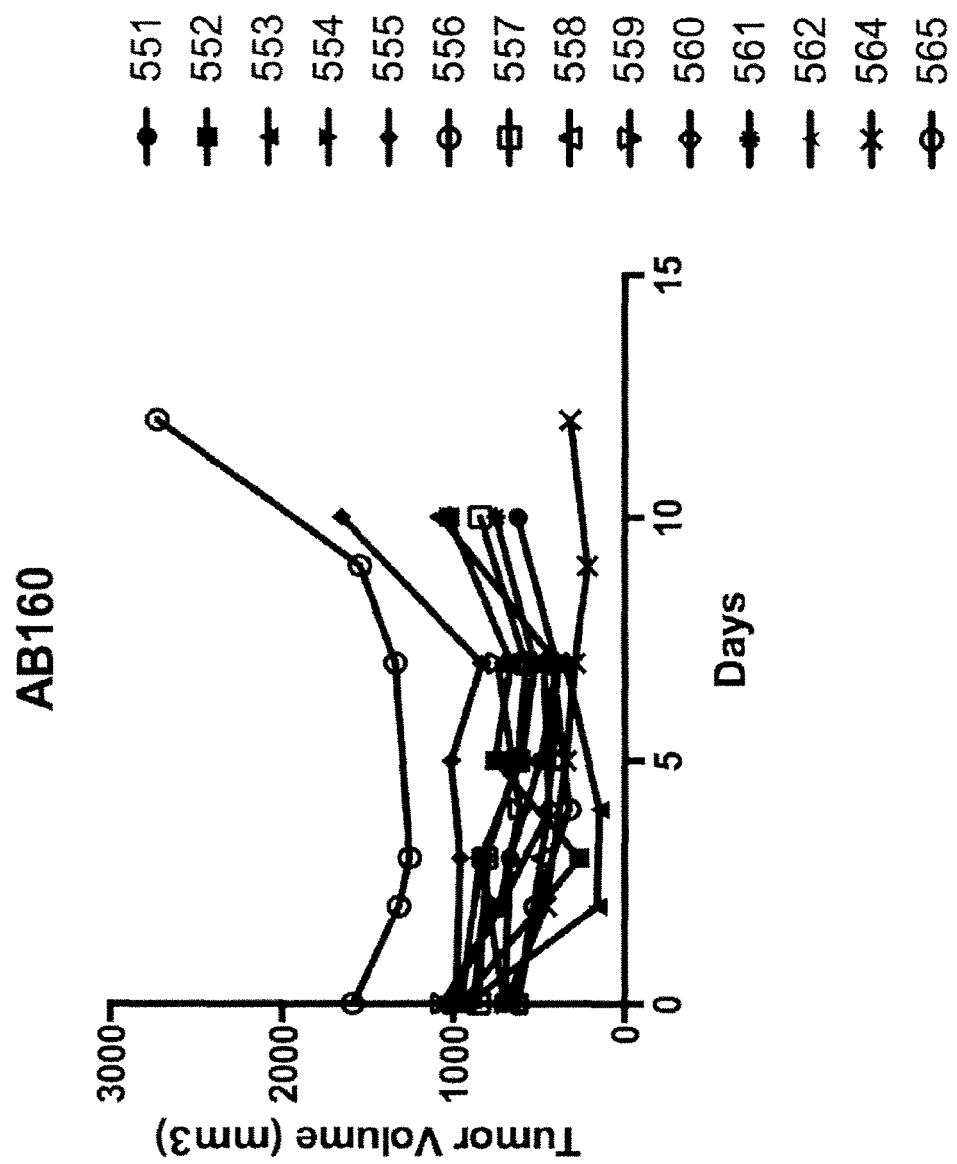
Figure 11E:
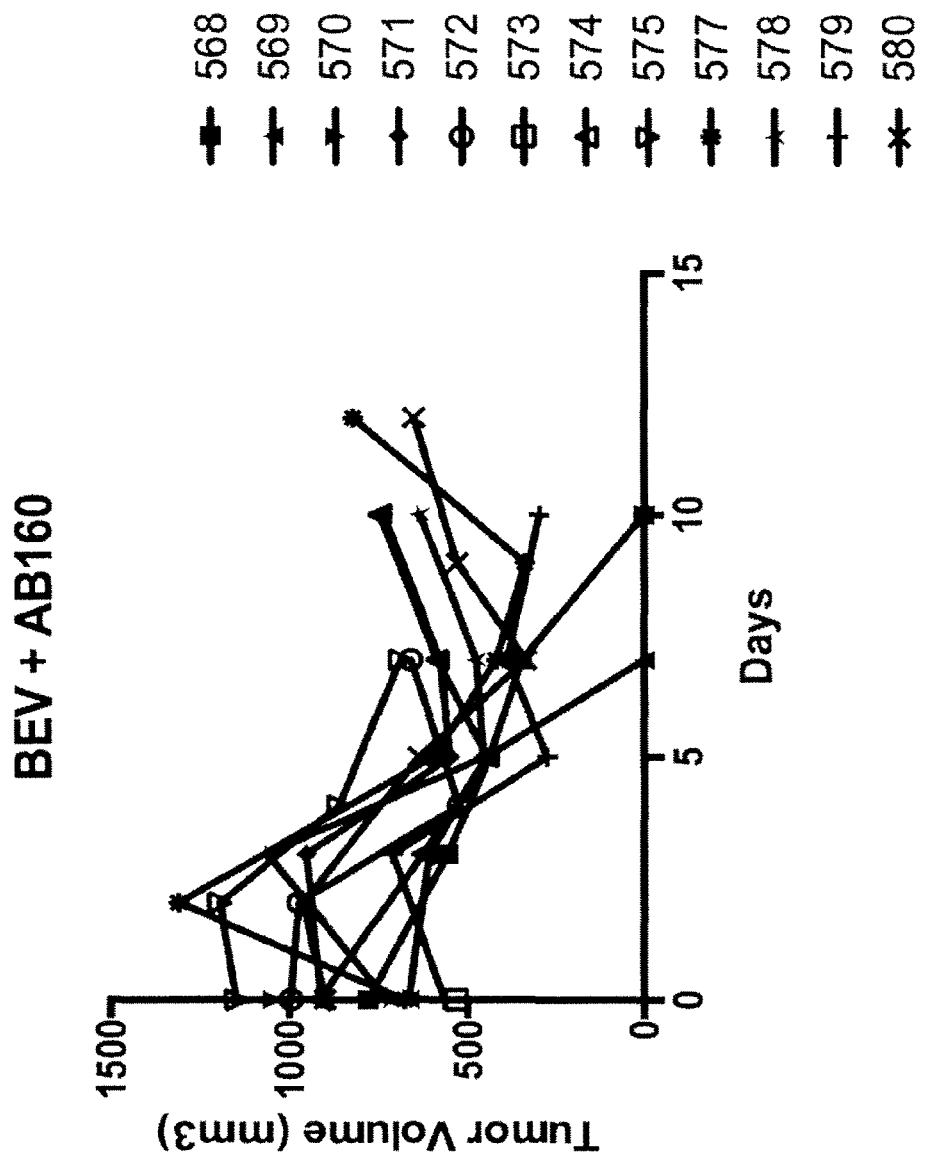
Figure 11F:
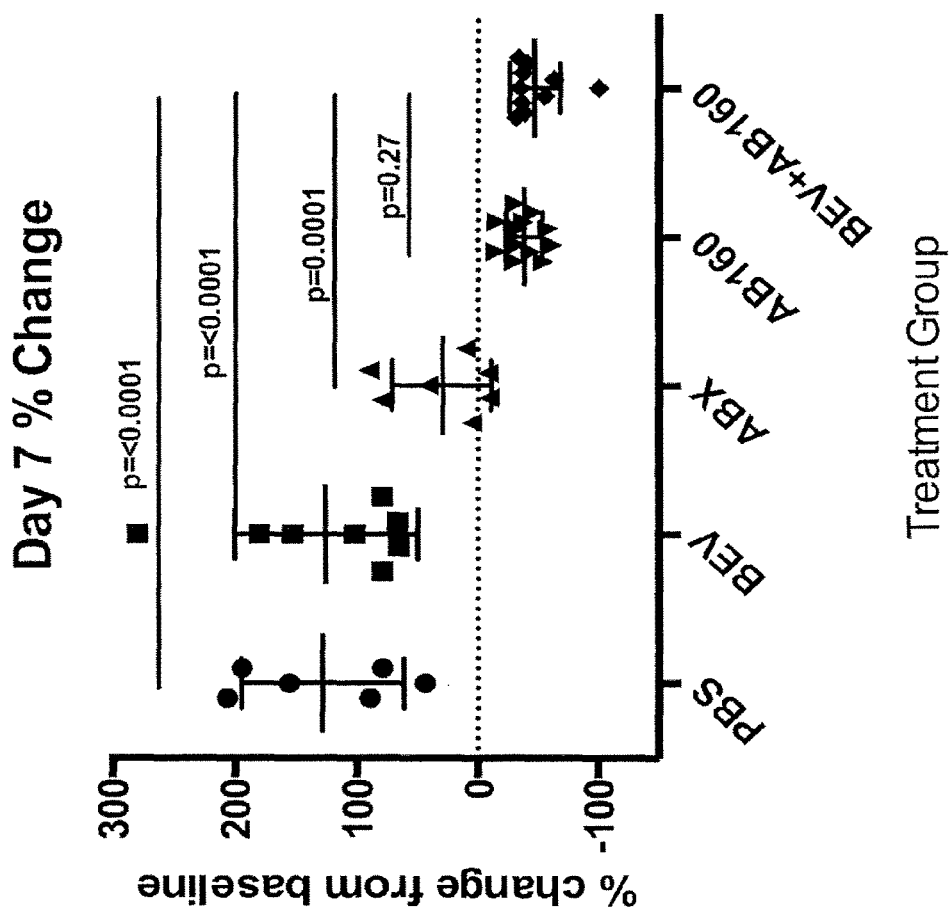
FIG. 11F summarizes the day 7-post treatment data from FIGS. 11A-E.
Figure 11G:
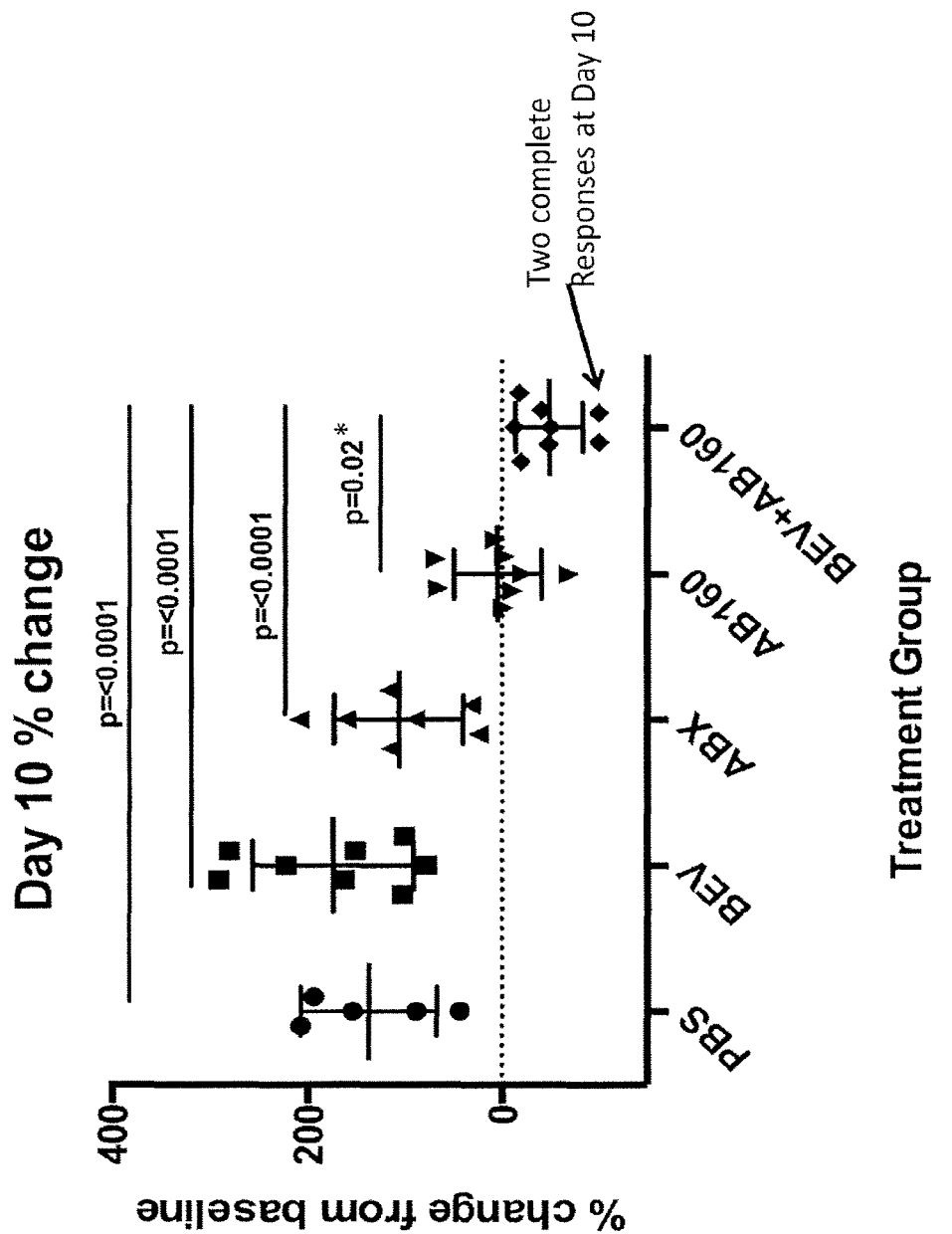
FIG. 11G summarizes the day 10-post treatment data from FIGS. 11A-E.

The day 7-post treatment data, as summarized in FIG. 11F, show that pretreatment with BEV was associated with a stastically significant reduction in tumor volume over control or BEV alone (p≤0.0001), or ABX alone (p≤0.0001).

The day 10-post treatment data, as summarized in FIG. 11G, again show that pretreatment with BEV was associated with a stastically significant reduction in tumor volume over control or BEV alone (p≤0.0001), or ABX alone (p≤0.0001). Pretreatment with BEV before AB160 was also associated with a reduction in tumor volume over AB160 alone (p=0.02), with complete response in two mice.

In this experiment, a 12 mg/kg dose of BEV was not therapeutic. The amount of BEV added in the pretreatment group was only 1.2 mg/kg, which is 1/10 the usual dose in mice. Yet pretreatment with a subtherapeutic dose appears to show improved efficacy of the AB160 nanoparticle. This data support the idea that pretreatment with a subtherapeutic amount of BEV can clear systemic levels of VEGF, leaving a greater relative concentration at the tumor such that tumor-associated VEGF targeting by the AB160 nanoparticles is more effective.

Example 13: Alternative Means of Delivering Nanoparticles

It is contemplated that nanoparticles of this invention can be directly delivered to the tumor. For example, nanoparticles can be delivered via intra-arterial cannula or by direct injection into the tumor. In such embodiments, it is contemplated that large nanoparticles (e.g., 580 nm or 1130 nm) can be delivered by direct injection into or proximate to a tumor.

What is claimed is:

1. A lyophilized composition comprising nanoparticle complexes having an outside surface, wherein each of the nanoparticle complexes comprises:
   a) albumin;
   b) antibodies having a human epidermal growth factor receptor (HER) binding portion; and
   c) paclitaxel;
said nanoparticle complexes being lyophilized, and wherein upon reconstitution with an aqueous solution, the HER binding portion of said antibodies are arranged on the outside surface of the nanoparticle complexes and are capable of binding to HER in vivo.

2. The lyophilized composition of claim 1 that is stable at about 20° C. to about 25° C. for at least 3 months.

3. The lyophilized composition of claim 1, wherein each of the nanoparticle complexes comprises between about 400 and about 800 antibodies.

4. The lyophilized composition of claim 1, wherein less than 0.01% of nanoparticle complexes in the composition have a size greater than 800 nm.

5. The lyophilized composition of claim 1, wherein the average size of the nanoparticle complexes is less than 1 μm.

6. The lyophilized composition of claim 1, wherein the nanoparticle complexes have a dissociation constant between about $1\times10^{-11}$ M and about $1\times10^{-9}$ M.

7. The lyophilized composition of claim 1, wherein the albumin is human serum albumin.

8. The lyophilized composition of claim 1, wherein the HER is HER2.

9. The lyophilized composition of claim 1, wherein the antibodies are trastuzumab, ado-trastuzumab emtansine, cetuximab, panitumumab, or pertuzumab.

10. The lyophilized composition of claim 1 which does not contain a bulking agent.

11. The lyophilized composition of claim 1, wherein said nanoparticle complexes have an average size between about 130 nm and about 800 nm.

12. The lyophilized composition of claim 1, wherein the ratio of albumin-paclitaxel nanoparticle to antibody is between 10:1 and 10:30.

13. The lyophilized composition of claim 1, wherein the ratio of albumin-paclitaxel nanoparticle to antibody is between 10:2 and 10:6.

14. The lyophilized composition of claim 9, wherein less than 0.01% of nanoparticle complexes have a size greater than 800 nm.

15. The lyophilized composition of claim 9, wherein said complexes have an average size of less than 1 μm.

16. The lyophilized composition of claim 9, wherein said nanoparticle complexes have an average size between about 130 nm and about 800 nm.

17. The lyophilized composition of claim 9, wherein the ratio of albumin-paclitaxel nanoparticle to antibody is between 10:1 and 10:30.

18. The lyophilized composition of claim 9, wherein the ratio of albumin-paclitaxel nanoparticle to antibody is between 10:2 and 10:6.

19. The lyophilized composition of claim 1, wherein each of the nanoparticle complexes comprises between about 100 and about 1000 antibodies.

20. The lyophilized composition of claim 1, further comprising at least one additional cancer therapeutic agent.

21. The lyophilized composition of claim 1, wherein the antibodies are associated with the albumin through non-covalent bonds.

22. The lyophilized composition of claim 1, wherein the paclitaxel is associated with the albumin through non-covalent bonds.

23. The lyophilized composition of claim 9, wherein the antibodies are associated with the albumin through non-covalent bonds.

24. The lyophilized composition of claim 9, wherein the paclitaxel is associated with the albumin through non-covalent bonds.

* * * * *

UNITED STATES PATENT AND TRADEMARK OFFICE
CERTIFICATE OF CORRECTION

| | |
|---|---|
| PATENT NO. | : 10,391,055 B2 |
| APPLICATION NO. | : 15/331754 |
| DATED | : August 27, 2019 |
| INVENTOR(S) | : Markovic et al. |

It is certified that error appears in the above-identified patent and that said Letters Patent is hereby corrected as shown below:

On the Title Page

Item (56) References Cited, OTHER PUBLICATIONS, Page 9, Column 1, Line 23 Edwards et al. cite: Please correct "334:103-118." to read -- 334:103-118 (2003). --

In the Specification

Column 7, Line 10: Please correct "30 µg/m²" to read -- 30 mg/m² --

Column 8, Line 19: Please correct "scrum" to read -- serum --

Column 9, Line 12: Please correct "the half-life" to read -- the $C_{max}$, half-life --

Column 9, Line 25: Please correct "shows the and" to read -- shows the $C_{max}$ and --

Column 39, Line 31: Please correct "2 nag/mL" to read -- 2 mg/mL --

Column 43, Line 3: Please correct "AR" to read -- AB --

Column 43, Line 58: Please correct "$1 \times 10^b$" to read -- $1 \times 10^6$ --

Column 48, Line 37: Please correct "(3200" to read -- (320 µl) --

Signed and Sealed this
Eighteenth Day of February, 2020

Andrei Iancu
*Director of the United States Patent and Trademark Office*